United States Patent [19]

Dumaitre et al.

[11] Patent Number: 5,604,237
[45] Date of Patent: Feb. 18, 1997

[54] ACRIDINE DERIVATIVES

[75] Inventors: Bernard A. Dumaitre; Nerina Dodic, both of Les Ulis, France

[73] Assignee: Laboratoires Glaxo SA, Paris, France

[21] Appl. No.: 468,620

[22] Filed: Jun. 6, 1995

Related U.S. Application Data

[63] Continuation of Ser. No. 348,946, Nov. 25, 1994, which is a continuation of Ser. No. 84,258, filed as PCT/EP92/00020 Jan. 7, 1992, abandoned.

[30] Foreign Application Priority Data

| Jan. 11, 1991 | [GB] | United Kingdom | 9100628 |
| Jan. 11, 1991 | [GB] | United Kingdom | 9100637 |
| Jul. 24, 1991 | [GB] | United Kingdom | 9115956 |
| Jul. 24, 1991 | [GB] | United Kingdom | 9115981 |

[51] Int. Cl.$^6$ .................. C07D 219/06; C07D 401/12; A61K 31/435; A61K 31/47
[52] U.S. Cl. .................. 514/297; 546/103
[58] Field of Search .................. 546/103; 514/297

[56] References Cited

U.S. PATENT DOCUMENTS

| 4,021,551 | 5/1977 | Cullen | 514/297 |
| 4,127,573 | 11/1978 | Gorvin | 546/103 |
| 4,250,182 | 2/1981 | Gorvin . | |
| 4,479,000 | 10/1984 | Rewcastle et al. | 546/23 |
| 4,590,277 | 5/1986 | Atwell et al. | 546/103 |
| 4,803,204 | 2/1989 | Dhar | 514/232 |
| 5,240,936 | 8/1993 | Chiou | 514/297 |
| 5,296,602 | 3/1994 | Su et al. | 546/103 |

FOREIGN PATENT DOCUMENTS

| 0098098 | 1/1984 | European Pat. Off. . | |
| 048898 | 1/1984 | European Pat. Off. . | |
| 0363212 | 4/1990 | European Pat. Off. . | |
| 0361485 | 4/1990 | European Pat. Off. . | |
| 494623 | 7/1992 | European Pat. Off. | 514/297 |
| WO90/15599 | 12/1990 | WIPO . | |

OTHER PUBLICATIONS

Hyafil et al., *Cancer Research*, 53, 4595–4602, Oct. 1, 1993.
Rewcastle et al., *Synthetic Communications*, 17(3), 309–317, 1987.

Palmer et al. J. Med. Chem vol. 31 pp. 707–712 (1988).

Denny et al, J. Med. Chem vol. 30 pp. 658–663 (1987).

Hyafil, et al. CA Previews vol. 93, abstract 502037 (1993).

*Primary Examiner*—Donald G. Daus
*Attorney, Agent, or Firm*—Bacon & Thomas

[57] ABSTRACT

These are provided compounds of formula I wherein A represents an oxygen or a sulphur atom, a bond or a group $(CH_2)_l NR^9$ (where $l$ represents zero or 1 and $R^9$ represents a hydrogen atom or a methyl group); B represents a $C_{1-4}$ alkylene chain optionally substituted by a hydroxyl group, except that the hydroxyl group and moiety A can not be attached to the same carbon atom when A represents an oxygen or sulphur atom or a group $(CH_2)_l NR^9$, or when A represents a bond B may also represent a $C_{2-4}$ alkenylene chain; $R^3$ represents a hydrogen atom or a $C_{1-4}$ alkyl group; m represents 1 or 2; $R^7$ represents a hydrogen atom or $R^3$ and $R^7$ together form a group $—(CH_2)_n—$ where n represents 1 or 2. These compounds can sensitize multidrug-resistant cancer cells to chemotherapeutic agents and may be formulated for use in therapy, particularly to improve or increase the efficacy of an antitumor drug.

15 Claims, No Drawings

ACRIDINE DERIVATIVES

This application is a continuation of pending application Ser. No. 08/348,946 filed Nov. 25, 1994, which is a continuation of application Ser. No. 08/084,258, filed Jul. 26, 1993, now abandoned, which is a section 371 of PCT/EP92/00020, filed Jan. 7, 1992.

This invention relates to acridine derivatives, to processes for their preparation, to pharmaceutical compositions containing them, and to their medical use. In particular it relates to compounds and compositions which are capable of sensitizing multidrug-resistant cancer cells to chemotherapeutic agents.

In many patients, the efficacy of cancer chemotherapy is initially poor or decreases after initial treatment due to the development of resistance to anticancer drugs, known as multidrug-resistance. Multidrug-resistance is a process whereby malignant cells become resistant to structurally diverse chemotherapeutic agents following treatment with a single anti-tumour drug. This acquired drug resistance can be a major clinical obstacle in the treatment of cancer. Some tumours are intrinsically multidrug-resistant, and hence do not respond to chemotherapy.

It has been shown that this type of resistance can be reversed by some calcium channel blockers such as nicardipine and verapamil, by antiarrhythmic agents such as amiodarone and quinidine, as well as by natural products such as cepharanthine. However, these compounds exert their multidrug resistant cell sensitizing activity only at very high doses, well above their intrinsic toxic level, and this severely limits their clinical use in the field of cancer chemotherapy.

A novel group of compounds has now been found which can sensitize multidrug-resistant cancer cells to chemotherapeutic agents at dose levels at which these novel compounds show no toxicity.

Thus, the present invention provides a compound of formula (I):

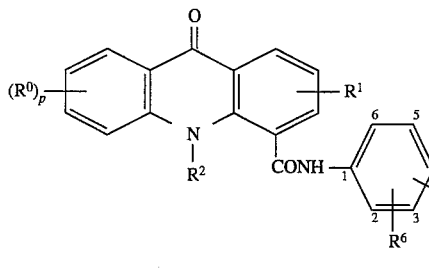

(I)

wherein
$R^0$ represents a hydrogen or halogen atom, or a $C_{1-4}$alkyl, $C_{1-4}$alkoxy, $C_{1-4}$alkylthio, amino or nitro group;

p represents 1; or when $R^0$ represents $C_{1-4}$alkoxy may also represent 2 or 3;

$R^1$ represents a hydrogen or halogen atom, or a $C_{1-4}$alkyl, $C_{1-4}$alkoxy or $C_{1-4}$alkylthio group;

$R^2$ represents a hydrogen atom or a $C_{1-4}$alkyl group;

A represents an oxygen or a sulphur atom, a bond or a group $(CH_2)_l NR^9$ (where l represents zero or 1 and $R^9$ represents a hydrogen atom or a methyl group);

B represents a $C_{1-4}$ alkylene chain optionally substituted by a hydroxyl group, except that the hydroxyl group and moiety A cannot be attached to the same carbon atom when A represents an oxygen or sulphur atom or a group $(CH_2)_1 NR^9$, or when A represents a bond B may also represent a $C_{2-4}$alkenylene chain;

$R^3$ represents a hydrogen atom or a $C_{1-4}$alkyl group;

m represents 1 or 2;

$R^4$ represents a hydrogen or a halogen atom, or a $C_{1-4}$alkyl, $C_{1-4}$alkoxy or $C_{1-4}$alkylthio group;

$R^5$ represents a hydrogen atom or a $C_{1-4}$alkoxy group;

$R^6$ represents a hydrogen atom or a $C_{1-4}$alkyl or $C_{1-4}$alkoxy group;

$R^7$ represents a hydrogen atom or $R^3$ and $R^7$ together form a group $-(CH_2)_n-$ where n represents 1 or 2;

$R^8$ represents a hydrogen atom or a $C_{1-4}$alkoxy group; the group

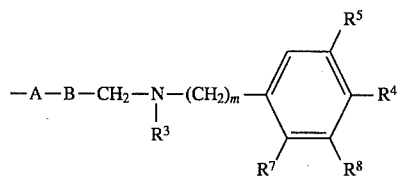

is attached at the benzene ring 3 or 4 position relate to the carboxamide substituent, provided that when the group is attached at the benzene ring 3 position then $R^6$ must be attached at the benzene ring 6 position; and salts and solvates thereof including physiologically acceptable salts and solvates thereof.

As used herein, an alkyl group, either as such or as part of an alkoxy or alkylthio group may be a straight chain or branched chain alkyl group, for example a methyl, ethyl or prop-2-yl group.

A halogen substituent may be a fluorine, chlorine, bromine or iodine atom.

The group(s) $R^0$, when other than a hydrogen atom, may be situated at the 5, 6, 7 or 8-position of the acridone molecule, and the group $R^1$ when other than a hydrogen atom, may be situated at the 1, 2 or 3-position of the acridone molecule.

Examples of the chain $-A-B-CH_2-$ include $-(CH_2)_2-$, $-(CH_2)_3-$, $-(CH_2)_4-$, $-(CH_2)_5-$, $-CH_2NMe(CH_2)_2-$, $-CH=CHCH_2-$, $-CH_2CH=CHCH_2-$, $-CH(OH)CH_2-$, $-O(CH_2)_2-$, $-O(CH_2)_3-$, $-OCH_2CH(OH)CH_2-$, $-NH(CH_2)_2-$, $-S(CH_2)_2-$ and $-S(CH_2)_3-$.

A preferred class of compounds of formula (I) is that in which $R^0$ represents a hydrogen or fluorine atom, or a $C_{1-4}$alkoxy (e.g. methoxy) group, $C_{1-4}$alkyl (e.g. methyl) or $C_{1-4}$alkylthio (e.g methylthio) group, and $R^1$ is a hydrogen atom. When $R^0$ represents a substituent other than a hydrogen atom, an $R^0$ group is preferably situated at the 5-position of the acridone molecule.

Another preferred class of compounds of formula (I) is that in which $R^2$ represents a hydrogen atom.

When $R^3$ represents a hydrogen atom or a $C_{1-4}$alkyl group, preferably $R^3$ represents a $C_{1-4}$alkyl (e.g. methyl) group.

Yet another preferred class of compounds of formula (I) is that in which $R^4$ represents a hydrogen atom or a $C_{1-4}$alkoxy (e.g. methoxy) group, $R^5$ represents a hydrogen atom or a $C_{1-4}$alkoxy (e.g. methoxy) group and $R^8$ represents a hydrogen atom or a $C_{1-4}$alkoxy (e.g methoxy), group, provided that at least one of $R^4$, $R^5$ and $R^8$ represents a $C_{1-4}$alkoxy (e.g. methoxy) group. A particularly preferred class of compounds of formula (I) is that in which $R^4$ and $R^5$ each represent a $C_{1-4}$alkoxy (e.g. methoxy) group and $R^8$ represents a hydrogen atom.

A further preferred class of compounds of formula (I) is that in which $R^6$ represents a hydrogen atom or a methyl, ethyl, methoxy or ethoxy group.

A preferred group of compounds of formula (I) is that in which m represents 1 and $R^3$ and $R^7$ together form a group —$(CH_2)_2$—, and physiologically acceptable salts and solvates thereof.

A particular group of compounds of formula (I) is that of formula (Ia)

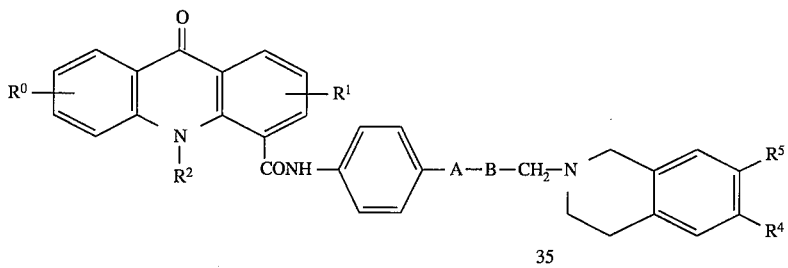

(Ia)

wherein
$R^0$ represents a hydrogen or halogen atom, or a $C_{1-4}$alkyl, $C_{1-4}$alkoxy, $C_{1-4}$alkylthio or nitro group;
$R^1$ represents a hydrogen or halogen atom, or a $C_{1-4}$alkyl, $C_{1-4}$alkoxy or $C_{1-4}$alkylthio group;
$R^2$ represents a hydrogen atom or a $C_{1-4}$alkyl group;
A represents an oxygen or a sulphur atom or a bond;
B represents an unsubstituted $C_{1-4}$alkylene chain;
$R^4$ and $R^5$ each independently represents a $C_{1-4}$alkoxy group; and physiologically acceptable salts and solvates thereof.

A particularly preferred group of compounds of formula (I) is that of formula (Ia) in which $R^0$ represents a hydrogen or fluorine atom or a $C_{1-4}$alkoxy (e.g. methoxy) or $C_{1-4}$alkyl (e.g. methyl) group, $R^1$ and $R^2$ each represent a hydrogen atom and $R^4$ and $R^5$ each represent a $C_{1-4}$alkoxy (e.g. methoxy) group. Such compounds in which the $R^0$ group is situated at the 5-position of the acridone molecule are especially preferred.

It is to be understood that the present invention includes all combinations of the aforementioned particular and preferred groups.

A particularly preferred compound according to the invention is 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide and physiologically acceptable salts and solvates thereof.

Other preferred compounds according to the invention are:

9,10-dihydro-5-methoxy-9-oxo-N-[4-[[3-(1,2,3,4-tetrahydro-6,7-dimethoxy-2-isoquinolinyl)propyl]thio]phenyl]-4-acridinecarboxamide;

5-fluoro-9,10-dihydro-9-oxo-N-[4-[[3-(1,2,3,4-tetrahydro-6,7-dimethoxy-2-isoquinolinyl)propyl]thio]phenyl]-4-acridinecarboxamide;

9,10-dihydro-5-methoxy-9-oxo-N-[4-[3-(1,2,3,4-tetrahydro-6,7-dimethoxy-2-isoquinolinyl)propoxy]phenyl]-4-acridinecarboxamide;

9,10-dihydro-5-methyl-9-oxo-N-[4-[[3-(1,2,3,4-tetrahydro-6,7-dimethoxy-2-isoquinolinyl)propyl]thio]phenyl]-4-acridinecarboxamide;

9,10-dihydro-5-methoxy-N-[2-methoxy-4-[3-(1,2,3,4-tetrahydro-6,7-dimethoxy-2-isoquinolinyl)propyl]phenyl]-9-oxo-4-acridinecarboxamide;

9,10-dihydro-N-[2-methoxy-4-[3-(1,2,3,4-tetrahydro-6,7-dimethoxy-2-isoquinolinyl)propyl]phenyl]-5-methyl-9-oxo-4-acridinecarboxamide;

and physiologically acceptable salts and solvates thereof.

Further preferred compounds according to the invention are:

N-[4-[4-[[(3,4-dimethoxyphenyl)methyl]methylamino]butyl]phenyl]-9,10-dihydro-9-oxo-4-acridinecarboxamide;

N-[4-[2-[[(3,4-dimethoxyphenyl)methyl]methylamino]ethyl]phenyl]-9,10-dihydro-9-oxo-4-acridinecarboxamide;

N-[4-[4-[[(3,4-dimethoxyphenyl)methyl]methylamino]butyl]phenyl]-5-fluoro-9,10- dihydro-9-oxo-4-acridinecarboxamide;

N-[4-[2-[[(3,4-dimethoxyphenyl)methyl]methylamino]ethyl]phenyl]-9,10-dihydro-5-methoxy-9-oxo-4-acridinecarboxamide;

and physiologically acceptable salts and solvates thereof.

Yet further preferred compounds according to the invention are:

N-[4-[3-[[(3,4-dimethoxyphenyl)methyl]methylamino]propyl]phenyl]-5-fluoro-9,10-dihydro-9-oxo-4-acridinecarboxamide;

N-[4-[2-[[(3,4-dimethoxyphenyl)methyl]methylamino]ethyl]phenyl]-5-fluoro-9,10-dihydro-9-oxo-4-acridinecarboxamide;

N-[4-[[3-[[(3,4-dimethoxyphenyl)methyl]methylamino]propyl]thio]phenyl]-9,10-dihydro-5-methoxy-9-oxo-4-acridinecarboxamide;

and physiologically acceptable salts and solvates thereof.

Other preferred compounds according to the invention are:

N-[4-[[3-[[(3,4-dimethoxyphenyl)methyl]methylamino]propyl]thio]phenyl]-9,10-dihydro-9-oxo-4-acridinecarboxamide;

N-[4-[4-[[(3,4-dimethoxyphenyl)methyl]methylamino]butyl]phenyl]-9,10-dihydro-5-methoxy-9-oxo-4-acridinecarboxamide;

N-[4-[3-[[2-(3,4-dimethoxyphenyl)ethyl]methylamino]
propyl]phenyl]-9,10-dihydro-9-oxo-4-acridinecarboxamide;

N-[4-[2-[[2-(3,4-dimethoxyphenyl)ethyl]methylamino]
ethoxy]phenyl]-9,10-dihydro-5-methoxy-9-oxo-4-acridinecarboxamide;

N-[4-[3-[[(3,4-dimethoxyphenyl)methyl]methylamino]
propoxy]phenyl]-9,10-dihydro-9-oxo-4-acridinecarboxamide;

N-[4-[3-[[(3,4-dimethoxyphenyl)methyl]methylamino]
propoxy]phenyl]-5-fluoro-9,10-dihydro-9-oxo-4-acridinecarboxamide;

N-[4-[2-[[2-(3,4-dimethoxyphenyl)ethyl]methylamino]
ethyl]phenyl]-9,10-dihydro-9-oxo-4-acridinecarboxamide;

N-[4-[5-[[(3,4-dimethoxyphenyl)methyl]methylamino]
pentyl]phenyl]-5-fluoro-9,10-dihydro-9-oxo-4-acridinecarboxamide;

N-[4-[3-[[(3,4-dimethoxyphenyl)methyl]methylamino]
propyl]phenyl]-9,10-dihydro-9-oxo-4-acridinecarboxamide;

N-[4-[2-[[(3,4-dimethoxyphenyl)methyl]methylamino]
ethylamino]phenyl]-9,10-dihydro-5-methoxy-9-oxo-4-acridinecarboxamide;

N-[4-[[3-[[(3,4-dimethoxyphenyl)methyl]methylamino]
propyl]thio]phenyl]-9,10-dihydro-5-fluoro-9-oxo-4-acridinecarboxamide;

N-[4-[2-[[(3,4-dimethoxyphenyl)methyl]methylamino]
ethyl]phenyl]-9,10-dihydro-5-methylthio-9-oxo-4-acridinecarboxamide;

N-[4-[2-[[(3,4-dimethoxyphenyl)methyl]methylamino]
ethyl]phenyl]-9,10-dihydro-5-methyl-9-oxo-4-acridinecarboxamide;

N-[4-[3-[[(3,4-dimethoxyphenyl)methyl]methylamino]
propoxy]phenyl]-9,10-dihydro-5-methyl-9-oxo-4-acridinecarboxamide;

and physiologically acceptable salts and solvates thereof.

Yet further preferred compounds according to the invention are:

N-[4-[2-[[2-(3,4-dimethoxyphenyl)ethyl]methylamino]
ethyl]phenyl]-9,10-dihydro-9-oxo-4-acridinecarboxamide;

N-[4-[4-[[2-(3,4-dimethoxyphenyl)ethyl]methylamino]
butyl]phenyl]-9,10-dihydro-9-oxo-4-acridinecarboxamide;

N-[4-[2-[[2-(4-methoxyphenyl)ethyl]methylamino]ethyl]
phenyl]-9,10-dihydro-9-9-oxo-4-acridinecarboxamide;

N-[4-[2-[[2-(3,4-dimethoxyphenyl)ethyl]methylamino]
ethoxy]phenyl]-9,10-dihydro-2-(methylthio)-9-oxo-4-acridinecarboxamide;

N-[4-[3-[2-(3,4-dimethoxyphenyl)ethyl]methylamino]
propoxy]phenyl]-9,10-dihydro-9-oxo-4-acridinecarboxamide;

N-[4-[2-[[2-(4-methoxyphenyl)ethyl]methylamino]
ethoxy]phenyl]-9,10-dihydro-9-oxo-4-acridinecarboxamide;

N-[4-[2-[[(3,4-dimethoxyphenyl)methyl]methylamino]
ethoxy]phenyl]-9,10-dihydro-9-oxo-4-acridinecarboxamide;

N-[4-[3-[[(3,4-dimethoxyphenyl)methyl]methylamino]
propoxy]phenyl]-9,10-dihydro-5-methoxy-9-oxo-4-acridinecarboxamide;

N-[4-[[2-[[(3,4-dimethoxyphenyl)methyl]methylamino]
ethyl]thio]phenyl]-9,10-dihydro-9-oxo-4-acridinecarboxamide;

and physiologically acceptable salts and solvates thereof.

Suitable physiologically acceptable salts of the compounds of formula (I) include acid addition salts formed with organic or inorganic acids, for example, hydrochlorides, hydrobromides, sulphates, alkyl- or arylsulphonates (e.g. methanesulphonates or p-toluenesulphonates), phosphates, acetates, citrates, succinates, lactates, tartrates, fumarates and maleates. The solvates may, for example, be hydrates.

Other salts which are not physiologically acceptable may be useful in the preparation of compounds of formula (I) and these form a further part of the invention.

The ability of the compounds of formula (I) to sensitize multidrug-resistant cells has been demonstrated in vitro in the multidrug-resistant Chinese hamster ovary cell line (described by Bech-Hansen et al., *J. Cell. Physiol.*, 1976, 88, 23–32) and the multidrug-resistant human mammary carcinoma line (described by Batist et al., (*J. Biol. Chem.*, 1986, 261, 1544–1549) using an assay similar to that described by Carmichael et al., *Cancer Research*, 1987, 47, 936.

The ability of the compounds of formula (I) to sensitize multidrug-resistant cells has also been demonstrated in vivo in the tumour line P388R (described by Johnson et al., *Cancer Treat. Rep.*, 1978, 62, 1535–1547). The methodology used is similar to that described by Boesch et al., *Cancer Research*, 1991, 51, 4226–4233. However, in our study the compounds were administered orally, intravenously or intraperitoneally in a single dose.

The present invention accordingly provides a compound of formula (I) or a physiologically acceptable salt or solvate thereof for use in therapy, more particularly for use in the treatment of a mammal, including a human, which is suffering from cancer to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

The present invention also provides a method of treatment of a mammal, including a human, which is suffering from cancer, which method comprises administering to said mammal an effective amount of a compound of formula (I) or a physiologically acceptable salt or solvate thereof to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

In another aspect, the present invention provides the use of a compound of formula (I) or a physiologically acceptable salt or solvate thereof for the manufacture of a medicament for the treatment of a mammal, including a human, which is suffering from cancer to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

It will be appreciated that the compounds according to the present invention are administered in conjunction with an antitumour drug. Thus, in a further aspect, the present invention provides a product containing a compound of formula (I) or a physiologically acceptable salt or solvate thereof and an antitumour drug as a combined preparation for simultaneous, separate or sequential use in treating cancer, more particularly to:

(a) improve or increase the efficacy of said antitumour drug; or (b) increase or restore sensitivity of a tumour to an antitumour drug; or (c) reverse or reduce resistance, whether acquired, induced or inate, of a tumour to an antitumour drug.

Examples of suitable antitumour drugs for use in conjunction with compounds of the present invention include Vinca alkaloids (e.g. vincristine, vinblastine and vinorelbine), anthracyclines (e.g. daunorubicin, doxorubicin and aclarubicin), taxol and derivatives thereof (e.g. taxotere), podophyllotoxins (e.g. etoposide and VP16), mitoxantrone, actinomycin, colchicine, gramicidine D, amsacrine or any drug having cross-resistance with the above drugs characterised by the so-called MDR phenotype.

It will be appreciated that if administration of the two drugs is not simultaneous, the delay in administering the second of the active ingredients should not be such as to lose the beneficial effect of the combination.

Thus, in a further aspect, the present invention provides a compound of formula (I) or a physiologically acceptable salt or solvate thereof and an anticancer drug in the presence of each other in the human or non-human animal body for use in treating cancer, more particularly to:

(a) improve or increase the efficacy of said antitumour drug; or (b) increase or restore sensitivity of a tumour to an antitumour drug; or (c) reverse or reduce resistance, whether acquired, induced or inate, of a tumour to an antitumour drug.

Some tumours are often intrinsically multidrug-resistant, notably colon carcinomas, renal cell carcinomas, hepatomas and adrenocortical carcinomas.

Other types of tumour are often initially sensitive but can become multidrug-resistant, notably leukaemias, lymphomas, myelomas, paediatric tumours (e.g. neuroblastomas), sarcomas, and breast, ovarian and lung cancers.

Hence the compounds of the invention are particularly useful in the treatment of mammals, including humans, receiving chemotherapy for one of the above types of cancer.

In using a compound of formula (I) or a physiologically acceptable salt or solvate thereof and an antitumour drug it may be preferable to employ the active ingredients in the form of separate pharmaceutical formulations, although a single combined formulation can be used as demonstrated hereinafter. However, in the latter formulation both active ingredients must of course be stable and mutually compatible in the particular formulation employed.

Pharmaceutical formulations of suitable antitumour drugs and appropriate dosages and dosage rates will generally correspond with those one would use if administering the antitumour drug alone to treat a tumour.

Suitable pharmaceutical formulations and appropriate dosages and dosage rates of compounds of formula (I) and physiologically acceptable salts and solvates thereof are described hereinafter.

Thus, in a further aspect, the invention provides a pharmaceutical composition which comprises a compound of formula (I) or a physiologically acceptable salt or solvate thereof together with one or more physiologically acceptable carriers or excipients.

In another aspect, the present invention provides a pharmaceutical composition which comprises an active amount of a compound of formula (I) or a physiologically acceptable salt or solvate thereof for use in the treatment of a mammal which is suffering from cancer, to:

(a) improve or increase the efficacy of an antitumour drug; or (b) increase or restore sensitivity of a tumour to an antitumour drug; or (c) reverse or reduce resistance, whether acquired, induced or inate, of a tumour to an antitumour drug.

The compounds according to the invention may be formulated for oral, buccal, parenteral or rectal administration, of which oral and parenteral are preferred.

For oral administration, the pharmaceutical compositions may take the form of, for example, tablets or capsules prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium hydrogen phosphate); lubricants (e.g. magnesium stearate, talc or silica); disintegrants (e.g. sodium lauryl sulphate or sodium starch glycolate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g. sorbitol syrup, cellulose derivatives or hydrogenated edible fats); emulsifying agents (e.g. lecithin or acacia); non-aqueous vehicles (e.g. almond oil, oily esters, ethyl alcohol or fractionated vegetable oils); and preservatives (e.g. methyl or propyl-p-hydroxybenzoates or sorbic acid). The preparations may also contain buffer salts, flavouring, colouring and sweetening agents as appropriate.

Preparations for oral administration may be suitably formulated to give controlled release of the active compound.

For buccal administration the compositions may take the form of tablets or lozenges formulated in conventional manner.

The compounds of the invention may be formulated for parenteral administration by bolus injection or continuous infusion. Formulations for injection may be presented in unit dosage form e.g. in ampoules or in multi-dose containers, with an added preservative. The compositions may take such forms as suspensions, solutions or emulsions in oily, aqueous or alcoholic vehicles, and may contain formulatory agents such as suspending, stabilising and/or dispersing agents. Alternatively, the active ingredient may be in powder form for constitution with a suitable vehicle, e.g. sterile pyrogen-free water, before use.

The compounds of the invention may also be formulated in rectal compositions such as suppositories or retention enemas, e.g. containing conventional suppository bases such as cocoa butter or other glycerides.

A proposed daily dose of the compounds of the invention for administration to a human (of approximately 70 kg body weight) is about 10 mg to 1000 mg, more preferably about 25 mg to 500 mg. It will be appreciated that it may be necessary to make routine variations to the dosage, depending on the age and condition of the patient, and the route of administration. For example, a daily dose of about 1 mg/kg may be appropriate for administration to a human by infusion. The daily dose may be given as a single unit or as two or more subunits administered after appropriate time intervals.

Compounds of general formula (I) and physiologically acceptable salts and solvates thereof may be prepared by the general methods outlined hereinafter. In the following description, the groups $R^0$ to $R^8$ m, p, A and B are as defined for compounds of formula (I) unless otherwise specified.

Thus according to a first general process (A), a compound of formula (I) may be prepared by reacting a compound of formula (II):

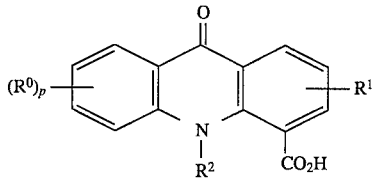

with a compound of formula (III)

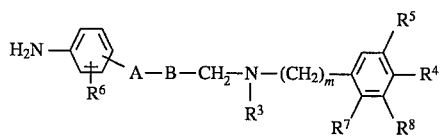

The reaction may be effected using a coupling reagent standardly used in peptide synthesis, such as dicyclohexylcarbodiimide (optionally in the presence of 1-hydroxybenzotriazole), diphenylphosphoryl azide or N,N'-carbonyldiimidazole. The reaction may be conveniently effected in an inert solvent such as an ether (e.g. tetrahydrofuran), a halogenated hydrocarbon (e.g. dichloromethane), an amide (e.g. dimethylformamide) or a ketone (e.g. acetone), and at a temperature of, for example, −10° to +100° C., more preferably at about room temperature.

According to another general process (B), a compound of formula (I) may be prepared by reacting a compound of formula (IV):

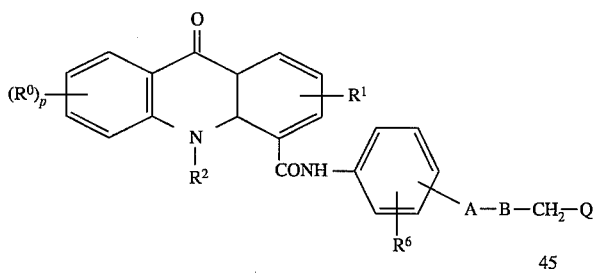

wherein Q represents a halogen (e.g. bromine) atom, with a compound of formula (V):

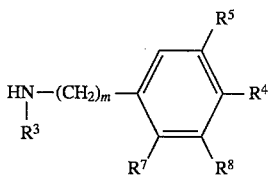

or a salt thereof. The reaction may be effected in the presence of an acid acceptor such as an alkali metal carbonate (e.g. potassium carbonate), in the presence or absence of a solvent, at an elevated temperature (e.g. 50° to 120° C.). Suitable solvents include ketones (e.g. acetone, methylethylketone or methylisopropylketone) and alcohols (e.g. ethanol or isopropanol).

Compounds of formula (III) in which A represents an oxygen atom or a bond may be prepared by the reduction of a compound of formula (VI):

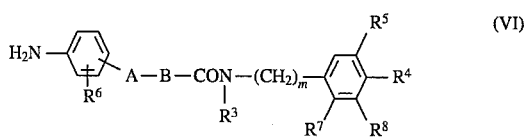

(in which A is an oxygen atom or a bond) with a suitable reducing agent such as lithium aluminium hydride in an inert solvent such as an ether (e.g. tetrahydrofuran) at an elevated temperature.

Compounds of formula (VI) may be prepared by the reduction of a compound of formula (VII):

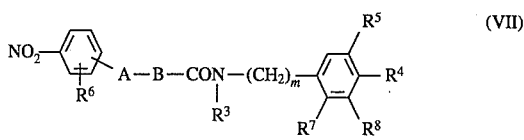

by catalytic hydrogenation, for example using hydrogen in the presence of a noble metal catalyst (e.g. palladium). The catalyst may be supported on, for example, charcoal. The hydrogenation may be effected in a solvent such as an alcohol (e.g. ethanol), and conveniently at a temperature in the range of 20° to 100° C. (e.g. 20° to 50° C.) and atmospheric pressure. Alternatively, the reduction may be effected using iron and concentrated hydrochloric acid at an elevated temperature (e.g. reflux). This alternative reduction procedure leaves any double bond present in the compound of formula (VII) intact.

Compounds of formula (VII) may be prepared by the reaction of a compound of formula (VIII):

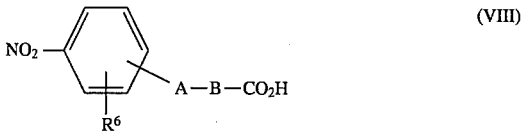

or an activated derivative thereof, with a compound of formula (V) as defined previously or a salt thereof, optionally in the presence of a base such as an organic base (e.g. methylamine or N,N-diisopropylethylamine) or an inorganic base such as an alkali metal carbonate (e.g. potassium carbonate) or hydrogen carbonate (e.g. sodium hydrogen carbonate).

When the free acid (VIII) is reacted with the amine (V), coupling reagents and conditions described in process (A) for the reaction of a compound of formula (II) with a compound of formula (III) may be used.

When an activated derivative of a compound of formula (VIII) is used, this may be, for example, an acid halide (e.g. an acid chloride), prepared by reacting the free acid (VIII)

with a halogenating reagent (e.g. thionyl chloride). This activated derivative of a compound of formula (VIII) may be reacted with a compound of formula (V) in a solvent such as acetone in the presence of a base such as sodium hydrogen carbonate.

Compounds of formula (VIII) wherein A represents a bond may be prepared by the nitration of a compound of formula (IX):

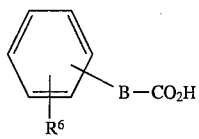

(IX)

with nitric acid.

Compounds of formula (VIII) wherein A represents a bond and B represents a group —CH=CH— may conveniently be prepared by the hydrolysis of a compound of formula (X):

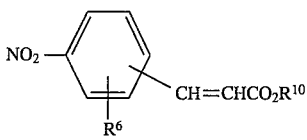

(X)

where $R^{10}$ represents a $C_{1-4}$alkyl group. The hydrolysis may be effected using conventional methods, for example, by using sodium hydroxide in aqueous ethanol.

Compounds of formula (X) may be prepared by the reaction of a compound of formula (XI):

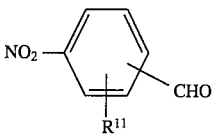

(XI)

where $R^{11}$ represents a hydrogen atom or a $C_{1-4}$alkyl, $C_{1-4}$alkoxy or hydroxyl group, with a compound of formula (XII):

Ph$_3$P=CHCO$_2$R$^{10}$     (XII)

where $R^{10}$ is as defined previously, in an inert solvent such as a hydrocarbon (e.g. toluene) and at an elevated temperature. For the preparation of a compound of formula (X) wherein $R^6$ represents a $C_{1-4}$alkoxy group from a compound of formula (XI) wherein $R^{11}$ represents a hydroxyl group, the above reaction is followed by alkylation of the hydroxyl group using, for example, an alkyl halide.

Compounds of formula (VIII) wherein A represents an oxygen atom may be prepared by the hydrolysis of a compound of formula (XIII):

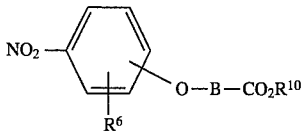

(XIII)

wherein $R^{10}$ is as defined above. The hydrolysis may be effected using conventional methods, for example, by using sodium hydroxide in aqueous ethanol.

Compounds of formula (XIII) may be prepared by the reaction of a compound of formula (XIV):

L—B—CO$_2$R$^{10}$     (XIV)

wherein L represents a halogen (e.g. bromine) atom, with a nitrophenol derivative in the presence of an alkali metal carbonate (e.g. potassium carbonate), in a solvent such as acetone.

Compounds of formula (III) wherein A represents an oxygen or sulphur atom or a bond may also be prepared by the reduction of a compound of formula (XV):

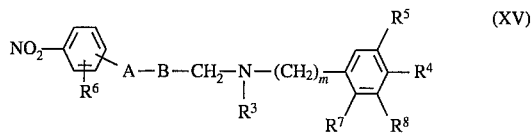

(XV)

(where A is an oxygen or sulphur atom or a bond) using the conditions described above for the reduction of a compound of formula (VII).

Compounds of formula (XV) may be prepared by heating a compound of formula (XVI):

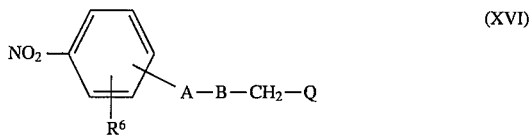

(XVI)

(wherein Q represents a halogen (e.g. bromine) atom and A is an oxygen or sulphur atom or a bond), with a compound of formula (V) as defined above under the conditions described in process (B) above.

Compounds of formula (XVI) wherein A represents an oxygen or a sulphur atom may be prepared by the reaction of a compound of formula (XVII):

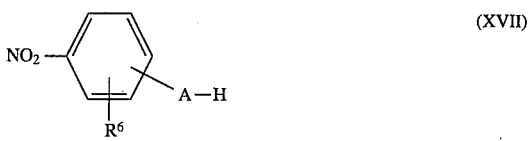

(XVII)

wherein A represents an oxygen or a sulphur atom, with a dihaloalkane Q—B—CH$_2$—Q in the presence of a suitable base such as an alkali metal carbonate (e.g. potassium carbonate).

Compounds of formula (XVI) wherein A represents a bond may be prepared by the reaction of a compound of formula (XVIII):

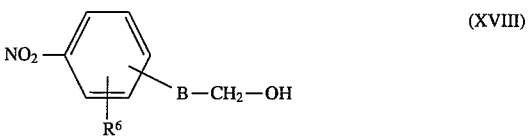

(XVIII)

with an halogenating reagent such as phosphorus tribromide.

Compounds of formula (XVIII) may be prepared by the reduction of a compound of formula (XIX):

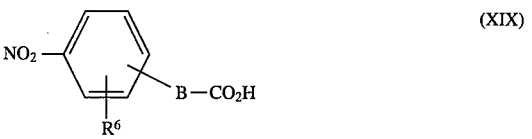

(XIX)

with a suitable reducing agent such as diborane.

Compounds of formula (XIX) may be prepared by subjecting a compound of formula (XX):

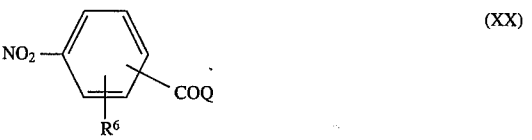

(XX)

wherein Q represents a halogen (e.g. chlorine) atom to one or more successive Arndt-Eisten syntheses (i.e. reaction with diazomethane followed by treatment with, for example, silver oxide and water).

It will be appreciated by one skilled in the art that compounds of formula (XIX) in which B represents an unsubstituted $C_{2-4}$alkylene chain may also be prepared by subjecting a compound of formula (XXI):

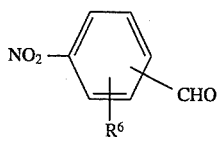

(XXI)

to a Wittig reaction with a suitable phosphorus ylid (e.g. $Ph_3P=CH(CH_2)_3OH$) followed by reduction of the double bond with a suitable reducing agent such as diborane, and oxidation of the primary alcohol to a carboxylic acid with a suitable oxidising agent such as chromium (VI) oxide.

Compounds of formula (III) wherein A represents a group $(CH_2)_l NR^9$ may be prepared by the reduction of a compound of formula (XXII):

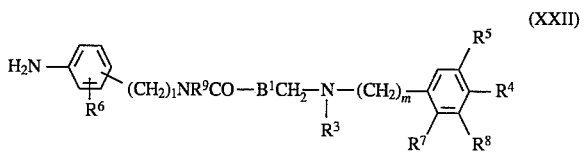

(XXII)

(in which $B^1$ is a bond or a $C_{1-3}$alkylene chain optionally substituted by a hydroxyl group) with a suitable reducing agent such as lithium aluminium hydride in an inert solvent such as an ether (e.g. tetrahydrofuran) at an elevated temperature.

Compounds of formula (XXII) may be prepared by the reduction of a compound of formula (XXIII):

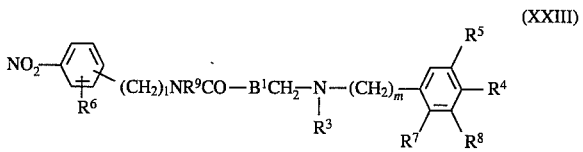

(XXIII)

by catalytic hydrogenation, for example as described above for preparing compounds of formula (VI).

Compounds of formula (XXIII) may be prepared by the reaction of a compound of formula (XXIV):

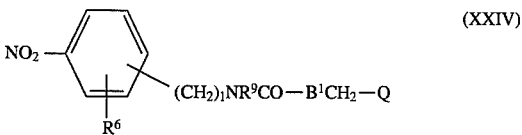

(XXIV)

[wherein Q represents a halogen (e.g. chlorine) atom] with a compound of formula (V) as defined previously under the conditions described above in process (B).

Compounds of formula (IV) may be prepared by the reaction of a compound of formula (II) as defined previously, with a compound of formula (XXV):

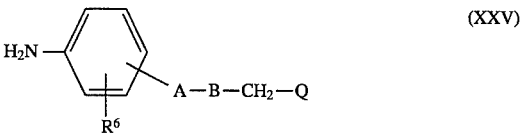

(XXV)

wherein Q represents a halogen (e.g. bromine) atom, under the conditions described in process (A) above for the reaction of a compound of formula (II) with a compound of formula (III).

Compounds of formula (V) wherein $R^3$ represents a $C_{1-4}$alkyl group may be prepared by reacting a compound of formula (XXVI):

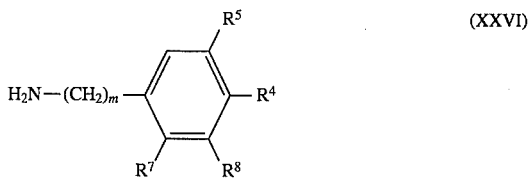

(XXVI)

with benzaldehyde, followed by a $C_{1-4}$alkyl halide. Hydrolysis of the resultant quaternary salt followed by treatment with dilute sodium hydroxide solution gives a compound of formula (V) wherein $R^3$ represents a $C_{1-4}$alkyl group.

It is to be understood that the general procedures above may be used to provide a compound of formula (I) in which B contains a hydroxyl substituent. However, it may be preferable to reduce an intermediate in which B contains an oxo group to provide the desired intermediate in which B contains a hydroxyl substituent at an appropriate stage in the overall procedure.

Intermediates of formulae (III), (IV), (VI), (VII), (VIII), (X), (XIII), (XV), (XVI), (XVIII), (XIX), (XXII) and (XXIII) are novel compounds and represent a further aspect of the present invention.

Compounds of formula (II) are either known, or may be prepared by conventional methods, such as those described by G. W. Rewcastle and W. A. Denny in *Synth. Commun.*, 1985, 217–222.

Compounds of formulae (V), (IX), (XI), (XII), (XIV), (XVII), (XX), (XXI), (XXIV) and (XXVI) are either known, or may be prepared by conventional methods.

Compounds of formula (XXV) are either known or may be prepared by conventional methods. Thus, for example, compounds of formula (XXV) wherein A represents an oxygen atom may be prepared by the reaction of a 4-acetamidophenol derivative with a dihaloalkane Q—$BCH_2$—Q, followed by acid hydrolysis using, for example, dilute hydrochloric acid.

Where it is desired to isolate a compound of the invention as a salt, for example a physiologically acceptable salt, this may be achieved by reacting the compound of formula (I) in the form of the free base with an appropriate acid, preferably with an equivalent amount, in a suitable solvent such as an alcohol (e.g. ethanol or methanol), an aqueous alcohol (e.g. aqueous ethanol), a halogenated hydrocarbon (e.g. dichloromethane), an ester (e.g. ethyl acetate) or an ether (e.g. tetrahydrofuran), or a mixture of two or more of such solvents.

Physiologically acceptable salts may also be prepared from other salts, including other physiologically acceptable salts, of the compound of formula (I) using conventional methods.

It will be appreciated that within the above multi-stage processes, the various methods described for the introduction of the desired groups required in the final product may be performed in sequences different from those described. The sequence of the reactions in multi-stage processes should of course be chosen so that the reaction conditions used do not affect groups in the molecule which are desired in the final product.

The invention is further illustrated by the following Intermediates and Examples which are not intended to limit the invention in any way. All temperatures are in °C. $^1$H NMR spectra were obtained for dilute solutions in $CDCl_3$ unless otherwise stated. Solvents were dried, where indicated, over sodium sulphate. Silica gel used for column chromatography was Merck 60, 230–400 mesh. The following abbreviatons are used: THF—tetrahydrofuran; DMF—dimethylformamide.

INTERMEDIATE 1

(a) 1,2,3,4-Tetrahydro-6,7-dimethoxy-2-[3-(4-nitrophenoxy)propyl]isoquinoline

A mixture of 1-(3-bromopropoxy)-4-nitrobenzene (10 g), 1,2,3,4-tetrahydro-6,7-dimethoxyisoquinoline hydrochloride (8.8 g) and potassium carbonate (10.6 g) in DMF (100 ml) was heated at 100° for 16 h. The mixture was then filtered and the filtrate evaporated. The residue was taken up in water and extracted with dichloromethane. The organic layer was washed with water, dried, and evaporated to give an oil which crystallised in ether to give the title compound (11.3 g), m.p. 100°.

The following compounds were prepared in a similar manner to Intermediate 1(a):

(b) 1,2,3,4-Tetrahydro-6,7-dimethoxy-2-[3-[(4-nitrophenyl)thio]propyl]isoquinoline The title compound (5.3 g) was obtained as an oil (which subsequently crystallised) from 1-[(3-bromopropyl)thio]-4-nitrobenzene (7.0 g) and 1,2,3,4-tetrahydro-6,7-dimethoxy-isoquinoline hydrochloride (5.8 g).

NMR includes d 4.05 (6H,s, 2×OCH$_3$).

(c) 1,2,3,4-Tetrahydro-6,7-dimethoxy-2-[2-(4-nitrophenyl)ethyl]-isoquinoline

The title compound (16 g) was obtained as a solid from 1-(2-bromoethyl)-4-nitrobenzene (10 g) and 1,2,3,4-tetrahydro-6,7-dimethoxyisoquinoline (10.9 g). M.p. 118°.

NMR includes d 3.9 (6H,s, 2×OCH$_3$).

(d) 1,2,3,4-Tetrahydro-6,7-dimethoxy-2-[4-(4-nitrophenyl)butyl]-isoquinoline

The title compound (12.6 g) was obtained as an oil from 1-(4-bromobutyl)-4-nitrobenzene (12.5 g) and 1,2,3,4-tetrahydro-6,7-dimethoxyisoquinoline hydrochloride (11.1 g). The product was purified by column chromatography eluting with dichloromethane:methanol (99:1).

NMR includes d 3.85 (6H, s, 2×OCH$_3$).

INTERMEDIATE 2

(a) 4-[3-(1,2,3,4-Tetrahydro-6,7-dimethoxy-2-isoquinolinyl)propoxy]benzenamine

A solution of Intermediate 1(a) (16 g) in ethanol (200 ml) was hydrogenated at room temperature and atmospheric pressure in the presence of 10% palladium on carbon (1.6 g). After hydrogen absorption was completed, the catalyst was filtered off and the solution was concentrated to give the title compound (14.7 g) as an oil which crystallised in hexane, m.p. 100°.

(b) 4-[[3-(1,2,3,4-Tetrahydro-6,7-dimethoxy-2-isoquinolinyl) propyl]thio]benzenamine Intermediate 1(b) (5.3 g) was dissolved in a mixture of methanol and concentrated hydrochloric acid (5 ml) at room temperature with stirring. Iron powder (3.8 g) was then added portionwise, and the mixture was heated under reflux for 1.5 h. The mixture was then cooled, poured onto ice, basified with sodium hydroxide and extracted with ethyl acetate. The organic layer was washed with water, dried and evaporated to give the title compound (4.35 g) as an oil.

IR: Freq NH$_2$: 3350 cm$^{-1}$.

(c) 4-[2-(1,2,3,4-Tetrahydro-6,7-dimethoxy-2-isoquinolinyl)ethyl]-benzenamine

Intermediate 1(c) (14 g) was reduced according to the method of Intermediate 2(b) to give the title compound (12 g) as a solid, m.p. 120°.

(d) 4-[4-(1,2,3,4-Tetrahydro-6,7-dimethoxy-2-isoquinolinyl)butyl]-benzenamine

Intermediate 1(d) (8.5 g) was reduced according to the method of Intermediate 2(a). The product was purified by column chromatography eluting with dichloromethane:methanol (99:1) to give the title compound (4.3 g) as an oil which solidified.

IR: Freq NH$_2$: 3350 cm$^{-1}$.

INTERMEDIATE 3

(a) 1,2,3,4-Tetrahydro-6,7-dimethoxy-2-[(4-nitrophenoxy)acetyl]isoquinoline

A mixture of (4-nitrophenoxy)acetic acid (50 g) and thionyl chloride (150 ml) was heated under reflux for 3 h. The solution was concentrated and then coevaporated with benzene to give 4-nitrophenoxyacetyl chloride as a solid. A solution of this solid (9.4 g) in acetone (100 ml) was added dropwise to a stirred mixture of 1,2,3,4-tetrahydro-6,7-dimethoxyisoquinoline hydrochloride (10 g) and sodium hydrogen carbonate (9 g) in acetone (100 ml) at 0°. Stirring was continued at room temperature for 16 h, the mixture was then filtered, and the filtrate was concentrated. The residue was treated with water and extracted with dichloromethane. The organic layer was washed with water, dried and concentrated to give the title compound (6.6 g) as an oil.

IR: Freq CO: 1650 cm$^{-1}$.

The following compound was prepared in a similar manner to Intermediate 3(a).

(b) 1,2,3,4-Tetrahydro-6,7-dimethoxy-2-[3-(4-nitrophenyl)-1-oxopropyl]isoquinoline The title compound (12.3 g) was obtained as a solid, m.p. 134° from 4-nitrobenzenepropanoic acid (9.75 g) and 1,2,3,4-tetrahydro-6,7-dimethoxyisoquinoline (11.6 g).

INTERMEDIATE 4

(a) 2-[(4-Aminophenoxy)acetyl]-1,2,3,4-tetrahydro-6,7-dimethoxyisoquinoline

Intermediate 3(a) (6.6 g) was dissolved in a mixture of methanol (100 ml) and concentrated hydrochloric acid (50 ml) at room temperature with stirring. Iron powder (5 g) was then added portionwise and the mixture was heated under reflux for 3 h. The mixture was then cooled, poured onto ice, basified with sodium hydroxide and extracted with ethyl acetate. The organic layer was washed with water, dried and evaporated to give the title compound (4 g) as an oil.

IR: Freq NH$_2$: 3360 cm$^{-1}$.

(b) 2-[3-(4-Aminophenyl)-1-oxopropyl]-1,2,3,4-tetrahydro-6,7-dimethoxyisoquinoline A solution of Intermediate 3(b) (12 g) in a mixture of ethanol:dioxan (18 ml; 5:1) was hydrogenated at room temperature and atmospheric pressure in the presence of 10% palladium on carbon (1.2 g). After hydrogen absorption was completed, the catalyst was filtered off and the solution was concentrated to give the title compound (11 g) as a solid.

IR: Freq NH$_2$: 3360 cm$^{-1}$ Freq CO: 1650 cm$^{-1}$.

INTERMEDIATE 5

(a) 4-[2-(1,2,3,4-Tetrahydro-6,7-dimethoxy-2-isoquinolinyl)ethoxy]benzenamine

A solution of Intermediate 4(a) (4 g) in THF (50 ml) was added dropwise to a stirred suspension of lithium aluminium hydride (1.8 g) in THF (20 ml) at room temperature, and the mixture was heated under reflux for 3 h. Water was added carefully to the cooled mixture which was then filtered, washed with THF, evaporated and extracted with dichloromethane. The organic layer was dried and evaporated to give the title compound (1.5 g) as an oil. IR: Freq $NH_2$: 3350 $cm^{-1}$.

The following compound was prepared in a similar manner to Intermediate 5(a):

(b) 4-[3-(1,2,3,4-Tetrahydro-6,7-dimethoxy-2-isoquinolinyl)propyl]benzenamine

The title compound (8.6 g) was obtained as a solid, m.p. 138°. by the reduction of Intermediate 4(b) (11 g).

INTERMEDIATE 6

(a) 1-(3-Bromopropoxy)-3-methoxy-4-nitrobenzene

A mixture of Intermediate 18 (2.4 g), 1,3-dibromopropane (7.5 ml) and potassium carbonate (2.2 g) in DMF (30 ml) was stirred at room temperature for 24 h. The mixture was filtered and the filtrate was evaporated to dryness. The residue was treated with water and extracted with dichloromethane. The organic extract was then washed with 5% sodium hydroxide solution and brine, dried and concentrated in vacuo to give the title compound (3.5 g) as an oil.

NMR includes d 2.3 (2H,m,$CH_2$), 3.6 (2H,t,$CH_2Br$), 3.8 (3H,s,$OCH_3$), 4.1 (2H,t, $CH_2O$).

The following compounds were prepared in a similar manner to Intermediate 6(a):

(b) 1-(3-Bromopropoxy)-3-methyl-4-nitrobenzene

The title compound (33 g) was obtained as an oil from 3-methyl-4-nitrophenol (25 g) and 1,3-dibromopropane (83 ml).

NMR includes d 2.3 (2H,m,$CH_2$), 2.5 (3H,s,$CH_3$), 3.6 (2H,t,$CH_2Br$), 4.1 (2H,t,$OCH_2$).

(c) 1-(3-Bromopropoxy)-3-ethyl-4-nitrobenzene

The title compound was obtained from 3-ethyl-4-nitrophenol and 1,3-dibromopropane. NMR includes d 1.23 (t,3H,$\underline{CH_3}$—$CH_2$—), 2.2 (m,2H,$CH_2$—$\underline{CH_2}$—$CH_2$), 2.8 (q,2H,$\underline{CH_2}$—$CH_3$), 3.5 (t,2H,$CH_2Br$), 4.1 (t,2H,O—$\underline{CH_2}$—), 6.6 (m,2H,Ar), 7.8 (d,2H,Ar).

INTERMEDIATE 7

(a) 1,2,3,4-Tetrahydro-6,7-dimethoxy-2-[3-(3-methoxy-4-nitrophenoxy)propyl]isoquinoline A mixture of Intermediate 6(a) (0.7 g), 1,2,3,4-tetrahydro-6,7-dimethoxyisoquinoline (0.4 g) and potassium carbonate (0.36 g) in DMF (25 ml) was heated at 60° for 16 h. The mixture was filtered and the filtrate was evaporated. The residue was treated with water and extracted with dichloromethane. The organic layer was dried, concentrated, and the resultant residue was purified by column chromatography eluting with dichloromethane:methanol (99:1) to give the title compound (0.64 g) as an oil.

NMR includes d 3.8 (9H,2s, 3×$OCH_3$).

The following compound was prepared in a similar manner to Intermediate 7(a):

(b) 1,2,3,4-Tetrahydro-6,7-dimethoxy-2-[3-(3-methyl-4-nitrophenoxy)propyl]isoquinoline The title compound (5.3 g) was obtained as an oil from Intermediate 6(b) (5.7 g) and 1,2,3,4- tetrahydro-6,7-dimethoxyisoquinoline (4.0 g).

NMR includes d 2.5 (3H,s,$CH_3$), 3.8 (6H,s, 2×$OCH_3$)

INTERMEDIATE 8

(a) 2-Methoxy-4-[3-(1,2,3,4-tetrahydro-6,7-dimethoxy-2-isoquinolinyl)propoxy]benzenamine A solution of Intermediate 7(a) (0.64 g) in ethanol (25 ml) was hydrogenated at room temperature and atmospheric pressure in the presence of 10% palladium on carbon (60 mg). After hydrogen absorption was completed, the catalyst was filtered off and the solution was concentrated in vacuo to give the title compound (0.4 g) as a solid.

NMR includes d 3.8 (9H,s, 3×$OCH_3$), 3.0 (2H,bs,$NH_2$).

The following compound was prepared in a similar manner to Intermediate 8(a):

(b) 2-Methyl-4-[3-(1,2,3,4-tetrahydro-6,7-dimethoxy-2-isoquinolinyl)propoxy]benzenamine The title compound (4.8 g) was obtained as an oil (which subsequently crystallised) from Intermediate 7(b) (5.3 g). NMR includes d 2.1 (3H,s,$CH_3$), 3.8 (6H, s, 2×$OCH_3$).

INTERMEDIATE 9

(a) 3-Methyl-4-nitrobenzeneacetic acid

3-Methyl-4-nitrobenzoyl chloride (10 g) in ether (100 ml) was added dropwise to a solution of diazomethane (prepared from 30 g of N-methyl-N-nitroso-p-toluene sulphonamide) at 0°. The reaction mixture was stirred at room temperature for 3 h and then concentrated in vacuo to give the diazo ketone as a solid. This diazo ketone in dioxan (100 ml) was then added dropwise to a solution of silver oxide in water (prepared from silver nitrate (20 g) and dilute sodium hydroxide (100 ml)). The mixture was stirred at 75°–800° for 3.5 h and filtered. The filtrate was diluted with water, acidified with a solution of nitric acid and the product was extracted with hot diisopropyl ether, treated with brine and concentrated in vacuo to give the title compound (6 g) as a solid, m.p. 95°

In the same way, the following compound was prepared:

(b) 3-Methoxy-4-nitrobenzeneacetic acid, m.p. 130°–131°.

From 3-methoxy-4-nitrobenzoyl chloride.

INTERMEDIATE 10

Ethyl 3-(3-hydroxy-4-nitrophenyl)-2-propenoate

To a solution of 3-hydroxy-4-nitrobenzaldehyde (5 g) in toluene (50 ml) was added carbethoxymethylenetriphenylphosphorane (8.96 g), and the mixture was heated under reflux for 2 h. The mixture was then concentrated and the residue was purified by column chromatography eluting with cyclohexane:ethyl acetate (6:4) to give the title compound. (6.2 g) as a solid, m.p. 95°.

INTERMEDIATE 11

Ethyl 3-(3-methoxy-4-nitrophenyl)-2-propenoate

To a solution of Intermediate 10 (5.88 g) in DMF (50 ml) was added potassium carbonate (4.4 g) and methyl iodide (4 ml). The mixture was stirred at room temperature for 2 h and then concentrated in vacuo. The residue was treated with water and extracted with dichloromethane. The organic extract was dried and concentrated to give the title compound (6.2 g) as a solid, m.p. 130°.

INTERMEDIATE 12

3-(3-Methoxy-4-nitrophenyl)-2-propenoic acid

To a suspension of Intermediate 11 (6.2 g) in ethanol (50 ml) was added a solution of 1N sodium hydroxide (50 ml). The mixture was heated under reflux for 1 h and then poured onto cracked ice. A solution of 1N hydrochloric acid (60 ml) was added and the precipitate was filtered off to give the title compound (4 g) as a solid. NMR (DMSO-$d_6$) includes d 3.95 (3H,s,OCH$_3$).

INTERMEDIATE 13

3-(3-Ethoxy-4-nitrophenyl)-2-propenoic acid

Using reactions similar to those described in Intermediates 11 and 12, the title compound (3.1 g) was obtained as a solid, m.p. 272°, from Intermediate 10 (4.0 g), ethyl iodide (4 ml) and potassium carbonate (2.6 g), followed by saponification of the ester function.

INTERMEDIATE 14

(a) 1,2,3,4-Tetrahydro-6,7-dimethoxy-2-[3-(3-methoxy-4-nitrophenyl)-1-oxo-2-propenyl]isoquinoline A mixture of Intermediate 12 (4.9 g) and 1-hydroxybenzotriazole (2.95 g) in DMF (100 ml) was stirred at room temperature for 10 min. 1,2,3,4-Tetrahydro-6,7 dimethoxyisoquinoline (5 g) was added, followed by dicyclohexylcarbodiimide (4.52 g) and the mixture was stirred at room temperature for 16 h and then filtered. The filtrate was concentrated in vacuo, treated with dilute hydrochloric acid, then dilute sodium hydroxide solution and extracted with dichloromethane. The organic extract was dried, concentrated in vacuo, and the residue was purified by column chromatography eluting firstly with ethyl acetate:cyclohexane (4:6), then with ethyl acetate to give the title compound which was crystallised from ethyl acetate/ether and obtained as crystals (6.5 g).

NMR includes d 3.85 (6H,s, 2×OCH$_3$), 3.95 (3H,s, OCH$_3$).

The following compounds were prepared in a similar manner to Intermediate 14(a):

(b) 2-[3-(3-Ethoxy-4-nitrophenyl)-1-oxo-2-propenyl]-1,2,3,4-tetrahydro-6,7-dimethoxyisoquinoline The title compound (5.3 g) was obtained as a solid, m.p. 152° from Intermediate 13 (3.0 g) and 1,2,3,4-tetrahydro-6,7-dimethoxyisoquinoline (2.5 g).

(c) 1,2,3,4-Tetrahydro-6,7-dimethoxy-2-[(3-methyl-4-nitrophenyl)acetyl]isoquinoline The title compound (2.8 g) was obtained as an oil from Intermediate 9(a) (1.8 g) and 1,2,3,4-tetrahydro-6,7-dimethoxy-isoquinoline (1.9 g).

IR: Freq CO: 1650 cm$^{-1}$.

INTERMEDIATE 15

(a) 2-[3-(4-Amino-3-methoxyphenyl)-1-oxopropyl]-1,2,3,4-tetrahydro-6,7-dimethoxyisoquinoline A solution of Intermediate 14(a) (6.5 g) in methanol/ethyl acetate (1:1; 100 ml) was hydrogenated at room temperature and atmospheric pressure in the presence of 10% palladium on carbon (0.3 g). After hydrogen absorption was completed, the catalyst was filtered off and the solution was concentrated in vacuo to give the title compound (6 g) as an oil.

NMR includes d 3.8 (9H,s, 3×OCH$_3$).

The following compounds were prepared in a similar manner to Intermediate 15(a):

(b) 2-[3-(4-Amino-3-ethoxyphenyl)-1-oxopropyl]-1,2,3,4-tetrahydro-6,7-dimethoxyisoquinoline The title compound (4.5 g) was obtained as an oil from Intermediate 14(b) (5.3 g).

IR: Freq CO: 1640 cm$^{-1}$ Freq NH$_2$: 3450 cm$^{-1}$.

(c) 2-[(4-Amino-3-methylphenyl)acetyl]-1,2,3,4-tetrahydro-6,7-dimethoxyisoquinoline The title compound (2.4 g) was obtained as an oil from Intermediate 14(c) (2.8 g).

IR: Freq CO: 1650 cm$^{-1}$ Freq NH$_2$: 3340–3440 cm$^{-1}$.

INTERMEDIATE 16

(a) 2-Methoxy-4-[3-(1,2,3,4-tetrahydro-6,7-dimethoxy-2-isoquinolinyl)propyl]benzenamine A solution of Intermediate 15(a) (6 g) in THF (30ml) was added dropwise to a stirred suspension of lithium aluminum hydride (1.84 g) in THF (50 ml) at room temperature, and the mixture was heated under reflux for 2 h. Water was carefully added to the cooled mixture which was then filtered. The filtrate was concentrated in vacuo, treated with water and extracted with dichloromethane. The organic layer was dried and concentrated in vacuo to give the title compound (4.2 g) as an oil.

IR: Freq NH$_2$: 3340–3440 cm$^{-1}$.

The following compounds were prepared in a similar manner to Intermediate 16(a):

(b) 2-Ethoxy-4-[3-(1,2,3,4-tetrahydro-6,7-dimethoxy-2-isoquinolinyl)propyl]benzenamine The title compound (2.5 g) was obtained as an oil from Intermediate 15(b) (4.5 g).

IR: Freq NH$_2$: 3340–3440 cm$^{-1}$.

(c) 2-Methyl-4-[2-(1,2,3,4-tetrahydro-6,7-dimethoxy-2-isoquinolinyl)ethyl]benzenamine The title compound (1.7 g) was obtained as a solid m p 105°, from Intermediate 15(c) (2.4 g).

INTERMEDIATE 17

3-Chloro 4-nitrophenol

Concentrated nitric acid (10 ml) in acetic acid (30 ml) was added dropwise to a cooled solution of 3-chlorophenol (10 g) in acetic acid (10 ml). After 1 hour at −5°, the mixture was poured onto ice, extracted with ether, dried over sodium sulfate and evaporated. The residue was then pun fled by column chromatography eluting with hexane-ethyl acetate (85:15) to give the title compound (9 g). M.p. 120°.

INTERMEDIATE 18

3-Methoxy-4-nitrophenol

A solution of Intermediate 17 (4.4 g) in methanol (15 ml) was added to a solution of sodium (5.8 g) in methanol (60 ml) and the mixture was stirred in an autoclave for 16 h at 100°. The mixture was cooled and poured onto ice and acidified with concentrated hydrochloric acid. Methanol was then evaporated in vacuo inducing the crystallisation of the title compound (3.5 g). M.p. 142°.

INTERMEDIATE 19

1-(2-Chloroethoxy)-3-methyl-4-nitrobenzene

A mixture of 3-methyl-4-nitrophenol (10 g), 1-bromo-2-chloroethane (16 ml) and sodium hydroxide (2.9 g) in water (50 ml) was stirred under reflux for 16 h. The mixture was diluted with water and the product was extracted with methylene chloride. The organic extract was dried on sodium sulfate and concentrated in vacuo to give the title compound as an oil (10.81 g) NMR includes d 2.5 (s,3H, —CH$_3$), 3.9 (t,2H,CH$_2$—O) and 4.3 (t,2H,—CH$_2$—Cl).

INTERMEDIATE 20

(a) 3,4-Dimethoxy-N-methylbenzenethanamine 3,4-Dimethoxybenzeneethanamine (100 g) was mixed with benzaldehyde (59 g), and rotoevaporated to give an oil. Methyl iodide (69 ml) was then added and the mixture was heated for 48 h at 40° and then boiled with 80% ethanol (500 ml) for 3 h. After half of the ethanol had evaporated, the solution was treated with ether (1 liter) to give a solid that was filtered, washed with ether, treated with dilute sodium hydroxide and extracted with ether to give the title compound (80 g) as an oil that was distilled under reduced pressure, b.p. 0.1 mm; 92°–95°.

(b) 3,4-Dimethoxy-N-methylbenzenemethanamine 3,4-Dimethoxybenzenemethanamine (100 g) was mixed with benzaldehyde (64 g), and rotoevaporated to give an oil. Methyl iodide (75 ml) was then added and the mixture was heated for 48 h at 40° and then boiled with 80% ethanol (800 ml) for 3 h. After half of the ethanol had evaporated, the solution was treated with ether (1 liter) to give a solid that was filtered, washed with ether, treated with dilute sodium hydroxide and extracted with ether to give the title compound (69 g) as an oil that was distilled under reduced pressure, b.p. 0.03 mm; 91°.

The following amines were prepared in a similar manner to Intermediates 20(a) and 20(b):

(c) 4-Fluoro-N-methylbenzenemethanamine as an oil; IR includes a peak at 3300 cm$^{-1}$ (NH).

From 4-fluorobenzenemethanamine and methyl iodide.

(d) 4-Methoxy-N-methylbenzenemethanamine as an oil; IR includes a peak at 3310 cm$^{-1}$ (NH).

From 4-methoxybenzenemethanamine and methyl iodide.

(e) 4-Methoxy-N-methylbenzeneethanamine as an oil: IR includes a peak at 3310 cm$^{-1}$ (NH).

From 4-methoxybenzeneethanamine and methyl iodide.

(f) 4-(Methylthio)-N-methylbenzenemethanamine as an oil; IR includes a peak at 3310 cm$^{-1}$ (NH).

From 4-(methylthio)benzenemethanamine and methyl iodide.

(g) 4-Methyl-N-Methylbenzenemethanamine as an oil: IR includes a peak at 3310 cm$^1$ (NH).

From 4-methylbenzenemethanamine and methyl iodide.

INTERMEDIATE 21

(a) 3,4-Dimethoxy-N-methyl-N-[3-(3-methyl-4-nitrophenoxy)propyl]benzenemethanamine A mixture of Intermediate 6(b) (6 g), Intermediate 20(b) (4 g) and potassium carbonate (3.3 g) in DMF (80 ml) was heated at 60° for 36 h. The mixture was filtered and the filtrate was evaporated. The residue was added to water and extracted with dichloromethane. The organic layer was washed with water, dried over sodium sulfate filtered and evaporated. The oily residue was then chromatographed with dichloromethane/methanol (99:1) to give the title compound as an oil (4.6 g). NMR includes d 2.2 (s,3H,—CH$_3$), 2.4 (s,3H,N—CH$_3$) and 3.8 (s,6H,2OCH$_3$).

In the same way, the following compounds were prepared:

(b) 3,4-Dimethoxy-N-[3-(3-methoxy-4-nitrophenoxy)propyl]-N-methylbenzenemethanamine as an oil From Intermediate 6(a) and Intermediate 20(b). NMR includes d 2.2 (s,3H,N—CH$_3$) and 3.85–3.9 (2s,3H–6H,3O-CH$_3$).

(c) 3,4-Dimethoxy-N-[3-(3-ethyl-4-nitrophenoxy)propyl]-N-methylbenzenemethanamine as an oil.

From Intermediate 6(c) and Intermediate 20(b). NMR includes d 2.2 (s,3H,N—CH$_3$) and 3.85–3.9 (s,6H,2O—CH$_3$).

(d) 3,4-Dimethoxy-N-methyl-N-[2-(3-methyl-4-nitrophenoxy)ethyl]benzenemethanamine as an oil From Intermediate 19 and Intermediate 20(b). NMR includes d 2.3 (s,3H,N—CH$_3$), 2.5 (s,3H,N—CH$_3$) and 3.8 (s,6H,2—OCH$_3$).

INTERMEDIATE 22

(a) N-[3-(4-Amino-3-methylphenoxy)propyl]-3,4-dimethoxy-N-methylbenzenemethanamine A solution of Intermediate 21(a) (4.6 g) in ethanol (100 ml) was hydrogenated at room temperature in presence of 10% palladium-on-carbon 10% (450 mg). After the hydrogen absorption was completed, the catalyst was filtered off and the solution concentrated to give the title compound (3.7 g) as an oil. NMR includes d 2.0 (s,3H,CH$_3$), 2.1 (s,3H,N—CH$_3$) and 3.7 (s,6H,2OCH$_3$).

In the same way, the following compounds were prepared:

(b) N-[3-(4-Amino-3-methoxyphenoxy)propyl]-3,4-dimethoxy-N-methylbenzenemethanamine as an oil.

From Intermediate 21(b). NMR includes d 2.2 (s,3H,N—CH$_3$),3.85–3.9 (s,3H,OCH$_3$) and 3.9 (s,6H,2OCH$_3$).

(c) N-[3-(4-Amino-3-ethylphenoxy)propyl]-3,4-dimethoxy-N-methylbenzenemethanamine as an oil.

From Intermediate 21(c). NMR includes d 2.1 (s,3H,N—CH$_3$) and 3.7 (s,6H,2OCH$_3$).

(d) N-[2-(4-Amino-3-methylphenoxy)ethyl]-3,4-dimethoxy-N-methylbenzenemethanamine as an oil.

From Intermediate 21(d). NMR includes d 2.0 (s,3H,N—CH$_3$), 2.2 (s,3H,N—CH$_3$) and 3.8 (s,6H,2OCH$_3$).

INTERMEDIATE 23

Diethyl (3-methyl-4-nitrobenzyl)malonate

To a solution of sodium ethanolate [prepared from 1.35 g Na in ethanol (30 ml)] were added diethyl malonate (9.2 ml) and then dropwise 3-methyl-4-nitrobenzyl bromide (13.4 g). The mixture was stirred 30 minutes at room temperature, then 30 minutes under reflux and then concentrated. The residue is treated with water and hexane, the precipitate filtered and the filtrate extracted with diethyl ether. The organic extract was dried on sodium sulfate and concentrate to give the title compound as an oil (4 g).

NMR includes d 1.15 (t,6H,2×CH$_3$—CH$_2$), 2.5 (s,3H, CH$_3$—Ar), 3.16 (s,2H,CH$_2$—Ar), 4.0 (q,4H,2×CH$_2$—CH$_3$), 7.0 (m,2H,Ar), 7.7 (d, 1H,Ar).

INTERMEDIATE 24

3-(3-Methyl-4-nitrophenyl)propionic acid

Intermediate 23 (4 g) was added dropwise to a solution of potassium hydroxide (3.1 g) in water and the mixture is stirred under reflux for 2 hours, diluted with water, washed with diethyl ether and then acidified with a dilute solution of hydrochloric acid. After extraction with diethyl ether and concentration, the concentrate was heated at 130° for 3 h to give the title compound as a yellow solid (2.3 g). NMR ($CDCl_3$) includes d 2.5 (s,3H,$CH_3$) and 2.9 (m,4H,$2CH_2$).

INTERMEDIATE 25

(a) N-[(3,4-Dimethoxyphenyl)methyl]-N-methyl-3-methyl-4-nitrobenzeneethanamide

A mixture of Intermediate 9(a) (2 g) and 1-hydroxybenzotriazole (1.6 g) in DMF (35 ml) was stirred at room temperature for 5 min. Intermediate 20(b) (1.9 g) in DMF (20 ml) was then added, followed by dicyclohexylcarbodiimide (2.1 g) and the mixture was stirred at room temperature for 16 h and then filtered. The filtrate was concentrated in vacuo, treated with dilute sodium hydroxide solution and extracted with dichloromethane. The combined, dried organic extracts were evaporated and the residue was purified by column chromatography eluting with dichloromethane/methanol (97:3) to give the title compound (1.7 g) as an oil. IR includes a signal at 1640 cm-1 (CO).

In the same way, the following compounds were prepared:

(b) N-[(3,4-Dimethoxyphenyl)methyl]-N-methyl-3-methoxy-4-nitrobenzeneethanamide

From Intermediate 9(b) and Intermediate 20(b). IR includes a signal at 1645 cm-1 (CO).

(c) N-[(3,4-Dimethoxyphenyl)methyl]-N-methyl-3-methyl-4-nitrobenzenepropanamide as an oil From Intermediate 24 and Intermediate 20(b). NMR ($CDCl_3$) includes d 2.5 (s,3H,—$CH_3$), 2.9 (s,3H,N—$CH_3$) and 3.8 (s,6H,$2OCH_3$).

INTERMEDIATE 26

(a) 4-Amino-3-methyl-N-[(3,4-dimethoxyphenyl)methyl]-N-methylbenzeneethanamide

A solution of Intermediate 25(a) (1.7 g) in ethanol (60 ml) was hydrogenated at room temperature in presence of 10% palladium-on-carbon (0.25 g). After the hydrogen absorption was completed the catalyst was filtered off and the solution concentrated to give the title compound (1.4 g) as an oil. IR includes signals at 3450–3350 cm-1 ($NH_2$) and 1630 cm-1 (CO).

In the same way, the following compounds were prepared:

(b) 4-Amino-3-methoxy-N-[(3,4-dimethoxyphenyl)methyl]-N-methylbenzeneethanamide

From Intermediate 25(b). IR includes signals at 3450–3350 cm-1 ($NH_2$) and 1625 cm-1 (CO).

(c) 4-Amino-3-methyl-N-[(3,4-dimethoxyphenyl)methyl]-N-methylbenzenepropanamide

From Intermediate 25(c). NMR includes d 2.1 (3H,s,$CH_3$), 2.75 (3H,s,N—$CH_3$) and 3.8 (6H,s,$2OCH_3$).

INTERMEDIATE 27

(a) 4-Amino-3-methyl-N-[(3,4-dimethoxyphenyl)methyl]-N-methylbenzeneethanamine

A solution of Intermediate 26(a) (1.4 g) in THF (50 ml) was added dropwise to a stirred suspension of lithium aluminium hydride (0.7 g) in THF (30 ml) at room temperature and the mixture was heated under reflux for 3 h. Water was added carefully to the cooled mixture which was then filtered on a celite pad, washed with THF, evaporated and extracted with ether. The ethereal extracts were dried and evaporated to give the title compound (1 g) as an oil. IR includes a signal at 3450–3350 cm-1 ($NH_2$).

In the same way, the following compounds were prepared:

(b) 4-Amino-3-methoxy-N-[(3,4-dimethoxyphenyl)methyl]-N-methylbenzeneethanamine

From Intermediate 26(b). IR includes a signal at 3455–3345 cm-1 ($NH_2$).

(c) 4-Amino-3-methyl-N-[(3,4-dimethoxyphenyl)methyl]-N-methylbenzenepropanamine as an oil From Intermediate 26(c). NMR includes d 2.0 (3H,s,—$CH_3$), 2.1 (3H,s,N—$CH_3$) and 3.8 (6H,s,$2OCH_3$).

INTERMEDIATE 28

N-[(3,4-Dimethoxyphenyl)methyl]-N-methyl-3-methoxy-4-nitrobenzene-2-propenamide

A mixture of Intermediate 12 (3 g) and 1-hydroxybenzotriazole (1.95 g) in DMF (100 ml) was stirred at room temperature for 10 minutes. Intermediate 20(b) (2.5 g) was added, followed by dicyclohexylcarbodiimide (2.95 g) and the mixture was stirred at room temperature for 16 h and then filtered. The filtrate was concentrated in vacuo, treated with dilute hydrochloric acid solution, then dilute sodium hydroxide solution and extracted with methylene chloride. The organic extract was dried with sodium sulfate and concentrated. The residue was purified by column chromatography eluting with ethyl acetate to give the title compound (4.4 g).

NMR includes d 2.9 (3H,s,N—$CH_3$), 3.85 (3H,s,$OCH_3$) and 3.9 (6H,s,$2OCH_3$).

INTERMEDIATE 29

4-Amino-3-methoxy-N-[(3,4-dimethoxyphenyl)methyl]-N-methylbenzenepropanamide

A solution of Intermediate 28 (8.4 g) in methanol/ethyl acetate (1:1, 100 ml) was hydrogenated at room temperature in presence of 10% palladium-on-carbon (0.3 g). After the hydrogen absorption was completed, the catalyst was filtered off and the solution concentrated to give the title compound (7.3 g) as an oil. IR includes signals at 3450–3350 cm-1 ($NH_2$) and 1635 cm-1 (CO).

INTERMEDIATE 30

4-Amino-3-methoxy-N-[(3,4-dimethoxyphenyl)methyl]-N-methylbenzenepropanamine

A solution of Intermediate 29 (7.32 g) in tetrahydrofuran (100 ml) was added dropwise to a stirred suspension of lithium aluminium hydride (2.3 g) in tetrahydrofuran (100 ml) at room temperature and the mixture was heated under reflux 1 h. Water (20 ml) was added carefully to the cooled mixture which was filtered on a celite pad, washed with diethyl ether, concentrated and extracted with methylene chloride. The organic extract was dried on sodium sulfate, evaporated and the product purified by column chromatography on silica gel eluting with dichloromethane/methanol (95:5) to give the title compound as an oil (2.5 g). IR includes a signal at 3440–3340 cm-1 ($NH_2$).

INTERMEDIATE 31

(a) N-[(3,4-Dimethoxyphenyl)methyl]-N-methyl-4-nitrobenzenebutanamide

A mixture of 4-nitrobenzenebutanoic acid (31 g) and thionyl chloride (200 ml) was heated under reflux for 1 h. The solution was then concentrated and coevaporated with benzene to give an oil. This oil was dissolved in acetone (100 ml) and added dropwise to a stirred mixture of Intermediate 20(b) (28.6 g) and sodium hydrogen carbonate (35 g) in acetone (150 ml) at room temperature. Stirring was continued for 4 h, the mixture was then filtered and the filtrate was concentrated. The residue was poured into water and then extracted with dichloromethane. The organic phase was evaporated to give the title compound (41.5 g) as an oil. Recrystallisation from ethanol gave the title compound as a solid, MP: 90°.

(b) N-[(3,4-Dimethoxyphenyl)methyl]-N-methyl-4-nitrobenzeneethanamide

A mixture of 4-nitrobenzeneacetic acid (22 g) and thionyl chloride (200 ml) was heated under reflux for 3 h. The solution was concentrated and then coevaporated with benzene to give an oil. This oil was dissolved in acetone (100 ml) and added dropwise to a stirred mixture of Intermediate 20(b) (22 g) and sodium hydrogen carbonate (15.3 g) in acetone (100 ml) at room temperature. Stirring was continued for 6 hours, the mixture was then filtered and the filtrate was concentrated. The residue was poured into water and extracted with ethyl acetate. The organic phase was washed first with dilute sodium hydroxide solution, then with water, dried and concentrated to give the title compound (22.3 g) as an oil. IR includes a peak at 1650cm-1 (CO).

The following amides were prepared in a similar manner to Intermediates 31(a) and 31(b):

(c) N-[2-(3,4-Dimethoxyphenyl)ethyl]-N-methyl-4-nitrobenzenebutanamide as an oil; IR includes a peak at 1640 $cm^{-1}$ (CO).

From 4-nitrobenzenebutanoic acid and Intermediate 20(a).

(d) N-[2-(3,4-Dimethoxyphenyl)ethyl]-N-methyl-4-nitrobenzenepropanamide as an oil; IR includes a peak at 1640 $cm^{-1}$ (CO).

From 4-nitrobenzenepropanoic acid and Intermediate 20(a).

(e) N-[2-(3,4-Dimethoxyphenyl)ethyl]-N-methyl-4-nitrobenzeneethanamide as an oil; IR includes a peak at 1650 $cm^{-1}$ (CO).

From 4-nitrobenzeneacetic acid and Intermediate 20(a).

(f) N-[(3,4-Dimethoxyphenyl)methyl]-N-methyl-4-nitrobenzenepropanamide as an oil; IR includes a peak at 1640 $cm^{-1}$ (CO).

From 4-nitrobenzenepropanoic acid and Intermediate 20(b).

(g) N-[(4-Methoxyphenyl)methyl]-N-methyl-4-nitrobenzenepropanamide as an oil; IR includes a peak at 1640 $cm^{-1}$ (CO).

From 4-nitrobenzenepropanoic acid and Intermediate 20(d).

(h) N-[2-(4-Methoxyphenyl)ethyl]-N-methyl-4-nitrobenzenebutanamide as an oil; IR includes a peak at 1650 $cm^{-1}$ (CO).

From 4-nitrobenzenebutanoic acid and Intermediate 20(e).

(i) N-[(4-Fluorophenyl)methyl]-N-methyl-4-nitrobenzenebutanamide as an oil; IR includes a peak at 1640 $cm^{-1}$ (CO).

From 4-nitrobenzenebutanoic acid and Intermediate 20(c).

(j) N-[[4-(Methylthio)phenyl]methyl]-N-methyl-4-nitrobenzenebutanamide as an oil: IR includes a peak at 1640 $cm^{-1}$ (CO).

From 4-nitrobenzenebutanoic acid and Intermediate 20(f).

(k) N-[2-(4-Methoxyphenyl)ethyl]-N-methyl-4-nitrobenzeneethanamide as an oil; IR includes a peak at 1650 $cm^{-1}$ (CO).

From 4-nitrobenzeneacetic acid and Intermediate 20(e).

(l) N-[(3,4-Dimethoxyphenyl)methyl]-N-methyl-4-nitrobenzenepentanamide as an oil; IR includes a peak at 1650 $cm^{-1}$ (CO).

From 4-nitrobenzenepentanoic acid and Intermediate 20(b).

INTERMEDIATE 32

(a) 4-Amino-N-[(3,4-dimethoxyphenyl)methyl]-N-methylbenzenebutanamide

Intermediate 31 (a) (40 g) was dissolved in a mixture of methanol (300 ml) and concentrated hydrochloric acid (160 ml) at room temperature with stirring. Iron powder (21 g) was then added slowly, and the reaction mixture was heated under reflux for 1 h. The mixture was then evaporated and basified with sodium hydroxide solution. Ethyl acetate (1 liter) was added and the mixture was filtered. The organic phase was washed with water, dried and evaporated to give the title compound (30 g) as an oil. IR includes peaks at 1630 $cm^{-1}$ (CO), 3350–3430 cm-1 ($NH_2$).

(b) 4-Amino-N-[(3,4-dimethoxyphenyl)methyl]-N-methylbenzeneethanamide

Intermediate 31(b) (22 g) was dissolved in a mixture of methanol (300 ml) and concentrated hydrochloric acid (150 ml) at room temperature with stirring. Iron powder (18 g) was then added slowly, and the reaction mixture was heated under reflux for 3 h. The mixture was then evaporated, basified with sodium hydroxide solution, and extracted with ethyl acetate. The organic phase was washed with water, dried and evaporated to give the title compound (14 g) as an oil. IR includes peaks at 1620 cm-1 (CO) and 335–3450 cm-1 ($NH_2$).

The following compounds were prepared in a similar manner to Intermediates 32(a) and 32(b):

(c) 4-Amino-N-[2-(3,4-dimethoxyphenyl)ethyl]-N-methylbenzenebutanamide as an oil; IR includes peaks at 1630 $cm^{-1}$ (CO) and 3330–3420 $cm^{-1}$ ($NH_2$).

From Intermediate 31(c).

(d) 4-Amino-N-[2-(3,4-dimethoxyphenyl)ethyl]-N-methylbenzenepropanamide as an oil; IR includes peaks at 1630 $cm^{-1}$ (CO) and 3340–3420 $cm^{-1}$ ($NH_2$).

From Intermediate 31(d).

(e) 4-Amino-N-[2-(3,4-dimethoxyphenyl)ethyl]-N-methylbenzeneethanamide as an oil: IR includes peaks at 1640 $cm^{-1}$ (CO) and 3330–3420 $cm^{-1}$ ($NH_2$).

From Intermediate 31(e).

(f) 4-Amino-N-[(3,4-dimethoxyphenyl)methyl]-N-methylbenzenepropanamide as an oil; IR includes peaks at 1640 $cm^{-1}$ (CO) and 3350–3440 $cm^{-1}$ ($NH_2$).

From Intermediate 31(f).

(g) 4-Amino-N-[(4-methoxyphenyl)methyl]-N-methylbenzenepropanamide as an oil: IR includes peaks at 1650 cm$^{-1}$ (CO) and 3330–3420 cm$^{-1}$ (NH$_2$).

From Intermediate 31(g).

(h) 4-Amino-N-[2-(4-methoxyphenyl)ethyl]-N-methylbenzenebutanamide as an oil; IR includes peaks at 1640 cm$^{-1}$ (CO) and 3340–3430 cm$^{-1}$ (NH$_2$).

From Intermediate 31(h).

(i) 4-Amino-N-[(4-fluorophenyl)methyl]-N-methylbenzenebutanamide as an oil; IR includes peaks at 1640 cm$^{-1}$ (CO) and 3340–3430 cm$^{-1}$ (NH$_2$).

From Intermediate 31(i).

(j) 4-Amino-N-[[4-(methylthio)phenyl]methyl]-N-methylbenzenebutanamide as an oil: IR includes peaks at 1640 cm$^{-1}$ (CO) and 3340–3430 cm$^{-1}$ (NH$_2$).

From Intermediate 31(j).

(k) 4-Amino-N-[2-(4-methoxyphenyl)ethyl]-N-methylbenzeneethanamide as an oil; IR includes peaks at 1635 cm$^{-1}$ (CO) and 3340–3440 cm$^{-1}$ (NH$_2$).

From Intermediate 31(k).

(l) 4-Amino-N-[(3,4-dimethoxyphenyl)methyl]-N-methylbenzenepentanamide as an oil: IR includes peaks at 1630 cm$^{-1}$ (CO) and 3340–3420 cm$^{-1}$ (NH$_2$).

From Intermediate 31(l).

INTERMEDIATE 33

(a) 4-Amino-N-[(3,4-dimethoxyphenyl)methyl]-N-methylbenzenebutanamine

A solution of Intermediate 32(a) (30 g) in THF (150 ml) was added dropwise to a stirred suspension of lithium aluminium hydride (10 g) in THF (150 ml) at room temperature and the mixture was heated under reflux for 3 h. Water was added carefully to the cooled mixture, which was then filtered, washed with THF, evaporated, and extracted with ether. The combined ethereal extracts were dried and evaporated to give the title compound (21 g) as an oil. IR includes a peak at 3370–3440 cm-1 (NH$_2$).

(b) 4-Amino-N-[(3,4-dimethoxyphenyl)methyl]-N-methylbenzeneethanamine

A solution of Intermediate 32(b) (14 g) in THF (100 ml) was added dropwise to a stirred suspension of lithium aluminium hydride (8 g) in THF (100 ml) at room temperature and the mixture was heated under reflux for 3 hours. Water was added carefully to the cooled mixture which was then filtered, washed with THF, evaporated and extracted with ether. The combined ethereal extracts were dried and evaporated to give the title compound (9.5 g) as an oil. IR includes a peak at 3360–3430 cm-1 (NH$_2$).

The following compounds were prepared in a similar manner to Intermediates 33(a) and 33(b):

(c) 4-Amino-N-[2-(3,4-dimethoxyphenyl)ethyl]-N-methylbenzenebutanamine as an oil: IR includes a peak at 3360–3430 cm$^{-1}$ (NH$_2$).

From Intermediate 32(c).

(d) 4-Amino-N-[2-(3,4-dimethoxyphenyl)ethyl]-N-methylbenzenepropanamine as an oil: IR includes a peak at 3360–3460 cm$^{-1}$ (NH$_2$).

From Intermediate 32(d).

(e) 4-Amino-N-[2-(3,4-dimethoxyphenyl)ethyl]-N-methylbenzeneethanamine as an oil; IR includes a peak at 3360–3430 cm$^{-1}$ (NH$_2$).

From Intermediate 32(e).

(f) 4-Amino-N-[(3,4-dimethoxyphenyl)methyl]-N-methylbenzenepropanamine as an oil; IR includes a peak at 3360–3440 cm$^{-1}$ (NH$_2$).

From Intermediate 32(f).

(g) 4-Amino-N-[(4-methoxyphenyl)methyl]-N-methylbenzenepropanamine as an oil; IR includes a peak at 3360–3430 cm$^{-1}$ (NH$_2$).

From Intermediate 32(g).

(h) 4-Amino-N-[2-(4-methoxyphenyl)ethyl]-N-methylbenzenebutanamine as an oil; IR includes a peak at 3380–3460 cm$^{-1}$ (NH$_2$).

From Intermediate 32(h).

(i) 4-Amino-N-[(4-fluorophenyl)methyl]-N-methylbenzenebutanamine as an oil; IR includes a peak at 3350–3430 cm$^{-1}$ (NH$_2$).

From Intermediate 32(i).

(j) 4-Amino-N-[[4-(methylthio)phenyl]methyl]-N-methylbenzenebutanamine as an oil: IR includes a peak at 3350–3430 cm$^{-1}$ (NH$_2$).

From Intermediate 32(j).

(k) 4-Amino-N-[2-(4-methoxyphenyl)ethyl]-N-methylbenzeneethanamine as an oil; IR includes a peak at 3360–3440 cm$^{-1}$ (NH$_2$).

From Intermediate 32(k).

(l) 4-Amino-N-[(3,4-dimethoxyphenyl)methyl]-N-methylbenzenepentanamine as an oil; IR includes a peak at 3360–3440 cm$^{-1}$ (NH$_2$).

From Intermediate 32(l).

INTERMEDIATE 34

(a) N-[2-(3,4-Dimethoxyphenyl)ethyl]-N-methyl-2-(4-nitrophenoxy)acetamide

A mixture of (4-nitrophenoxy)acetic acid (51 g) and thionyl chloride was heated under reflux for 2 h. The solution was concentrated and then coevaporated with benzene to give a solid. This solid was dissolved in acetone (250 ml) and added dropwise to a stirred mixture of Intermediate 20(a) (50 g) and sodium hydrogen carbonate (22 g) in acetone (250 ml) at room temperature. Stirring was continued for 4 h, the mixture was then filtered and the filtrate was concentrated. The residue was treated with water and extracted with ethyl acetate. The organic phase was washed first with dilute sodium hydroxide, then with water, dried and concentrated. Recrystallisation from ethanol gave the title compound (82 g). MP 121°.

The following compounds were prepared in a similar manner to Intermediate 34(a):

(b) N-[(3,4-Dimethoxyphenyl)methyl]-N-methyl-2-(4-nitrophenoxy)acetamide. MP 130°

From (4-nitrophenoxy)acetic acid and Intermediate 20(b).

(c) N -Methyl-2-(4-nitrophenoxy)-N-(phenylmethyl)acetamide. MP 98°.

From (4-nitrophenoxy)acetic acid and N-methylbenzenemethanamine.

(d) N-[(3,4-Dimethoxyphenyl)methyl]-N-methyl-2-(4-nitrophenylthio)acetamide as an oil. NMR includes signals at d 3.0 (3H,s,N—CH$_3$) and 3.8 (6H,s,OCH$_3$).

From (4-nitrophenylthio)acetic acid and Intermediate 20(b).

(e) N-[2-(4-Methoxyphenyl)ethyl]-N-methyl-2-(4-nitrophenoxy)acetamide. MP 107°.

From (4-nitrophenoxy)acetic acid and Intermediate 20(e).

(f) N-[(4-Methoxyphenyl)methyl]-N-methyl-2-(4-nitrophenoxy)acetamide. MP 120°.

From (4-nitrophenoxy)acetic acid and Intermediate 20(d).

(g) N-Methyl-N-[(4-methylphenyl)methyl]-2-(4-nitrophenoxy)acetamide. MP 126°.

From (4-nitrophenoxy)acetic acid and Intermediate 20(g).

(h) N-Methyl-N-[[4-(methylthio)phenyl]methyl]-2-(4-nitrophenoxy) acetamide. MP 122°.

From (4-nitrophenoxy)acetic acid and Intermediate 20(f).

(i) N-Ethyl-2-(4-nitrophenoxy)-N-(phenylmethyl)acetamide as an oil; IR includes a peak at 1655 cm$^{-1}$ (CO).

From (4-nitrophenoxy)acetic acid and N-ethylbenzenemethanamine.

INTERMEDIATE 35

(a) 2-(4-Aminophenoxy)-N-[2-(3,4-dimethoxyphenyl)ethyl]-N-methylacetamide

A solution of Intermediate 34(a) (37.5 g) in ethanol (350 ml) was hydrogenated at room temperature in the presence of 10% palladium on carbon (3.5 g). After hydrogen absorption was completed, the catalyst was filtered off and the solution was concentrated to give the title compound (34 g) as an oil. IR includes peaks at 1650 cm$^{-1}$ (CO) and 3340–3400 cm$^{-1}$ (NH$_2$).

The following compounds were prepared in a similar manner to Intermediate 35(a):

(b) 2-(4-Aminophenoxy)-N-[(3,4-dimethoxyphenyl)methyl]-N-methylacetamide as an oil. IR includes peaks at 1650 cm$^{-1}$ (CO) and 3340–3400 cm$^{-1}$ (NH$_2$).

From Intermediate 34(b).

(c) 2-(4-Aminophenoxy)-N-methyl-N-(phenylmethyl)acetamide as an oil. IR includes peaks at 1660 cm$^{-1}$ (CO) and 3300–3420 cm$^{-1}$ (NH$_2$).

From Intermediate 34(c).

(d) 2-(4-Aminophenylthio)-N-[(3,4-dimethoxyphenyl)methyl]-N-methyl acetamide as an oil. IR includes peaks at 1645 cm$^{-1}$ (CO) and 3350 cm$^{-1}$ (NH$_2$).

From Intermediate 34(d).

(e) 2-(4-Aminophenoxy)-N-[2-(4-methoxyphenyl)ethyl]-N-methylacetamide as an oil. IR includes peaks at 1630 cm$^{-1}$ (CO) and 3350–3420 cm$^{-1}$ (NH$_2$).

From Intermediate 34(e).

(f) 2-(4-Aminophenoxy)-N-[(4-methoxyphenyl)methyl]-N-methylacetamide as an oil. IR includes peaks at 1650 cm$^{-1}$ (CO) and 3340–3430 cm$^{-1}$ (NH$_2$).

From Intermediate 34(f).

(g) 2-(4-Aminophenoxy)-N-methyl-N-[(4-methylphenyl)methyl]acetamide as an oil. IR includes peaks at 1650 cm$^{-1}$ (CO) and 3350–3420 cm$^{-1}$ (NH$_2$).

From Intermediate 34(g).

(h) 2-(4-Aminophenoxy)-N-methyl-N-[[4-(methylthio)phenyl]methyl]acetamide as an oil. IR includes peaks at 1660 cm$^{-1}$ (CO) and 3340–3420 cm$^{-1}$ (NH$_2$).

From Intermediate 34(h).

(i) 2-(4-Aminophenoxy)-N-ethyl-N-(phenylmethyl)acetamide as an oil. IR includes peaks at 1650 cm$^{-1}$ (CO) and 3350–3430 cm$^{-1}$ (NH$_2$).

From Intermediate 34(i).

INTERMEDIATE 36

(a) N-[2-(4-Aminophenoxy)ethyl]-3,4-dimethoxy-N-methylbenzeneethanamine

A solution of Intermediate 35(a) (20 g) in THF (200 ml) was added dropwise to a stirred suspension of lithium aluminium hydride in THF (100 ml) at room temperature and the mixture was heated under reflux for 3 h. Water was added carefully to the cooled mixture which was then filtered, washed with THF, evaporated and extracted with ether. The combined ethereal extracts were dried and evaporated to give the title compound (11 g) as an oil. IR includes a peak at 3350–3430 cm-1 (NH$_2$).

The following compounds were prepared in a similar manner to Intermediate 36(a):

(b) N-[2-(4-Aminophenoxy)ethyl]-3,4-dimethoxy-N-methylbenzenemethanamine as an oil. IR includes a peak at 3360–3420 cm$^{-1}$ (NH$_2$).

From Intermediate 35(b).

(c) N-[2-(4-Aminophenoxy)ethyl]-N-methylbenzenemethanamine as an oil. IR includes a peak at 3330–3420 cm$^{-1}$ (NH$_2$).

From Intermediate 35(c).

(d) N-[2-(4-Aminophenylthio)ethyl]-3,4-dimethoxy-N-methylbenzenemethanamine as an oil. NMR includes signals at d 2.30 (3H,s,N—CH$_3$) and 3.85 (6H,s,OCH$_3$).

From Intermediate 35(d).

(e) N-[2-(4-Aminophenoxy)ethyl]-4-methoxy-N-methylbenzeneethanamine as an oil. IR includes a peak at 3340–3430 cm$^{-1}$ (NH$_2$).

From Intermediate 35(e).

(f) N-[2-(4-Aminophenoxy)ethyl]-4-methoxy-N-methylbenzenemethanamine as an oil. IR includes a peak at 3350–3430 cm$^{-1}$ (NH$_2$).

From Intermediate 35(f).

(g) N-[2-(4-Aminophenoxy)ethyl]-4-methyl-N-methylbenzenemethanamine as an oil. IR includes a peak at 3350–3430 cm$^{-1}$ (NH$_2$).

From Intermediate 35(g).

(h) N-[2-(4-Aminophenoxy)ethyl]-N-methyl-4-(methylthio)benzenemethanamine as an oil. IR includes a peak at 3350–3420 cm$^{-1}$ (NH$_2$).

From Intermediate 35(h).

(i) N-[2-(4-Aminophenoxy)ethyl]-N-ethylbenzenemethanamine as an oil. IR includes a peak at 3360–3430 cm$^{-1}$ (NH$_2$).

From Intermediate 35(i).

INTERMEDIATE 37

(a) 3,4-Dimethoxy-N-methyl-N-[3-(4-nitrophenoxy)propyl]benzeneethanamine

A mixture of 1-(3-bromopropoxy)-4-nitrobenzene (18.7 g) and Intermediate 20(a) (14.1 g) were heated for 30 min at 140° and then diluted with water. The mixture was extracted with dichloromethane, and the organic phase was washed with water, dried and concentrated. The residue was purified by column chromatography eluting with dichloromethane/methanol (95:5) to give the title compound (18 g) as an oil. NMR includes a signal at d 2.38 (3H,s,N—CH$_3$).

The following compounds were prepared in a similar manner to Intermediate 37(a):

(b) 4-Methoxy-N-methyl-N-[3-(4-nitrophenoxy)propyl]benzeneethanamine as an oil. NMR includes a signal at d 2.40 (3H,s,N—CH$_3$).

From 1-(3-bromopropoxy)-4-nitrobenzene and Intermediate 20(e).

(c) 3,4-Dimethoxy-N-methyl-N-[3-(4-nitrophenoxy)propyl]benzenemethanamine as an oil. NMR includes a signal at d 2.40 (3H,s,N—CH₃).

From 1-(3-bromopropoxy)-4-nitrobenzene and Intermediate 20(b).

(d) 3,4-Dimethoxy-N-methyl-N-[3-[(4-nitrophenyl)thio]propyl]benzenemethanamine as an oil. NMR includes a signal at d 2.40 (3H,s,N—CH₃).

From 1-[(3-bromopropyl)thio]-4-nitrobenzene and Intermediate 20(b).

INTERMEDIATE 38

(a) N-[3-(4-Aminophenoxy)propyl]-3,4-dimethoxy-N-methylbenzeneethanamine

A solution of Intermediate 37(a) (18 g) in ethanol (200 ml) was hydrogenated at room temperature in the presence of 10% palladium on carbon (1 g). After hydrogen absorption was completed, the catalyst was filtered off and the solution was concentrated to give the title compound (15 g) as an oil. IR includes a peak at 3300–3370 cm-1 (NH₂).

The following compounds were prepared in a similar manner to Intermediate 38(a):

(b) N-[3-(4-Aminophenoxy)propyl]-4-methoxy-N-methylbenzeneethanamine as an oil. IR includes a peak at 3350–3430 cm$^{-1}$ (NH₂).

From Intermediate 37(b).

(c) N-[3-(4-Aminophenoxy)propyl]-3,4-dimethoxy-N-methylbenzenemethanamine as an oil. IR includes a peak at 3360–3430 cm$^{-1}$ (NH₂).

From Intermediate 37(c).

(d) N-[3-[(4-Aminophenyl)thio]propyl]-3,4-dimethoxy-N-methylbenzenemethanamine as an oil. IR includes a peak at 3370–3450 cm$^{-1}$ (NH₂).

From Intermediate 37(d).

INTERMEDIATE 39

9,10-Dihydro-2-(methylthio)-9-oxo-4-acridinecarboxylic acid (i) 2-[(2-Carboxyphenyl)amino]-5-(methylthio)benzoic acid A mixture of 2-chloro-5-(methylthio)benzoic acid (10 g), anthranilic acid (7 g), potassium carbonate (14 g) and copper (1 g) in 2-(2-methoxyethoxy)ethanol (100 ml) was heated at 180° for 24 h. Water (400 ml) was then added, and the catalyst was filtered off. The filtrate was acidified with dilute hydrochloric acid. The resulting precipitate was filtered off, washed with water, dried, and crystallised from methanol to give the title compound (4.5 g) as crystals. IR includes peaks at 3300 cm-1 (NH) and 1700 cm-1 (CO₂H).

(ii) 9,10-Dihydro-2-(methylthio)-9-oxo-4-acridinecarboxylic acid

The product of part (i) above (2 g) in phosphorus oxychloride (6 ml) was heated at reflux for 1 h. The solution was then cooled (to 0°), and water (15 ml) was added slowly. The mixture was then heated at 100° for 10 min and then poured onto cracked ice. The resulting precipitate was filtered off, washed with water, and crystallised from methanol to give the title compound (1.6 g). IR includes peaks at 1690 cm-1 (CO₂H) and 1620 cm-1 (CO).

INTERMEDIATE 40

N-[4-(3-Bromopropoxy)phenyl]-9,10-dihydro-9-oxo-4-acridinecarboxamide (i) N-[4-(3-Bromopropoxy)phenyl]acetamide A mixture of N-(4-hydroxyphenyl)acetamide (10 g) and potassium carbonate (11 g) in DMF (200 ml) was stirred for 20 min at room temperature. 1,3-Dibromopropane (35 ml) was then added and stirring was continued for 4 h. The mixture was filtered and the filtrate was concentrated in vacuo. The residue was treated with water and extracted with dichloromethane. The organic phase was washed first with dilute sodium hydroxide, then with water, dried and concentrated to give a solid which was triturated with hexane to give the title compound (14 g), MP: 120°.

(ii) 4-(3-Bromopropoxy)benzenamine

A mixture of the product of part (i) above (13 g) and 5N hydrochloric acid (200 ml) was heated under reflux for 2 h. After cooling, the mixture was basified with sodium hydroxide solution and extracted with dichloromethane. The organic phase was evaporated to give the title compound (7 g) as an oil. IR includes a peak at 3360–3450 cm-1 (NH).

(iii) N-[4-(3-Bromopropoxy)phenyl]-9,10-dihydro-9-oxo-4-acridinecarboxamide

A mixture of 9,10-dihydro-9-oxo-4-acridinecarboxylic acid (1.5 g) and 1-hydroxybenzotriazole (1.1 g) in DMF (50 ml) was stirred at room temperature for 10 min. The product of part (ii) above (1.5 g) was then added followed by dicyclohexylcarbodiimide (1.3 g), and the mixture was stirred at room temperature for 16 h and then filtered. The filtrate was concentrated in vacuo, treated with water and extracted with dichloromethane. The combined, dried organic extracts were concentrated to give the title compound (0.5 g) which was recrystallised from acetonitrile, MP 126°.

INTERMEDIATE 41

N-[(3,4-Dimethoxyphenyl)methyl]-N-methyl-4-nitrophenylaminocarbonylmethanamine

A mixture of Intermediate 20(b) (2.8 g), Intermediate 56 (3 g) and potassium carbonate (2.3 g) in DMF (50 ml) was heated at 60° for 24 h. The mixture was then evaporated, extracted with dichloromethane, washed with water, dried and concentrated to give a solid which was recrystallised from diethyl ether to provide the title compound (3.7 g). MP: 120°.

INTERMEDIATE 42

N-[(3,4-Dimethoxyphenyl)methyl]-N-methyl-4-aminophenylaminocarbonylmethanamine

A solution of Intermediate 41 (3.6 g) in ethanol (100 ml) was hydrogenated at room temperature in the presence of 10% palladium on carbon (500 mg). After hydrogen absorption was completed the catalyst was removed by filtration and the filtrate was concentrated to give the title compound (3.5 g).

NMR includes signals at d 2.5 (3H,s,N—CH₃); 3.8 (6H, s,OCH₃).

INTERMEDIATE 43

N-[2-(4-Aminophenylamino)ethyl]-3,4-dimethoxy-N-methylbenzenemethanamine

A solution of Intermediate 42 (3.5 g) in THF (50 ml) was added dropwise to a stirred suspension of lithium aluminium hydride in THF (30 ml) at room temperature and the mixture was heated under reflux for 48 h. Water was added carefully to the cooled mixture which was then filtered on a celite pad. The filtrate was evaporated to dryness and upon column chromatography (dichloromethane-methanol), the remaining residue gave the title compound (1.4 g).

NMR includes signals at d 2.15 (3H,s,N—$CH_3$); 2.5 and 3 (4H,2t,—$CH_2$—$CH_2$); 3.7 (6H,s,$OCH_3$).

INTERMEDIATE 44

9,10-Dihydro-5,7-dimethoxy-9-oxo-4-acridinecarboxylic acid

A mixture of 2-iodoisophthalic acid (5.8 g), 2,4-dimethoxy-aniline (4.3 g) and cuprous chloride (1 g) in 2,3-butanediol (20 ml) and toluene (10 ml) was heated to 120°. After most of toluene has distilled off, N-ethylmorpholine (10 ml) was added and the mixture was stirred at 120° for one hour. After cooling and dilution with 2N potassium carbonate the solution was filtered on celite. The filtrate was acidified with 2N hydrochloric acid and the greenish precipitate was recovered by filtration.

The product (4 g) was heated in polyphosphoric acid (50 g) at 120° for 1.5 hour to give the title compound which was recovered as a solid (1.5 g) by precipitation with water and purified by dissolving in 1N sodium hydroxide and reprecipitation with acetic acid (pH 4).

Analysis Found: C,62.1; H,4.6; N,4.3; $C_{16}H_{13}NO_5$, 0.5 $H_2O$ Requires: C,62.3; H,4.6; N,4.5%.

The following acid was prepared in a similar manner to Intermediate 44.

INTERMEDIATE 45

9,10-Dihydro-6,7,8-trimethoxy-9-oxo-4-acridinecarboxylic acid (1.5 g). IR includes a peak at 1620 $cm^{-1}$ (CO).

From 3,4,5-trimethoxyaniline (3.8 g) and 2-iodoisophthalic acid (5 g).

INTERMEDIATE 46

3-(2-Bromoethyl)nitrobenzene

Phosphorus tribromide (0.94 ml) was added dropwise to a solution of 3-nitrophenethyl alcohol (5 g) in anhydrous diethyl ether (30 ml) at 0°. The mixture was stirred at room temperature for 2 hours and then treated with a solution of potassium carbonate and then water. The organic layer was dried and concentrated in vacuo to give the title compound as an oil (4.51 g).

NMR includes d 3.25 (m,2H,$CH_2$—Ph) and 3.55 (m,2H, $CH_2$—Br).

INTERMEDIATE 47

(a) N-[(3,4-Dimethoxyphenyl)methyl]-N-methyl-3-nitrobenzeneethanamine

A mixture of Intermediate 46 (2.2 g), Intermediate 20(b) (1.71 g) and potassium carbonate (1.58 g) in DMF (50 ml) was heated at 60° for 36 hours. The mixture was filtered and the filtrate concentrated in vacuo. The residue was treated with water and extracted with methylene chloride. The organic extract was dried, concentrated and purified by column chromatography on silica gel eluting with methylene chloride/methanol (99:1) to give the title compound as an oil (1 g).

NMR includes d 2.2 (s,3H,N—$CH_3$) and 3.7 (s,6H,2×$OCH_3$).

In the same way was prepared the following compound:

(b) N-[(3,4-Dimethoxyphenyl)methyl]-N-methyl-3-(3-nitrophenoxy) propanamine

From 3-(3-bromopropoxy)nitrobenzene and Intermediate 20(b).

NMR includes d 2.2 (s,3H,N—$CH_3$), 3.35 (s,2H,N—$CH_2$—Ph) and 3.8 (s,6H,2×$OCH_3$).

INTERMEDIATE 48

(a) 3-Amino-N-[(3,4-dimethoxyphenyl)methyl]-N-methylbenzeneethanamine

A solution of Intermediate 47(a) (1 g) in ethanol (50 ml) was hydrogenated at room temperature in presence of 10% palladium-on-carbon (0.15 g). After the hydrogen absorption was completed, the catalyst was filtered off and the solution concentrated to give the title compound as an oil (0.8 g).

NMR includes d 2.25 (s,3H,N—$CH_3$), 3.4 (s,2H,$NH_2$) and 3.8 (s,6H,2×$OCH_3$).

In the same way was prepared the following compound:

(b) N-[3-(3-Aminophenoxy)propyl]-3,4-dimethoxy-N-methylbenzenemethanamine

From Intermediate 47(b).

NMR includes d 2.2 (s,3H,N—$CH_3$), 2.7 (s,2H,$NH_2$), 3.4 (s,2H,N—$CH_2$—Ph) and 3.7 (s,6H,2×$OCH_3$).

INTERMEDIATE 49

N-[(3,4-Dimethoxyphenyl)methyl]-N-methyl-3-(3-nitrophenyl)-2-propenamide

A mixture of 3-nitrocinnamic acid (10 g) and 1-hydroxybenzotriazole (8.26 g) in DMF (100 ml) was stirred at room temperature for 10 minutes. Intermediate 20(b) (9.2 g) was added followed by dicyclohexylcarbodiimide (10.63 g). The mixture was stirred at room temperature for 16 hours and then filtered. The filtrate was concentrated in vacuo, treated with dilute hydrochloric acid solution, then dilute sodium hydroxide solution and extracted with methylene chloride. The organic extract was dried and concentrated to give the title compound (15.63 g).

NMR includes d 3.1 (s,3H,N—$CH_3$) and 3.75 (s,6H,2×$OCH_3$).

INTERMEDIATE 50

3-Amino-N-[(3,4-dimethoxyphenyl)methyl]-N-methylbenzenepropanamide

A solution of Intermediate 49 (10 g) in ethanol (100 ml) was hydrogenated at room temperature in the presence of 10% palladium-on-carbon (1 g). After the hydrogen absorption was completed, the catalyst was filtered off and the filtrate concentrated in vacuo. The residue was purified by column chromatography on silica gel eluting with methylene chloride/methanol (98:2) to give the title compound as an oil (5.56 g).

NMR d 2.7 (s,2H,N—CH$_3$) and 3.65 (s,6H,2×OCH$_3$).

INTERMEDIATE 51

3-Amino-N-[(3,4-dimethoxyphenyl)methyl]-N-methylbenzenepropanamine

A solution of Intermediate 50 (5 g) in THF (100 ml) was added dropwise to a stirred suspension of lithium aluminium hydride (2.31 g) in THF (80 ml) at room temperature and the mixture was heated under reflux for 2 hours. Water (20 ml) was carefully added to the cooled mixture which was then filtered. The filtrate was concentrated, treated with water and extracted with diethyl ether. The organic extract was dried, evaporated and the product purified by column chromatography on silica gel eluting with methylene chloride/methanol (97:3) to give the title compound as an oil (2.46 g).

NMR includes d 2.1 (s,3H,N—CH$_3$), 3.35 (s,2H,N—CH$_2$—Ph) and 3.7 (s,6H,2×OCH$_3$).

INTERMEDIATE 52

4-(3-Methoxy-4-nitrophenyl)-3-buten-1-ol

The Wittig reaction in THF (100 ml) between 3-methoxy-4-nitrobenzaldehyde (1) (2 g) and 3-hydroxypropyltriphenylphosphonium bromide (2) (5.3 g) in presence of a solution of n-butyllithium (1.6M) in hexane (16.5 ml) gave the title compound (2.6 g) as an oil.

NMR includes signals at d 3.4(2H,t,CH$_2$OH); 3.6(3H,s, OCH$_3$).

(1) CA113 (19): 171567 w (2) A. R. Hands and A. J. H. Mercer, J. Chem. Soc. (c), (1968) 2448.

INTERMEDIATE 53

4-(4-Bromo-1-butenyl)-2-methoxy-1-nitrobenzene

Phosphorus tribromide (0.33 ml) was added dropwise to a solution of Intermediate 52 (2.6 g) in anhydrous diethyl ether (10 ml) at 0°. The mixture was stirred at room temperature for 1 hour, then washed with a solution of potassium carbonate (1M) and with water. The organic layer was dried and concentrated in vacuo to give the title compound (3.3 g) as a yellow oil. NMR includes signals at d 3.35 (2H,t,CH$_2$—Br); 3.8(3H,s,O—CH$_3$).

INTERMEDIATE 54

N-[4-(3-Methoxy-4-nitrophenyl)-3-butenyl]-3,4-dimethoxy-N-methylbenzenemethanamine A mixture of Intermediate 53 (3.3 g), Intermediate 20(b) (2.5 g) and potassium carbonate (1.9 g) in DMF (20 ml) was stirred at room temperature for 48 h. The mixture was filtered and the filtrate was evaporated. The residue was taken into water and extracted with dichloromethane. The organic layer was washed with water, dried, filtered and evaporated. The oily residue was then purified by silica gel column chromatography eluting with dichloromethane/methanol (95:5) to give the title compound (3.4 g) as an oil. NMR includes signals at d 2.1 (3H,s,N—CH$_3$); 3.7(6H,s,2× OCH$_3$); 3.8(3H,s,OCH$_3$).

INTERMEDIATE 55

4-Amino-N-[(3,4-dimethoxyphenyl)methyl]-3-methoxy-N-methylbenzenebutanamine

A solution of Intermediate 54 (1.2 g) in a mixture of ethanol (50 ml) and ethyl acetate (20 ml) was hydrogenated at room temperature in the presence of 10% palladium-on-carbon (0.1 g). After the hydrogen absorption was completed, the catalyst was filtered off and the solution concentrated to give the title compound (1 g) as an oil. NMR includes signals at d 2.1 (3H,s,N—CH$_3$); 3.65(3H,s,O—CH$_3$); 3.7(6H,s,2×OCH$_3$).

INTERMEDIATE 56

2-Chloro-N-(4-nitrophenyl)acetamide

Chloroacetyl chloride (11 ml) was added dropwise to a stirred mixture of potassium carbonate (18.8 g) and 4-nitroaniline (15 g) in DMF (100 ml) maintained at 0°. The mixture was then allowed to stand overnight at room temperature and poured into crushed ice. A yellow solid was recovered and crystallised from toluene containing isopropyl alcohol (10%) to give the title compound (10 g), MP: 180°.

NMR includes signals at d 4.1 (2H,s,COC$\underline{H}_2$Cl); 7.4–8.1 (4H,m,aromatics); 10.3(1H,bs,NH).

INTERMEDIATE 57

3,4-Dihydro-6,7-dimethoxy-N-(4-nitrophenyl)-2(1H)-isoquinolineacetamide

A mixture of Intermediate 56 (10.3 g), potassium carbonate (8 g) and 1,2,3,4-tetrahydro-6,7-dimethoxyisoquinoline (9.3 g) in DMF (100 ml) was heated overnight at 60° After cooling, the reaction mixture was poured onto ice and the insoluble material recovered and dried to give the title compound, MP: 173°–178°. NMR includes signals at d 2.8(4H,s,2×CH$_2$); 3.2(2H,s,COC$\underline{H}_2$—N); 3.7(2H,s,N—C$\underline{H}_2$—Ph); 3.7(6H,m,2×OCH$_3$); 6.2–8.15(6H,m,aromatics); 9.3(1H,bs,N$\underline{H}$CO).

INTERMEDIATE 58

N-(4-Aminophenyl)-3,4-dihydro-6,7-dimethoxy-2(1H)-isoquinolineacetamide

A suspension of Intermediate 57 (15 g) and 10% palladium-on-carbon (1 g) in ethanol (200 ml) was stirred at room temperature under a slight overpressure of hydrogen. After 2 h the catalyst was filtered off, and washed with dichloromethane/methanol (9:1). The filtrate and washing were concentrated and the crystalline residue gave upon washing with ethanol and drying the title compound (10.6 g), MP: 185°. NMR includes signals at d 2.8(4H,s,2×CH$_2$); 3.15(2H, s,CO—C$\underline{H}_2$—N); 3.6(2H,s,Ph—CH$_2$—N); 3.7(6H,s,2× OCH$_3$); 6.15–7.3(6H,m,aromatics); 8.65(1H,bs,CONH).

INTERMEDIATE 59

N-[2-(1,2,3,4-Tetrahydro-6,7-dimethoxy-2-isoquinolinyl)ethyl]-1,4-benzenediamine A solution of borane in tetrahydrofuran (1M; 35.4 ml) was added to a stirred solution of Intermediate 58 (2 g) in THF (150 ml). After 4 h of refluxing the reaction mixture was cooled, treated with concentrated hydrochloric acid to make the solution up to 3N in hydrochloric acid and then refluxed again for 15 min. 10N Sodium hydroxide was added and the mixture was extracted with dichloromethane. The organic layer was washed with water, dried and concentrated to give a residue which after purification by silica gel column chromatography eluting with toluene/isopropylamine (95:5) gave the title compound as an oil (1.2 g). NMR includes signals at d 2.6(4H,bs,Ph—CH$_2$—CH$_2$—N); 3.45(4H,s, CH$_2$—NHPh and PhCH$_2$—N); 3.6(6H,s,2×OCH$_3$); 6.3(6H, s,aromatics).

INTERMEDIATE 60

4-[2-(2,3-Dihydro-5,6-dimethoxy-1H-isoindol-2-yl)ethyl]benzenamine 4,5-Bischloromethyl veratrol (2.35 g: S. H. Wood, M. A. Peny and C. C. Tung, J. A. C. S. (1950), 72, 2989–2991) was added at room temperature to a stirred suspension of 50% aqueous sodium hydroxide (5 ml), toluene (25 ml), 4-aminophenylethylamine (1.5 g) and Aliquat (0.2 g). The heterogeneous mixture was stirred at room temperature for 16 hours, poured in water and extracted with methylene chloride. The organic layer was dried and the solvent evaporated in vacuo. The residue was purified by column chromatography on silica gel eluting with methylene dichloride/methanol (95:5) to give the title compound as a solid (0.6 g), MP: 150°. NMR includes signals at d 2.7(4H,m,Ph—CH$_2$—CH$_2$—N); 4.6(2H,bs,NH2); 3.7(6H,s,2×OCH$_3$); 3.8(4H,s, 2×N—CH$_2$Ph); 6.2–7.0(6H,m,aromatics).

INTERMEDIATE 61

1-(4-Nitrophenyl)-2-(1,2,3,4-tetrahydro-6,7-dimethoxy-2-isoquinolinyl)ethanone hydrobromide A solution of 6,7-dimethoxy-1,2,3,4-tetrahydroisoquinoline (15.63 g) and 2-bromo-4'-nitroacetophenone (16.47 g) in a mixture of ethanol (150 ml) and methylene chloride (150 ml) was heated at 60° for 24 hours. After cooling to room temperature yellow crystals appeared. These were collected by filtration and dried in vacuo to give the title compound (9.4 g); MP: 216°. NMR(D$_6$-DMSO) includes signals at d 3.6(6H,s,2×OCH$_3$); 4.2(2H,s,N—CH$_2$—Ph); 4.95(2H,s,CO—CH$_2$—N); 6.6(2H,aromatics isoquinoline); 8(4H,m,aromatics).

INTERMEDIATE 62

3,4-Dihydro-6,7-dimethoxy-a-(4-nitrophenyl)-2(1H)-isoquinolineethanol

To a suspension of Intermediate 61 (9.4 g) in methanol (600 ml) was added portionwise sodium borohydride (2.44 g) and the mixture was stirred at room temperature for 16 hours. The reaction was diluted with water (200 ml), filtered and evaporated in vacuo. The residue was extracted with methylene chloride and washed with water. The organic layer was dried and evaporated in vacuo to give the title compound (1.15 g), after crystallisation from ethanol, MP: 130°. NMR includes signals at d 2.4–3.1(6H,m,3×CH$_2$); 3.7(6H,s,2×OCH$_3$); 4.2(1H,bs,OH); 4.8(1H,m,H—C—OH ); 6.1–8.1 (6H,m,aromatics).

INTERMEDIATE 63 a-(4-Aminophenyl)-3,4-dihydro-6,7-dimethoxy-2(1H)-isoquinolineethanol

A solution of Intermediate 62 (2.4 g) in ethanol (200 ml) was hydrogenated at room temperature in the presence of 10% palladium-on-carbon (0.3 g). After hydrogen absorption was completed, the catalyst was filtered off and the solution was concentrated to give the title compound (1.9 g) as a white solid, MP: 168°. NMR includes signals at d 2.4–2.9(6H,m,3×CH$_2$); 3.5(2H,bs,NH2); 3.7(6H,s,2× OCH$_3$); 4.55(1H,t,H—COH); 6.25–7.1 (6H,m,aromatics).

INTERMEDIATE 64

2-Bromo-N-methyl-N-[(4-nitrophenyl)methyl]acetamide

To a solution of bromoacetyl bromide (30 g) in methylene chloride (20 ml) at 0° was added a solution of N-methyl-4-nitrobenzenemethanamine (8.3 g; G. I. Wilson, J. Chem. Soc., 1926, 2461) in methylene chloride (10 ml) and triethylamine (12 ml). The reaction was stirred 5 min. at 0° and then water (20 ml) was added. The methylene chloride layer was dried and evaporated in vacuo. The residue was purified by column chromatography eluting with methylene chloride/methanol (97:3) to give the title compound (15 g) as an oil. NMR includes signals at d 3.1(3H,s,N—CH$_3$); 3.9(2H, s,CH$_2$Br); 4.55(2H,s,Ph—CH$_2$—N); 7.0–8.3(4H,m,aromatics).

INTERMEDIATE 65

3,4-Dihydro-6,7-dimethoxy-N-methyl-N-[(4-nitrophenyl)methyl]-2(1H)-isoquinolineacetamide A mixture of Intermediate 64 (1.8 g), 6,7-dimethoxy-1,2, 3,4-tetrahydroisoquinoline (1.4 g) and potassium carbonate (1.6 g) in DMF (150 ml) was stirred overnight. After removal of insoluble material by filtration the solvent was evaporated in vacuo and the residue partitioned between dichloromethane and water. The organic phase was dried, then concentrated under reduced pressure and the product, after purification by column chromatography eluting with methylene chloride/methanol (96:4), gave the title compound (1.65 g). NMR includes signals at d 2.8(4H,m,2× CH$_2$); 3.0(3H,s,N—CH$_3$); 3.33(2H,s,CO—CH$_2$—N); 3.6(2H,s,N—CH$_2$—Ph); 3.7(6H,s,2×OCH$_3$); 4.55(2H,s, Ph—CH$_2$13 NHCO); 6.2–8.1(6H,m,aromatics).

INTERMEDIATE 66

N-[(4-Aminophenyl)methyl]-3,4-dihydro-6,7-dimethoxy-N-methyl-2(1H)-isoquinolineacetamide A solution of Intermediate 65 (1.65 g) in ethyl acetate (100 ml) was hydrogenated at room temperature and atmospheric pressure in the presence of 10% palladium-on-carbon (0.34 g). After hydrogen absorption was completed, the catalyst was filtered off and the solution was concentrated to give the title compound (1.43 g) as a white solid, MP: 175°–215°. NMR includes signals at d 2.8(7H,m,NCH$_3$ and 2×CH$_2$); 3.2(2H,s,CO—CH$_2$—N); 3.5(2H,s,N—CH$_2$—Ph); 3.7(6H,s,2×CH$_3$).

INTERMEDIATE 67

N-[(4-Aminophenyl)methyl]-3,4-dihydro-6,7-dimethoxy-N-methyl-2(1H)isoquinolineethanamine A solution of Intermediate 66 (1.49 g) in THF (150 ml) was added dropwise to a stirred suspension of lithium aluminium hydride (0.47 g) in THF (100 ml) at room temperature for 4 hours. Water (5 ml) was added carefully to the cooled mixture which was filtered and the filtrate concentrated and the residue extracted with methylene chloride. The organic layer was dried and evaporated. The resulting product was purified by column chromatography on silica gel eluting with methylene chloride/isopropylamine (92:8) to give the title compound as an oil (0.7 g). NMR includes signals at d 2.15(3H,s,N—CH$_3$); 2.55(8H,m,4×CH$_2$); 3.55(2H,s,NH$_2$); 3.65(6H,s,2×OCH$_3$); 6.3–7.1(6H,m,aromatics)

INTERMEDIATE 68

2-[[(3,4-Dimethoxyphenyl)methyl]methylamino]-N-methyl-N-[(4-nitrophenyl)methyl]acetamide A mixture of Intermediate 64 (4.3 g), Intermediate 20(b) (3.26 g) and potassium carbonate (4.14 g) in DMF (100 ml) was stirred overnight. The mixture was filtered, and the filtrate concentrated in vacuo to a residue which was extracted with methylene chloride. After washing with water and drying, the organic layer was evaporated to a syrup which was purified by column chromatography on silica gel eluting with ethyl acetate/cyclohexene (1:1) to give the title compound as an oil (5.7 g). NMR includes signals at d 2.3(3H,s,N—CH$_3$); 3.7(6H,s,2×OCH$_3$); 4.5(2H,s,Ph—CH$_2$—NHCO).

INTERMEDIATE 69

N-[(4-Aminophenyl)methyl]-2-[[(3,4-dimethoxyphenyl)methyl]-methylamino]-N-methylacetamide A solution of Intermediate 68 (5.7 g) in a mixture of ethyl acetate/methanol (1:2) (100 ml) was hydrogenated at room temperature and atmospheric pressure in the presence of 10% palladium-on-carbon (0.8 g). After hydrogen absorption was completed, the catalyst was filtered off and the filtrate was concentrated to give the title compound (5.2 g) as an oil. NMR includes signals at d 3.8(6H,s,2×OCH$_3$); 4.5(2H,s,Ph—CH$_2$—NCO).

INTERMEDIATE 70

N-[(4-Aminophenyl)methyl]-N'-[(3,4-dimethoxyphenyl)methyl]-N,N'-dimethyl-1,2-ethanediamine A solution of Intermediate 69 (5.2 g) in THF (150 ml) was added dropwise at room temperature to a stirred suspension of lithium aluminium hydride (1 g) in THF (50 ml). After 4 hours, water (10 ml) was added carefully to the cooled mixture which was then filtered. The filtrate was concentrated to dryness and the residue diluted with methylene chloride and extracted with hydrochloric acid (1M). The aqueous layer was basified with an aqueous solution of sodium hydroxide (1M) and extracted with methylene chloride. The organic layer was dried and then concentrated in vacuo. The residue was purified by column chromatography on silica gel eluting with cyclohexane/methylene chloride/isopropylamine (5:4:1) to give the title compound as an oil (2 g). NMR includes signals at d 2.1 (6H,s,2×NCH$_3$); 2.4(4H,s,2×NCH$_2$); 3.2(4H,m,2×N—CH$_2$—Ph); 3.6(6H,s,2×OCH$_3$); 3.85(2H,s,NH$_2$); 6.1–7.5(7H,m,aromatics).

INTERMEDIATE 71

3,4-Dimethoxy-N-methyl-N-[4-(4-nitrophenyl)-2-butenyl]benzenemethanamine

A mixture of Intermediate 20(b) (9 g), potassium carbonate (8 g) and 1-chloro-4-(4-nitrophenyl)-2-butene (10.6 g; Morgan and al., J. Med. Chem., 8, (1986), 1398–1405) in 4-methyl-2-pentanone (300 ml) was refluxed for 18 hours. After cooling, the mixture was filtered and evaporated in vacuo. The residue was purified by column chromatography eluting with methylene chloride/methanol (97.5:2.5) to give the title compound (2 g) as an oil. NMR includes signals at d 2.2(3H,s,N—CH$_3$); 3.9(6H,s,2×OMe); 5.7(2H,m,double bond); 6.9(3H,m,aromatics Ph(OMe)$_2$); 7.4 and 8.15(4H,2d, aromatics PhNO$_2$).

INTERMEDIATE 72

N-[4-(4-Aminophenyl)-2-butenyl]-3,4-dimethoxy-N-methylbenzenemethanamine

Intermediate 71 (1.7 g) was dissolved at room temperature with stirring in a mixture of methanol (50 ml) and concentrated hydrochloric acid (2 ml). Iron powder (1.5 g) was then added slowly, and the reaction mixture was heated under reflux for 1 h. The mixture was then evaporated, basified with sodium hydroxide and extracted with diethyl ether. The organic layer was dried and evaporated in vacuo to give the title compound (0.21 g) as an oil. NMR includes signals at d 2.15(3H,s,N—CH$_3$); 3.8(6H,s,2×OMe); 5.55(2H,m,double bond); 6.3–7.2(7H,m,aromatics).

INTERMEDIATE 73

3,4-Dimethoxy-N-methyl-N-[3-(4-nitrophenyl)-2-propenyl]benzenemethanamine

A mixture of Intermediate 20(b) (3.6 g), 1-chloro-3-(4-nitrophenyl)-2-propene (4.8 g; Cignarella and al., J. Med. Chem., 8, (1965), 326–329) and potassium carbonate (3.5 g) in 4-methyl-2-pentanone (60 ml) was refluxed for 3 hours. After cooling, the mixture was filtered and the filtrate was evaporated in vacuo. The residue was purified by column chromatography eluting with methylene chloride/methanol (95:5) to give the title compound (4.9 g) as an oil. NMR includes signals at d 2.25(3H,s,NCH$_3$); 3.2(2H,d,N—CH$_2$—CH=CH); 3.5(2H,s,NCH$_2$Ph); 3.85(6H,s,2×OMe); 6.55(2H,m,double bond); 6.8(3H,d,aromatics Ph(OMe)2); 7.4 and 8.1(4H,2d,aromatics PhNO2).

INTERMEDIATE 74

4-[3-[[(3,4-Dimethoxyphenyl)methyl]methylamino]-1-propenyl]benzenamine

Intermediate 73 (4.8 g) was dissolved in a mixture of methanol (100 ml) and concentrated hydrochloric acid (10 ml) at room temperature with stirring. Iron powder (5 g) was then added slowly and the reaction mixture was refluxed for 0.5 h. After cooling, the mixture was evaporated, diluted with water (20 ml), basified with sodium hydroxide solution, concentrated and extracted with diethyl ether. The organic layer was dried and evaporated to give the title compound (3.95 g) as an oil. NMR includes signals at d 2.2(3H,s, NCH₃); 3.15(2H,d,N—CH₂—CH=CH); 3.5(2H,s, NCH₂Ph); 3.6(2H,s,NH₂); 3.8(6H,s,2×OMe); 5.7–7.6(9H, m,aromatics and double bond).

INTERMEDIATE 75

1,2,3,4-Tetrahydro-6-methoxy-2-[2-(4-nitrophenyl)ethyl]isoquinoline

A mixture of 1-(2-bromoethyl)-4-nitrobenzene (6.4 g), 1,2,3,4-tetrahydro-6-methoxyisoquinoline (4.6 g; Daniel J. Sall and Gary L. Grunewald, J. Med. Chem. 1987, 30, 2208–2216) and potassium carbonate (9.7 g) in DMF (150 ml) was stirred at 50° for 15 h. The mixture was evaporated to dryness and the residue was extracted with dichloromethane. The organic layer was washed with water, dried, filtered and evaporated. The residue was then purified by column chromatography eluting with dichloromethane/methanol (98:2) to give the title compound (2 g) as an oil which solidified on standing.

NMR includes signals at d 3.6 (2H,m,N—CH₂Ar), 3.7 (3H,s,OCH₃).

INTERMEDIATE 76

4-[2-(1,2,3,4-Tetrahydro-6-methoxy-2-isoquinolinyl)ethyl]-benzenamine

A solution of intermediate 75 (2 g) in ethanol (100 ml) was hydrogenated at room temperature in the presence of 10% palladium-on-carbon (0.2 g). After the hydrogen absorption was completed, the catalyst was filtered off and the filtrate was concentrated in vacuo to give the title compound (1.8 g) as an orange oil which solidified on standing.

NMR includes signals at d 3.4 (2H,s,NH₂), 3.55 (2H,s, N—CH₂Ar), 3.65 (3H,s,OCH₃).

INTERMEDIATE 77

1,2,3,4-Tetrahydro-6,7-dimethoxy-2-[3-(3-nitrophenyl)-1-oxo-2-propenyl]isoquinoline A mixture of 3-nitrocinnamic acid (10 g) and 1-hydroxybenzotriazole (8.2 g) in DMF (100 ml) was stirred at room temperature for 10 min. 1,2,3,4-Tetrahydro-6,7-dimethoxyisoquinoline (10 g) was then added, followed by dicyclohexylcarbodiimide (10.6 g) and the mixture was stirred at 50° for 48 h and then filtered. The filtrate was concentrated in vacuo, treated with dilute sodium hydroxide and extracted with dichloromethane. The dried organic extract was evaporated and purified by column chromatography eluting with dichloromethane/methanol (97:3) to give the title compound (7.8 g). NMR includes a signal at d 3.85 (6H,s,OCH₃).

INTERMEDIATE 78

2-[3-(3-Aminophenyl)-1-oxopropyl]-1,2,3,4-tetrahydro-6,7-dimethoxy-isoquinoline

A solution of Intermediate 77 (7.8 g) in ethanol (100 ml) was hydrogenated at room temperature in the presence of 10% palladium-on-carbon (1 g). After the hydrogen absorption was completed, the catalyst was filtered off and the filtrate concentrated in vacuo to give the title compound (6.8 g).

IR: Freq CO: 1640 cm-1, Freq NH₂: 3450 cm-1.

INTERMEDIATE 79

3-[3-(1,2,3,4-Tetrahydro-6,7-dimethoxy-2-isoquinolinyl)propyl]benzenamine

A solution of Intermediate 78 (6.8 g) in THF (100 ml) was added dropwise to a stirred suspension of lithium aluminium hydride (3 g) in THF (100 ml) at room temperature and the mixture was heated under reflux for 3 h. Water was then added carefully to the cooled mixture which was filtered, evaporated and extracted with ether. The extract was dried and evaporated to give the title compound (5.4 g) as an oil which solidified on standing.

IR: Freq NH₂: 3350–3450 cm-1.

INTERMEDIATE 80

1-[[(3,4-Dimethoxyphenyl)methyl]methylamino]-3-(4-nitrophenoxy)-2-propanol

A mixture of 1,2-epoxy-3-(4-nitrophenoxy)propane (6 g; Sigma) and Intermediate 20(b) (5 g) in isopropanol (100 ml) was heated under reflux for 18 h and evaporated. The oily residue was crystallised from ether to give the title compound (8.3 g) as a white solid.

NMR includes signals at d 2.3 (3H,s,N—CH₃), 3.9 (6H, s,OCH₃).

INTERMEDIATE 81

1-(4-Aminophenoxy)-3-[[(3,4-dimethoxyphenyl)methyl] methylamino]-2-propanol

A solution of Intermediate 80 (8 g) in ethanol (100 ml) was hydrogenated at room temperature in the presence of 10% palladium-on-carbon (0.8 g). After the hydrogen absorption was completed, the catalyst was filtered off and the filtrate concentrated in vacuo. The oily product was then purified by column chromatography eluting with dichloromethane/methanol (95:5) to give the title compound (5.8 g) as an oil. NMR includes signals at d 2.25 (3H,s,N—CH₃), 3.8 (6H,s,OCH₃).

INTERMEDIATE 82

3,4,5-Trimethoxy-N-methyl-N-[3-(4-nitrophenoxy)propyl]benzene methanamine

A mixture of 1-(3-chloropropoxy)-4-nitrobenzene (4.6 g), 3,4,5-trimethoxy-N-methylbenzenemethanamine (4.1 g; Sigma) and potassium carbonate (2.9 g) in DMF (60 ml) was heated at 70° for 24 h. The mixture was then filtered and the filtrate evaporated. The residue was taken up in water and extracted with dichloromethane. The organic layer was washed with water, dried, evaporated and purified by column chromatography eluting with dichloromethane/methanol (99:1) to give the title compound (5.8 g) as a yellow oil. NMR includes signals at d 2.15 (3H,s,N-CH₃), 3.3 (2H,s, CH₂—Ar), 3.7 (9H,s,OCH₃).

INTERMEDIATE 83

N-[3-(4-Aminophenoxy)propyl]-3,4,5-trimethoxy-N-methylbenzenemethanamine

A solution of Intermediate 82 (5.8 g) in ethanol (100 ml) was hydrogenated at room temperature in the presence of 10% palladium-on-carbon (0.5 g). After hydrogen absorption was completed, the catalyst was filtered off and the solution was concentrated to give the title compound (5.1 g) as an oil. NMR includes signals at d 2.25 (3H,s,N—CH₃), 3.5 (2H,s,CH₂—Ar), 3.8 (9H,s,OMe).

INTERMEDIATE 84

1,2,3,4-Tetrahydro-6,7-dimethoxy-2-[(4-methoxy-3-nitrophenyl)acetyl]isoquinoline A mixture of 4-methoxy-3-nitrophenylacetic acid (1.2 g) and 1-hydroxybenzotriazole (0.95 g) in DMF (30 ml) was stirred at room temperature for 10 min. 1,2,3,4-Tetrahydro-6,7-dimethoxy-isoquinoline (1.1 g) in DMF (20 ml) was then added, followed by dicyclohexylcarbodiimide (1.2 g) and the mixture was stirred at room temperature for 6 h and then filtered. The filtrate was concentrated in vacuo, treated with dilute sodium hydroxyde and extracted with ethyl acetate. The dried organic extract was evaporated to give the title compound (1.6 g) as an oil which crystallised from ethanol as a white solid, MP 175°. IR: Freq CO: 1650 cm-1.

INTERMEDIATE 85

2-[(3-Amino-4-methoxyphenyl)acetyl]-1,2,3,4-tetrahydro-6,7-dimethoxyisoquinoline A solution of Intermediate 84 (1.6 g) in ethanol (50 ml) was hydrogenated at room temperature in the presence of 10% palladium-on-carbon (0.3 g). After hydrogen absorption was completed, the catalyst was filtered off and the solution was concentrated to give the title compound (1.4 g) as an oil. IR: Freq CO: 1650 cm-1, Freq NH₂: 3340–3440 cm-1.

INTERMEDIATE 86

5-[2-(1,2,3,4-Tetrahydro-6,7-dimethoxy-2-isoquinolinyl)ethyl]-2-methoxybenzenamine A solution of Intermediate 85 (1.4 g) in THF (30 ml) was added dropwise to a stirred suspension of lithium aluminium hydride (0.9 g) in THF (50 ml) at room temperature and the mixture was heated under reflux for 3 h. Water was then added carefully to the cooled mixture which was then filtered, evaporated and extracted with ether. The extract was dried and evaporated to give the title compound (1.2 g) as an oil which solidified on standing.

IR: Freq NH₂: 3340–3440 cm-1.

INTERMEDIATE 87

1,2,3,4-Tetrahydro-2-[3-(4-nitrophenoxy)propyl]isoquinoline

A mixture of 1-(3-bromopropoxy)-4-nitrobenzene (10 g), 1,2,3,4-tetrahydroisoquinoline (5.1 g) and potassium carbonate (10.6 g) in DMF (100 ml) was stirred at 70° for 24 h. The mixture was then filtered and the filtrate evaporated. The residue was taken up with water and extracted with dichloromethane. The organic layer was washed with water, dried, evaporated and purified by column chromatography eluting with dichloromethane/methanol (96:4) to give the title compound (8.8 g) as a yellow oil. NMR includes signals at d 3.6 (2H,s,N—CH₂Ar), 4.1 (2H,t,O—CH₂).

INTERMEDIATE 88

4-[3-(1,2,3,4-Tetrahydro-2-isoquinolinyl)propoxy]benzenamine

Intermediate 87 (8.8 g) was dissolved in a mixture of methanol (80 ml) and concentrated hydrochloric acid (50 ml) at room temperature with stirring. Iron powder (7.9 g) was then added portionwise and the mixture was heated under reflux for 2 h. The mixture was then cooled, poured onto ice, basified with sodium hydroxide and extracted with ethyl acetate. The organic layer was washed with water, dried and evaporated to give the title compound (4.5 g) as a red oil. NMR includes signals at d 3.7 (2H,s,N—CH₂Ar), 3.9 (2H,t,O—CH₂).

INTERMEDIATE 89

1,2,3,4-Tetrahydro-7-methoxy-2-[2-(4-nitrophenyl)ethyl]isoquinoline

A mixture of 1-(2-bromoethyl)-4-nitrobenzene (3.7 g), 1,2,3,4-tetrahydro-7-methoxyisoquinoline (2.7 g; Daniel J. Sall and Gary L. Grunewald, J. Med. Chem. 1987, 30, 2208–2216) and potassium carbonate (6.7 g) in isopropanol (150 ml) was stirred under reflux for 48 h. The mixture was evaporated to dryness, and the residue was extracted with dichloromethane. The organic layer was washed with water, dried, filtered and evaporated. The residue was then purified by column chromatography elating with dichloromethane/methanol (99:1) to give the title compound (1.6 g) as an orange solid, MP: 92°–94°. NMR includes signals at d 3.6 (2H,m,N—CH₂Ar), 3.7 (3H,s,OCH₃).

INTERMEDIATE 90

4-[2-(1,2,3,4-Tetrahydro-7-methoxy-2-isoquinolinyl)ethyl]-benzenamine

A solution of Intermediate 89 (1.6 g) in ethanol (100 ml) was hydrogenated at room temperature in the presence of 10% palladium-on-carbon (0.16 g). After the hydrogen absorption was completed, the catalyst was filtered off and the filtrate was concentrated in vacuo to give the title compound (1.4 g) as a white solid, MP: 82°–84°.

NMR includes signals at d 3.4 (2H,s,NH₂), 3.45 (2H,s, N—CH₂Ar), 3.55 (3H,s,OCH₃).

INTERMEDIATE 91

1,2,3,4-Tetrahydro-6,7-dimethoxy-2-[2-(3-nitrophenyl)ethyl]isoquinoline

A mixture of 1-(2-bromoethyl)-3-nitrobenzene (2.3 g), 1,2,3,4-tetrahydro-6,7-dimethoxyisoquinoline hydrochloride (2.3 g) and potassium carbonate (3 g) in DMF (50 ml) was heated at 50° for 12 h. The mixture was then filtered and the filtrate evaporated. The residue was then taken up in water, extracted with dichloromethane, dried, evaporated and purified by column chromatography eluting with dichloromethane/methanol (99:1) to give the title compound (1.4 g) as a yellow oil. NMR includes signals at d 3.6 (2H,s,N—CH₂Ar), 3.75 (6H,s,OCH₃).

INTERMEDIATE 92

3-[2-(1,2,3,4-Tetrahydro-6,7-dimethoxy-2-isoquinolinyl)ethyl]benzenamine

A solution of Intermediate 91 (1.4 g) in ethanol (50 ml) was hydrogenated at room temperature in the presence of 10% palladium-on-carbon (0.14 g). After hydrogen absorption was completed, the catalyst was filtered off and the filtrate was concentrated in vacuo to give the title compound (1.15 g) as a yellow oil which solidified.

NMR includes signals at d 3.6 (2H,s,N—CH$_2$Ar), 3.75 (6H,s,OCH$_3$), 4.5 (2H,s,NH$_2$).

INTERMEDIATE 93

N-[(3,4-Dimethoxyphenyl)methyl]-4-methoxy-N-methyl-3-nitrobenzeneethanamide

A mixture of 4-methoxy-3-nitrobenzeneacetic acid (1.2 g; CA 87, 84684h) and 1-hydroxybenzotriazole (0.95 g) in DMF (30 ml) was stirred for 10 min. Intermediate 20(b) (1.1 g) in DMF (20 ml) was then added, followed by dicyclohexylcarbodiimide (1.2 g) and the mixture was stirred at room temperature for 6 h and then filtered. The filtrate was concentrated in vacuo, treated with dilute sodium hydroxide and extracted with ethyl acetate. The dried, organic extract was evaporated to give an oil which was purified by column chromatography eluting with dichloromethane/methanol (95:5) to give the title compound (1.5 g) as an oil.

IR: Freq CO: 1640 cm-1.

INTERMEDIATE 94

3-Amino-N-[(3,4-dimethoxyphenyl)methyl]-4-methoxy-N-methylbenzeneacetamide

A solution of Intermediate 93 (1.45 g) in ethanol (40 ml) was hydrogenated at room temperature in the presence of 10% palladium-on-carbon (0.25 g). After the hydrogen absorption was completed, the catalyst was filtered off and the solution was concentrated to give the title compound (1.2 g) as an oil.

IR: Freq CO: 1630 cm-1, Freq NH$_2$: 3350–3450 cm-1.

INTERMEDIATE 95

3-Amino-N-[(3,4-dimethoxyphenyl)methyl]-4-methoxy-N-methylbenzeneethanamine

A solution of Intermediate 94 (1.2 g) in THF (30 ml) was added dropwise to a stirred suspension of lithium aluminium hydride (0.9 g) in THF (50 ml) at room temperature and the mixture was heated under reflux for 3 h. Water was added carefully to the cooled mixture which was then filtered, washed with THF, evaporated and extracted with ether. The extract was dried and evaporated to give the title compound (1 g) as an oil.

IR: Freq NH$_2$: 3350–3450 cm-1.

INTERMEDIATE 96

1,2,3,4-Tetrahydro-5,6-dimethoxy-2-[2-(4-nitrophenyl)ethyl]isoquinoline

A mixture of 1-(2-bromoethyl)-4-nitrobenzene (0.3 g), 1,2,3,4-tetrahydro-5,6-dimethoxyisoquinoline [0.25 g; R. D. Haworth, J. Chem. Soc., 2281 (1987); Robin D. Clark, J. Med. Chem., 596–600, 33, (1990)] and potassium carbonate (0.5 g) in DMF (25 ml) was heated at 60° for 3 h. The mixture was then filtered and the filtrate evaporated. The residue was taken up in water, extracted with dichloromethane, dried, evaporated and purified by column chromatography eluting with dichloromethane/methanol (99:1) to give the title compound (0.3 g) as an orange solid, MP:97°. NMR includes signals at d 3.6 (2H,s,N—CH$_2$Ar), 3.75 (6H,s,OCH$_3$).

INTERMEDIATE 97

4-[2-(1,2,3,4-Tetrahydro-5,6-dimethoxy-2-isoquinolinyl)ethyl]-benzenamine

A solution of Intermediate 96 (0.3 g) in ethanol (20 ml) was hydrogenated at room temperature in the presence of 10% palladium-on-carbon (30 mg). After the hydrogen absorption was completed, the catalyst was filtered off and the filtrate was concentrated in vacuo to give the title compound (0.22 g) as a yellow oil. NMR includes signals at d 3.55 (2H,s,N—CH$_2$Ar), 3.65–3.85 (8H, OCH$_3$ and NH$_2$).

INTERMEDIATE 98

1,2,3,4-Tetrahydro-6,7,8-trimethoxy-2-[2-(4-nitrophenyl)ethyl]isoquinoline

A mixture of 1-(2-bromoethyl)-4-nitrobenzene (0.34 g), 1,2,3,4-tetrahydro-6,7,8-trimethoxyisoquinoline [0.33 g; J. Chem. Soc. D, (20), 1296–1297 (1970)] and potassium carbonate (0.5 g) in DMF (20 ml) was heated at 50° for 12 h. The mixture was then filtered and the filtrate evaporated. The residue was taken up in water, extracted with dichloromethane, dried, evaporated and purified by column chromatography eluting with dichloromethane/methanol (99:1) to give the title compound (0.34 g) as a red solid, MP: 110°. NMR includes signals at d 3.55 (2H,s,N—CH$_2$Ar), 3.70 (6H,s,OCH$_3$), 3.75 (3H,s,OCH$_3$).

INTERMEDIATE 99

4-[2-(1,2,3,4-Tetrahydro-6,7,8-trimethox,2-isoquinolinyl)ethyl]-benzenamine

A solution of Intermediate 98 (0.34 g) in ethanol (10 ml) was hydrogenated at room temperature in the presence of 10% palladium-on-carbon (50 mg). After the hydrogen absorption was completed, the catalyst was filtered off and the filtrate was concentrated in vacuo to give the title compound (0.3 g) as a white solid, MP: 92°.

NMR includes signals at d 3.55 (2H,s,N—CH$_2$Ar), 3.7–3.75 (11H, OCH$_3$ and NH$_2$).

INTERMEDIATE 100

1,2,3,4-Tetrahydro-6,7-dimethoxy-2-[2-(4-nitrophenyl)ethyl]isoquinoline

A mixture of 1-(2-bromoethyl)-4-nitrobenzene (9.64 g), 1,2,3,4-tetrahydro-6,7-dimethoxyisoquinoline hydrochloride (10.59 g) and potassium carbonate (17.38 g) in isopropanol (150 ml) was refluxed for 48 h. The mixture was then filtered and the filtrate evaporated to dryness. The resulting residue was taken up in water and extracted with dichloromethane. The organic layer was washed with water, dried and evaporated to give an oil which crystallised in a mixture of 2-propanol and diethyl ether to give the title compound (10.27 g). M.p.: 118°–119°.

Analysis Found: C,66.48; H,6.48; N,8.14; $C_{19}H_{22}N_2O_4$ requires: C,66.65; H,6.48; N,8.18%.

INTERMEDIATE 101

4-[2-(1,2,3,4-Tetrahydro-6,7-dimethoxy-2-isoquinolinyl)ethyl]benzenamine

Method a:

A solution of Intermediate 100 (20 g) in ethanol (300 ml) was hydrogenated at room temperature and atmospheric pressure in the presence of 10% palladium-on-carbon (2 g). After the hydrogen absorption was completed, the catalyst was filtered off and the solution was concentrated to give the title compound (17.2 g) as an oil which solidified by scratching in hexane.

Method b:

Iron powder (12.44 g) was added portionwise at room temperature to a stirred solution of Intermediate 100 (14 g) in a mixture of methanol (150 ml) and concentrated hydrochloric acid (150 ml). After heating under reflux for 45 min, the mixture was cooled, poured onto ice, basified with a solution of sodium hydroxide and extracted with ethyl acetate. The organic layer was washed with water, dried and evaporated to give the title compound. M.p.: 128° (ethanol).

Analysis Found: C,72.77; H,7.80; N,9.17; $C_{19}H_{24}N_2O_2$ requires: C,73.05; H,7.74; N,8.97%.

EXAMPLE 1

9,10-Dihydro-5-methoxy-9-oxo-N-[4-[2-(1,2,3,4-tetrahydro-6,7-dimethoxy-2-isoquinolinyl)ethyl]phenyl]-4-acridinecarboxamide A mixture of 9,10-dihydro-5-methoxy-9-oxo-4-acridinecarboxylic acid (1.3 g) and 1-hydroxybenzotriazole (0.43 g) in DMF (30 ml) was stirred at room temperature for 10 min. Intermediate 2(c) (1 g) in DMF (20 ml) was then added, followed by dicyclohexylcarbodiimide (0.66 g) and the mixture was stirred at room temperature for 16 h and then filtered. The filtrate was concentrated in vacuo, treated with dilute sodium hydroxide solution and extracted with dichloromethane. The organic layer was then washed with water, dried and evaporated to give a residue which was purified by column chromatography eluting with dichloromethane:methanol (97:3) to give a solid which was recrystallised from isopropanol and filtered off to give the title compound (0.4 g), m.p. 215°–225°.

Analysis Found: C,72.3; H,5.9; N,7.4; $C_{34}H_{33}N_3O_5$ requires: C,72.5; H,5.9; N,7.4%.

EXAMPLE 2

9,10-Dihydro-5-methoxy-9-oxo-N-[4-[[3-(1,2,3,4-tetrahydro-6,7-dimethoxy-2-isoquinolinyl)propyl]thio]phenyl]-4-acridinecarboxamide A mixture of 9,10-dihydro-5-methoxy-9-oxo-4-acridinecarboxylic acid (0.7 g) and 1-hydroxybenzotriazole (0.35 g) in DMF (20 ml) was stirred at room temperature for 10 min. Intermediate 2(b) (0.9 g) in DMF (20 ml) was then added, followed by dicyclohexylcarbodiimide (0.5 g) and the mixture was stirred at room temperature for 16 h and then filtered. The filtrate was concentrated in vacuo, treated with dilute sodium hydroxide solution and extracted with dichloromethane. The combined, dried organic extracts were evaporated to leave an oil which was purified by column chromatography eluting with dichloromethane:methanol (97:3). The resulting solid was recrystallised from acetonitrile and filtered off to give the title compound (0.26 g), m.p. 199°.

Analysis Found: C,67.7; H,5.9; N,6.6; S,5.2; $C_{35}H_{35}N_3O_5S(0.5\ H_2O)$ requires: C,67.9; H,5.9; N,6.8; S,5.2%.

EXAMPLE 3

9,10-Dihydro-5-methoxy-9-oxo-N-[4-[3-(1,2,3,4-tetrahydro-6,7-dimethoxy-2-isoquinolinyl)propoxy]phenyl]-4-acridinecarboxamide A mixture of 9,10-dihydro-5-methoxy-9-oxo-4-acridinecarboxylic acid (1.5 g) and 1-hydroxybenzotriazole (0.5 g) in DMF (30 ml) was stirred at room temperature for 10 min. Intermediate 2(a) (1.27 g) in DMF (20 ml) was then added, followed by dicyclohexylcarbodiimide (0.76 g) and the mixture was stirred at room temperature for 16 h and then filtered. The filtrate was concentrated in vacuo, treated with dilute sodium hydroxide solution and extracted with dichloromethane. The combined, dried organic extracts were evaporated to give a residue which was purified by column chromatography eluting with dichloromethane:methanol (97:3). The solid was recrystallised from isopropanol and filtered off to give the title compound (0.89 g), m.p. 190°.

Analysis Found: C,68.6; H,5.9; N,6.8; $C_{35}H_{35}N_3O_6$ requires: C,68.6; H,6.1; N,6.9%.

EXAMPLE 4

5-Fluoro-9,10-dihydro-9-oxo-N-[4-[[3-(1,2,3,4-tetrahydro-6,7-dimethoxy-2-isoquinolinyl)propyl]thio]phenyl]-4-acridinecarboxamide A mixture of 5-fluoro-9,10-dihydro-9-oxo-4-acridinecarboxylic acid (1 g) and 1-hydroxybenzotriazole (0.5 g) in DMF (30 ml) was stirred at room temperature for 10 min. Intermediate 2(b) (1.4 g) in DMF (20 ml) was then added, followed by dicyclohexylcarbodiimide (0.8 g) and the mixture was stirred at room temperature for 16 h and then filtered. The filtrate was concentrated in vacuo, treated with dilute sodium hydroxide solution and extracted with dichloromethane. The combined, dried organic extracts were evaporated to give a residue which was purified by column chromatography eluting with dichloromethane:methanol (97:3). The solid was recrystallised from isopropanol and filtered off to give the title compound (0.28 g), m.p. 162°.

Analysis Found: C,66.1; H,5.4; F,3.0; N,6.8; S,5.3; $C_{34}H_{32}FN_3O_4S$ requires: C,66.3; H,5.6; F,3.1; N,6.8; S,5.2%.

The following compounds were prepared in a similar manner to Examples 1 to 4.

EXAMPLE 5

9,10-Dihydro-5-methyl-9-oxo-N-[4-[[3-(1,2,3,4-tetrahydro-6,7-dimethoxy-2-isoquinolinyl)propyl]thio]phenyl]-4-acridinecarboxamide The coupling of 9,10-dihydro-5-methyl-9-oxo-4-acridinecarboxylic acid (1 g) with Intermediate 2(b) (1.4 g) gave, after crystallisation from isopropanol, the title compound (0.45 g), m.p. 155°.

Analysis Found: C,68.8; H,5.9; N,6.8; S,5.0; $C_{35}H_{35}N_3O_4S(H_2O)$ requires: C,68.7; H,6.1; N,6.8; S,5.2%.

EXAMPLE 6

9,10-Dihydro-9-oxo-N-[4-[3-(1,2,3,4-tetrahydro-6,7-dimethoxy-2-isoquinolinyl)propoxy]phenyl]-4-acridinecarboxamide The coupling of 9,10-dihydro-9-oxo-4-acridinecarboxylic acid (0.8 g) with Intermediate 2(a) (1.1 g) gave, after crystallisation from isopropanol, the title compound (0.27 g), m.p. 220°.

Analysis Found: C,71.4; H,5.9; N,7.3; $C_{34}H_{33}N_3O_5(0.5 H_2O)$ requires: C,71.3; H,6.0; N,7.3%.

EXAMPLE 7

9,10-Dihydro-9-oxo-N-[4-[2-(1,2,3,4-tetrahydro-6,7-dimethoxy-2-isoquinolinyl)ethoxy]phenyl]-4-acridinecarboxamide The coupling of 9,10-dihydro-9-oxo-4-acridinecarboxylic acid (0.37 g) with Intermediate 5(a) (0.51 g) gave, after crystallisation from isopropanol, the title compound (0.27 g), m.p. 154°.

Analysis Found: C,70.4; H,5.7; N,7.5; $C_{33}H_{31}N_3O_5(0.5 H_2O)$ requires: C,70.9; H,5.8; N,7.5%.

EXAMPLE 8

9,10-Dihydro-9-oxo-N-[4-[[3-(1,2,3,4-tetrahydro-6,7-dimethoxy-2-isoquinolinyl)propyl]thio]phenyl]-4-acridinecarboxamide The coupling of 9,10-dihydro-9-oxo-4-acridinecarboxylic acid (0.8 g) with Intermediate 2(b) (1 g) gave, after crystallisation from isopropanol, the title compound (0.04 g), m.p. 182°.

Analysis Found: C,67.3; H,5.6; N,6.9; S,5.25; $C_{34}H_{33}N_3O_4S(1.5 H_2O)$ requires: C,67.3; H,5.9; N,6.9; S,5.3%.

EXAMPLE 9

9,10-Dihydro-5-methyl-9-oxo-N-[4-[4-(1,2,3,4-tetrahydro-6,7-dimethoxy-2-isoquinolinyl)butyl]phenyl]-4-acridinecarboxamide The coupling of 9,10-dihydro-5-methyl-9-oxo-4-acridinecarboxylic acid (1 g) with Intermediate 2(d) (1.34 g) gave, after crystallisation from ethanol/acetone, the title compound (0.86 g), m.p. 140°.

Analysis Found: C,73.1; H,6.3; N,6.8; $C_{36}H_{37}N_3O_4 (H_2O)$ requires: C,72.8; H,6.5; N,7.1%.

EXAMPLE 10

9,10-Dihydro-5-methoxy-9-oxo-N-[4-[3-(1,2,3,4-tetrahydro-6,7-dimethoxy-2-isoquinolinyl)propyl]phenyl]-4-acridinecarboxamide The coupling of 9,10-dihydro-5-methoxy-9-oxo-4-acridinecarboxylic acid (0.65 g) with Intermediate 5(b) (0.53 g) gave, after crystallisation from isopropanol, the title compound (0.3 g), m.p. 135°.

Analysis Found: C,70.9; H,6.0; N,6.7; $C_{35}H_{35}N_3O_5 (H_2O)$ requires: C,70.6; H,6.3; N,7.05%.

EXAMPLE 11

9,10-Dihydro-5-methyl-9-oxo-N-[4-[3-(1,2,3,4-tetrahydro-6,7-dimethoxy-2-isoquinolinyl)propyl]phenyl]-4-acridinecarboxamide The coupling of 9,10-dihydro-5-methyl-9-oxo-4-acridinecarboxylic acid (0.61 g) with Intermediate 5(b) (0.53 g) gave, after crystallisation from isopropanol, the title compound (0.45 g), m.p. 120°.

Analysis Found: C,73.2; H,6.15; N,7.3; $C_{35}H_{35}N_3O_4 (0.5 H_2O)$ requires: C,73.7; H,6.35; N,7.4%.

EXAMPLE 12

5-Fluoro-9,10-dihydro-9-oxo-N-[4-[2-(1,2,3,4-tetrahydro-6,7-dimethoxy-2-isoquinolinyl)ethyl]phenyl]-4-acridinecarboxamide The coupling of 5-fluoro-9,10-dihydro-9-oxo-4-acridinecarboxylic acid (1 g) with Intermediate 2(c) (0.81 g) gave after crystallisation from acetonitrile/isopropanol (1:1), the title compound (0.2 g), m.p. 212°.

Analysis Found: C,69.4; H,5.2; N,7.8; $C_{33}H_{30}FN_3O_4(H_2O)$ requires: C,69.6; H,5.6; N,7.4%.

EXAMPLE 13

5-Fluoro-9,10-dihydro-9-oxo-N-[4-[3-(1,2,3,4-tetrahydro-6,7-dimethoxy-2-isoquinolinyl)propyl]phenyl]-4-acridinecarboxamide The coupling of 5-fluoro-9,10-dihydro-9-oxo-4-acridinecarboxylic acid (1 g) with Intermediate 5(b) (0.85 g) gave, after crystallisation from isopropanol, the title compound (0.4 g), m.p. 166°.

Analysis Found: C,70.3; H,5.4; N,7.2; $C_{34}H_{32}FN_3O_4(H_2O)$ requires: C,69.9; H,5.8; N,7.2%.

EXAMPLE 14

9,10-Dihydro-5-methyl-9-oxo-N-[4-[2-(1,2,3,4-tetrahydro-6,7-dimethoxy-2-isoquinolinyl)ethyl]phenyl]-4-acridinecarboxamide The coupling of 9,10-dihydro-5-methyl-9-oxo-4-acridinecarboxylic acid (0.63 g) with Intermediate 2(c) (0.62 g) gave, after crystallisation from ethanol, the title compound (0.2 g), m.p. 175°.

Analysis Found: C,71.8; N,6.2; N,7.2; $C_{34}H_{33}N_3O_4(H_2O)$ requires: C,72.2; H,6.2; N,7.4%.

EXAMPLE 15

9,10-Dihydro-N-[2-methoxy-4-[3-(1,2,3,4-tetrahydro-6,7-dimethoxy-2-isoquinolinyl)propyl]phenyl]-5-methyl-9-oxo-4-acridinecarboxamide A mixture of 9,10-dihydro-5-methyl-9-oxo-4-acridinecarboxylic acid (1 g) and 1-hydroxybenzotriazole (0.53 g) in DMF (30 ml) was stirred at room temperature for 10 min. Intermediate 16(a) (1.28 g) in DMF (20 ml) was then added, followed by dicyclohexylcarbodiimide (0.74 g) and the mixture was stirred at room temperature for 16 h and then filtered. The filtrate was concentrated in vacuo, treated with dilute sodium hydroxide solution and extracted with dichloromethane. The organic layer was then washed with water, dried and concentrated to give a residue which was purified by column chromatography eluting with dichloromethane:methanol (95:5) to give a solid which was recrystallised from ether to give the title compound (0.54 g), m.p. 174°.

Analysis Found: C,72.9; H,6.3; N,7.4; $C_{36}H_{37}N_3O_5$ requires: C,73.1; H,6.3; N,7.1%.

EXAMPLE 16

9,10-Dihydro-5-methoxy-N-[2-methoxy-4-[3-(1,2,3,4-tetrahydro-6,7-dimethoxy-2-isoquinolinyl)propyl]phenyl]-9-oxo-4-acridinecarboxamide A solution of Intermediate 16(a) (1.28 g) and dicyclohexylcarbodiimide (0.74 g) in DMF (20 ml) was added to a stirred solution of 9,10-dihydro-5-methoxy-9-oxo-4-acridinecarboxylic acid (1 g) and 1-hydroxybenzotriazole (0.5 g) in DMF (20 ml). The resulting mixture was stirred overnight at room temperature, filtered and concentrated in vacuo. The residue was taken up in dichloromethane, and then washed successively with dilute sodium hydroxide solution and water. The organic layer was then dried and evaporated to give a residue which was purified by column chromatography eluting with dichloromethane:methanol (9:1) to give a solid which was crystallised from ether to give the title compound (0.43 g), m.p. 188°.

Analysis Found: C,70.9; H,6.4; N,7.0; $C_{36}H_{37}N_3O_6$ requires: C,71.15; H,6.1; N,6.9%.

The following compounds were prepared in a similar manner to Examples 15 and 16.

EXAMPLE 17

5-Fluoro-9,10-dihydro-N-[2-methoxy-4-[3-(1,2,3,4-tetrahydro-6,7-dimethoxy-2-isoquinolinyl)propoxy]phenyl]-9-oxo-4-acridinecarboxamide The coupling of 5-fluoro-9,10-dihydro-9-oxo-4-acridinecarboxylic acid (0.31 g) with Intermediate 8(a) (0.4 g) gave, after crystallisation from isopropanol, the title compound (0.2 g), m.p. 152°.

Analysis Found: C,65.7; H,5.6; F,3.0; N,6.9; $C_{35}H_{34}FN_3O_6$ (1.5 $H_2O$) requires: C,65.8; H,5.8; F,2.9; N,6.6%.

EXAMPLE 18

9,10-Dihydro-5-methoxy-N-[2-methyl-4-[3-(1,2,3,4-tetrahydro-6,7-dimethoxy-2-isoquinolinyl)propoxy]phenyl]-9-oxo-4-acridinecarboxamide The coupling of 9,10-dihydro-5-methoxy-9-oxo-4-acridinecarboxylic acid (1.5 g) with Intermediate 8(b) (1.3 g) gave, after crystallisation from isopropanol/ethanol, the title compound (0.53 g), m.p. 160°.

Analysis Found: C,69.6; H,5.8; N,6.5; $C_{36}H_{37}N_3O_6$(0.5 $H_2O$) requires: C,70.1; H,6.2; N,6.8%.

EXAMPLE 19

9,10-Dihydro-5-methyl-N-[2-methyl-4-[3-(1,2,3,4-tetrahydro-6,7-dimethoxy-2-isoquinolinyl)propoxy]phenyl]-9-oxo-4-acridinecarboxamide The coupling of 9,10-dihydro-5-methyl-9-oxo-4-acridinecarboxylic acid (1 g) with Intermediate 8(b) (1.4 g) gave, after crystallisation from acetone, the title compound (0.73 g), m.p. 160°.

Analysis Found: C,71.0; H,6.1; N,6.5; $C_{36}H_{37}N_3O_5$ ($H_2O$) requires: C,70.9; H,6.4; N,6.9%.

EXAMPLE 20

9,10-Dihydro-5-methoxy-N-[2-methyl-4-[2-(1,2,3,4-tetrahydro-6,7-dimethoxy-2-isoquinolinyl)ethyl]phenyl]-9-oxo-4-acridinecarboxamide The coupling of 9,10-dihydro-5-methoxy-9-oxo-4-acridinecarboxylic acid (1.7 g) with Intermediate 16(c) (1.7 g) gave, after crystallisation from ethanol, the title compound (0.21 g), m.p. 200°–201°.

Analysis Found: C,71.9; H,5.9; N,6.9; $C_{35}H_{35}N_3O_5$(0.5 $H_2O$) requires: C,71.65; H,6.2; N,7.2%.

EXAMPLE 21

5-Fluoro-9,10-dihydro-N-[2-methyl-4-[2-(1,2,3,4-tetrahydro-6,7-dimethoxy-2-isoquinolinyl)ethyl]phenyl]-9-oxo-4-acridinecarboxamide The coupling of 5-fluoro-9,10-dihydro-9-oxo-4-acridinecarboxylic acid (1 g) with Intermediate 16(c) (1.25 g) gave, after crystallisation from ethanol, the title compound (0.32 g), m.p. 210°.

Analysis Found: C,71.2; H,5.9; F, 3.4; N,7.4; $C_{34}H_{32}FN_3O_4$ (0.5 $H_2O$) requires: C,71.1; H,5.8; F,3.3; N,7.3%.

EXAMPLE 22

9,10-Dihydro-N-[2-methoxy-4-[3-(1,2,3,4-tetrahydro-6,7-dimethoxy-2-isoquinolinyl)propoxy]phenyl]-5-methyl-9-oxo-4-acridinecarboxamide The coupling of 9,10-dihydro-5-methyl-9-oxo-4-acridinecarboxylic acid (0.7 g) with Intermediate 8(a) (1 g) gave, after crystallisation from acetonitrile, the title compound (0.83 g), m.p. 183°–184°.

Analysis Found: C,70.2; H,6.1; N,6.8; $C_{36}H_{37}N_3O_6$ (0.5 $H_2O$) requires: C,70.1; H,6.2; N,6.8%.

EXAMPLE 23

N-[2-Ethoxy-4-[3-(1,2,3,4-tetrahydro-6,7-dimethoxy-2-isoquinolinyl)propyl]phenyl]-9,10-dihydro-5-methoxy-9-oxo-4-acridinecarboxamide The coupling of 9,10-dihydro-5-methoxy-9-oxo-4-acridinecarboxylic acid (0.65 g) with Intermediate 16(b) (0.6 g) gave, after crystallisation from isopropanol/acetonitrile (9:1), the title compound (0.22 g), m.p. 198°.

Analysis Found: C,71.1; H,6.4; N,6.9; $C_{37}H_{39}N_3O_6$ requires: C,71.5; H,6.3; N,6.8%.

EXAMPLE 24

N-[2-Methoxy-4-[3-[[(3,4-dimethoxyphenyl)methyl]methyl-amino]propoxy]phenyl]-5-fluoro-9,10-dihydro-9-oxo-4-acridinecarboxamide A mixture of 5-fluoro-9,10-dihydro-9-oxo-4-acridinecarboxylic acid (1 g) and 1-hydroxybenzotriazole (0.5 g) in DMF (30 ml) was stirred at room temperature for 10 min. Intermediate 22(b) (1.2 g) in DMF (15 ml) was then added, followed by dicyclohexylcarbodiimide (0.5 g) and the mixture was stirred at room temperature for 16 h and then filtered. The filtrate was concentrated in vacuo, treated with dilute sodium hydroxide solution and extracted with dichloromethane. The combined, dried organic extracts were evaporated and the residue was purified by column chromatography eluting with dichloromethane- methanol (97:3). The solid was recrystallised from isopropanol to give the title compound (0.68 g). M.p. 108°.

Analysis Found: C 66.4; H 5.5; F 3.0; N 7.0; $C_{34}H_{34}FN_3O_6(H_2O)$ Requires: C 66.11; H 5.8; F 3.1; N 6.8%.

EXAMPLE 25

N-[2-Methyl-4-[3-[[(3,4-dimethoxyphenyl)methyl]methyl-amino]propoxy]phenyl]-5-fluoro-9,10-dihydro-9-oxo-4-acridinecarboxamide A mixture of 5-fluoro-9,10-dihydro-9-oxo-4-acridinecarboxylic acid (1 g) and 1-hydroxybenzotriazole (0.47 g) in DMF (30 ml) was stirred at room temperature for 10 min. Intermediate 22(a) (1.2 g) in DMF (15 ml) was then added, followed by dicyclohexylcarbodiimide (0.7 g) and the mixture was stirred at room temperature for 16 h and then filtered. The filtrate was concentrated in vacuo, treated with dilute sodium hydroxide solution and extracted with dichloromethane. The combined, dried organic extracts were evaporated and the residue was purified by column chromatography eluting with dichloromethane- methanol (98:2). The solid was then recrystallised from isopropanol to give the title compound (0.86 g). M.p. 130°.

Analysis Found: C 69.93; H 5.89; F 3.2; N 7.3; $C_{34}H_{34}FN_3O_5$ Requires: C 69.97; H 5.87; F 3.2; N 7.2%.

EXAMPLE 26

N-[2-Methoxy-4-[3-[[(3,4-dimethoxyphenyl)methyl]methyl-amino]propoxy]phenyl]-9,10-dihydro-5-methoxy-9-oxo-4-acridinecarboxamide A mixture of 9,10-dihydro-5-methoxy-9-oxo-4-acridinecarboxylic acid (1 g) and 1-hydroxybenzotriazole (0.62 g) in DMF (30 ml) was stirred at room temperature for 10 min. Intermediate 22(b) (1 g) in DMF (20 ml) was then added followed by dicyclohexylcarbodiimide (0.62 g) and the mixture was stirred at room temperature for 16 h and then filtered. The filtrate was concentrated in vacuo, treated with dilute sodium hydroxide solution and extracted with methylene chloride. The combined, dried organic extracts were evaporated and the residue was purified by column chromatography on silica gel, eluting with dichloromethane/methanol (97:3). After crystallization from isopropanol, the title compound was obtained as a solid (0.4 g). M.p. 146°.

Analysis Found: C68.4; H5.9; N6.7; $C_{35}H_{37}N_3O_7$ Requires: C68.7; H6.1; N6.9%.

In the same way, the following compounds were prepared:

EXAMPLE 27

N-[2-Methyl-4-[3-[[(3,4-dimethoxyphenyl)methyl]methyl-amino]propoxy]phenyl]-9,10-dihydro-5-methyl-9-oxo-4-acridinecarboxamide The coupling of 9,10-dihydro-5-methyl-9-oxo-4-acridine carboxylic acid (1 g) with Intermediate 22(a) (1.23 g) gave, after crystallization from isopropanol, the title compound as a solid (1.2 g). M.p. 146°.

Analysis Found: C 72.5; H 6.5; N 7.1; $C_{35}H_{37}N_3O_5$ Requires: C 72.5; H 6.4; N 7.2%.

EXAMPLE 28

N-[2-Methyl-4-[3-[[(3,4-dimethoxyphenyl)methyl]methyl-amino]propoxy]phenyl]-9,10-dihydro-9-oxo-4-acridinecarboxamide The coupling of 9,10-dihydro-9-oxo-4-acridinecarboxylic acid (0.9 g) with Intermediate 22(a) (1.2 g) gave, after crystallization from isopropanol, the title compound as a solid (1.3 g). M.p. 145°–150°.

NMR includes d 2.2 and 2.3 (2s,2×3H,N—$CH_3$ and $CH_3$—Ar), 3.4(s,2H,$CH_2$—Ar), 3.7(s,6H,$OCH_3$), 6.6–8.5(m,13H, aromatics).

EXAMPLE 29

N-[2-Methyl-4-[2-[[(3,4-dimethoxyphenyl)methyl]methylamino]ethoxy]phenyl]-9,10-dihydro-5-methoxy-9-oxo-4-acridinecarboxamide The coupling of 9,10-dihydro-5-methoxy-9-oxo-4-acridine carboxylic acid (1.2 g) with Intermediate 22(d) (1.12 g) gave, after crystallization from ethanol, the title compound as a solid (0.6 g). M.p. 178°–179°.

Analysis Found: C 70.1; H 6.1; N 7.1; $C_{34}H_{35}N_3O_6$ Requires: C 70.2; H 6.1; N 7.2%.

EXAMPLE 30

N-[2-Ethyl-4-[3-[[(3,4-dimethoxyphenyl)methyl]methyl-amino]propoxy]phenyl]-5-fluoro-9,10-dihydro-9-oxo-4-acridinecarboxamide The coupling of 5-fluoro-9,10-dihydro-9-oxo-4-acridine carboxylic acid (1 g) with Intermediate 22(c) (1.2 g) gave, after crystallization from isopropanol, the title compound as a solid (0.95 g). M.p. 146°.

Analysis Found: C 70.3; H 6.1; F 3.2; N 7.0; $C_{35}H_{36}FN_3O_5$ Requires: C 70.3; H 6.1; F 3.1; N 7.0%.

EXAMPLE 31

N-[2-Methoxy-4-[3-[[(3,4-dimethoxyphenyl)methyl]methyl-amino]propoxy]phenyl]-9,10-dihydro-5-methyl-9-oxo-4-acridinecarboxamide The coupling of 9,10-dihydro-5-methyl-9-oxo-4-acridine carboxylic acid (0.8 g) with Intermediate 22(b) (1.14 g) gave, after crystallization from isopropanol, the title compound as a solid (0.4 g). M.p. 156°–157°.

Analysis Found: C 70.6; H 6.3; N 7.15; $C_{35}H_{37}N_3O_6$ Requires: C 70.6; H 6.3; N 7.05%.

EXAMPLE 32

N-[2-Methyl-4-[2-[[(3,4-dimethoxyphenyl)methyl]methyl-amino]ethyl]phenyl]-5-fluoro-9,10-dihydro-9-oxo-4-acridinecarboxamide The coupling of 5-fluoro-9,10-dihydro-9-oxo-4-acridine carboxylic acid (0.82 g) with Intermediate 27(a) (1.07 g) gave, after crystallization from ethanol, the title compound as a yellow solid (0.21 g). M.p. 125°.

Analysis Found: C 68.3; H 5.8; F 3.3; N 7.2; $C_{33}H_{32}FN_3O_4$ (1.5 $H_2O$) Requires: C 68.3; H 6.1; F 3.3; N 7.2%.

EXAMPLE 33

N-[2-Methyl-4-[2-[[(3,4-dimethoxyphenyl)methyl]methyl-amino]ethyl]phenyl]-9,10-dihydro-5-methyl-9-oxo-4-acridinecarboxamide The coupling of 9,10-dihydro-5-methyl-9-oxo-4-acridine carboxylic acid (0.8 g) with Intermediate 27(a) (1 g) gave, after crystallization from ethanol, the title compound as a yellow solid (0.45 g). M.p. 160°–161°.

Analysis Found: C 73.4; H 6.3; N 7.5; $C_{34}H_{35}N_3O_4$ (0.5 $H_2O$) Requires: C 73.1; H 6.5; N 7.5%.

EXAMPLE 34

N-[2-Methoxy-4-[2-[[(3,4-dimethoxyphenyl)methyl]methyl amino]ethyl]phenyl]-5-fluoro-9,10-dihydro-9-oxo-4-acridinecarboxamide The coupling of 5-fluoro-9,10-dihydro-9-oxo-4-acridine carboxylic acid (1 g) with Intermediate 27(b) (1.3 g) gave, after crystallization from ethanol, the title compound as a solid (0.55 g). M.p. 161°–162°.

Analysis Found: C69.3; H5.8; N7.5; $C_{33}H_{32}FN_3O_5$ Requires: C69.6; H5.6; N7.4%

EXAMPLE 35

N-[2-Methyl-4-[3-[[(3,4-dimethoxyphenyl)methyl]methyl-amino]propyl]phenyl]-9,10-dihydro-5-methoxy-9-oxo-4-acridinecarboxamide The coupling of 9,10-dihydro-5-methoxy-9-oxo-4-acridine carboxylic acid (0.69 g) with Intermediate 27(c) (0.65 g) gave, after crystallization from isopropanol, the title compound as a solid (0.185 g). M.p. 154°.

Analysis Found: C 72.65; H 6.4; N 7.0; $C_{35}H_{37}N_3O_5$ Requires: C 72.5; H 6.4; N 7.25%.

EXAMPLE 36

N-[2-Methyl-4-[3-[[(3,4-dimethoxy-phenyl)methyl]methylamino]propyl]phenyl]-5-fluoro-9,10-dihydro-9-oxo-4-acridinecarboxamide The coupling of 5-fluoro-9,10-dihydro-9-oxo-4-acridine carboxylic acid (0.5 g) with Intermediate 27(c) (0.59 g) gave, after crystallization from isopropanol, the title compound as a solid (0.26 g). M.p. 132°.

Analysis Found: C 71.9; H 6.0; F 3.3; N 7.3; $C_{34}H_{34}FN_3O_4$ Requires: C 71.9; H 6.0; F 3.3; N 7.45%.

EXAMPLE 37

N-[2-Methoxy-4-[3-[[(3,4-dimethoxy-phenyl)methyl]methylamino]propyl]phenyl]-9,10-dihydro-5-methoxy-9-oxo-4-acridinecarboxamide The coupling of 9,10-dihydro-5-methoxy-9-oxo-4-acridine carboxylic acid (0.43 g) and Intermediate 30 (0.5 g) gave, after crystallization from isopropanol, the title compound as a solid (0.16 g). M.p. 105°.

Analysis Found: C 70.6; H 6.3; N 6.9; $C_{35}H_{37}N_3O_6$ Requires: C 70.6; H 6.3; N 7.0%.

EXAMPLE 38

N-[2-Methoxy-4-[3-[[(3,4-dimethoxy-phenyl)methyl]methylamino]propyl]phenyl]-5-fluoro-9,10-dihydro-9-oxo-4-acridinecarboxamide The coupling of 5-fluoro-9,10-dihydro-9-oxo-4-acridine carboxylic acid (0.4 g) with Intermediate 30 (0.5 g) gave, after crystallization from ethanol/cyclohexane, the title compound as a solid (0.26 g). m.p. 170°–190°.

Analysis Found: C67.7; H5.7; N6.6; $C_{34}H_{34}FN_3O_5, H_2O$ Requires: C67.9; H6.0; N7.0%.

EXAMPLE 39

N-[4-[4-[[(3,4-Dimethoxyphenyl)methyl]methyl amino]butyl]phenyl]-5-fluoro-9,10-dihydro-9-oxo-4-acridinecarboxamide A mixture of 5-fluoro-9,10-dihydro-9-oxo-4-acridinecarboxylic acid (0.42 g) and 1-hydroxybenzotriazole (0.27 g) in DMF (30 ml) was stirred at room temperature for 10 min. Intermediate 33(a) (0.55 g) in DMF (30 ml) was then added, followed by dicyclohexylcarbodiimide (0.34 g), and the mixture was stirred at room temperature for 16 h and then filtered. The filtrate was concentrated in vacuo, treated with dilute sodium hydroxide solution, and extracted with dichloromethane. The combined, dried, organic extracts were evaporated to leave an oil which was purified by column chromatography eluting with dichloromethane/methanol (95:5) to give an oil which was crystallised from ethanol and filtered off to give the title compound (0.32 g), MP: 131°.

Analysis Found: C,71.4; H,5.9; N,7.3; $C_{34}H_{34}FN_3O_4$ Requires: C,71.9; H,6.0; N,7.4%.

EXAMPLE 40

N-[4-[2-[[(3,4-Dimethoxyphenyl)methyl]methylamino]ethyl]phenyl]-9,10-dihydro-5-methoxy-9-oxo-4-acridinecarboxamide A mixture of 9,10-dihydro-5-methoxy-9-oxo-4-acridinecarboxylic acid (0.8 g) and 1-hydroxybenzotriazole (0.41 g) in DMF (50 ml) was stirred at room temperature for 10 min. Intermediate 33(b) (0.9 g) in DMF (30 ml) was then added, followed by dicyclohexylcarbodiimide (0.62 g), and the mixture was stirred at room temperature for 16 h and then filtered. The filtrate was concentrated in vacuo, treated with dilute sodium hydroxide solution, and extracted with dichloromethane. The combined, dried, organic extracts were evaporated to leave an oil which was purified by column chromatography eluting with dichloromethane/methanol (95:5) to give a solid. This was crystallised from isopropanol and filtered off to give the title compound (0.31 g), MP: 172°.

Analysis Found: C,71.3; H,6.0; N,7.35; $C_{33}H_{33}N_3O_5$ Requires: C,71.8; H,6.0; N,7.6%.

EXAMPLE 41

N-[4-[4-[[(3,4-Dimethoxyphenyl)methyl]methyl amino]butyl]phenyl]-9,10-dihydro-9-oxo-4-acridinecarboxamide A mixture of 9,10-dihydro-9-oxo-4-acridinecarboxylic acid (4 g) and 1-hydroxybenzotriazole (2.83 g) in DMF (50 ml) was stirred at room temperature for 10 min. Intermediate 33(a) (5.5 g) in DMF (100 ml) was then added, followed by dicyclohexylcarbodiimide (3.45 g), and the mixture was stirred at room temperature for 16 h and then filtered. The filtrate was concentrated in vacuo, treated with dilute sodium hydroxide solution, and extracted with dichloromethane. The combined, dried, organic extracts were evaporated to leave an oil which was purified by column chromatography eluting with dichloromethane/methanol (95:5) to give a solid. This was crystallised from methanol and then filtered off to give the title compound (3.2 g), MP: 140°.

Analysis Found: C,74.3; H,6.5; N,7.7; $C_{34}H_{35}N_3O_4$ Requires: C,74.3; H,6.4; N,7.6%.

EXAMPLE 42

N-[4-2-[[(3,4-Dimethoxyphenyl)methyl]methylamino]ethyl]phenyl]-9,10-dihydro-9-oxo-4-acridinecarboxamide A mixture of 9,10-dihydro-9-oxo-4-acridinecarboxylic acid (0.8 g) and 1-hydroxybenzotriazole (0.56 g) in DMF (50 ml) was stirred at room temperature for 10 min. Intermediate 33(b) (1 g) in DMF (10 ml) was then added followed by dicyclohexylcarbodiimide (0.7 g). The mixture was stirred at room temperature for 16 h and then filtered. The filtrate was concentrated in vacuo, treated with dilute sodium hydroxide solution and extracted with dichloromethane. The combined, dried organic extracts were evaporated to leave an oil which was purified by column chromatography eluting with dichloromethanemethanol (9:1) to give a solid. This solid was crystallised from acetonitrile and filtered off to give the title compound (0.35 g), MP: 172°.

Analysis Found: C,73.6; H,6.0; N,8.0; $C_{32}H_{31}N_3O_4$ Requires: C,73.7; N,6.0; N,8.1%.

The following compounds were prepared in a similar manner to Examples 39 to 42:

EXAMPLE 43

N-[4-[[3-[[(3,4-Dimethoxyphenyl)methyl]methylamino]propyl]thio]phenyl]-9,10-dihydro-9-oxo-4-acridinecarboxamide The coupling of 9,10-dihydro-9-oxo-4-acridinecarboxylic acid (0.8 g) with Intermediate 38(d) (1.16 g) gave, after crystallisation from ethanol, the title compound (0.28 g), MP: 140°.

Analysis Found: C,69.7; H,5.7; N,7.5; $C_{33}H_{33}N_3O_4S$ Requires: C,69.8; H,5.9; N,7.4%.

EXAMPLE 44

N-[4-[2-[(Phenylmethyl)methylamino]ethoxy]phenyl]-9,10-dihydro-9-oxo-4-acridinecarboxamide The coupling of 9,10-dihydro-9-oxo-4-acridinecarboxylic acid (1 g) with Intermediate 36(c) (1 g) gave, after crystallisation from ethanol, the title compound (0.8 g), MP: 173°.

Analysis Found: C,75.5; H,5.6; N,8.8; $C_{30}H_{27}N_3O_3$ Requires: C,75.45; H,5.7; N,8.8%.

EXAMPLE 45

N-[4-[3-[[2-(3,4-Dimethoxyphenyl)ethyl]methylamino]propoxy]phenyl]-9,10-dihydro-9-oxo-4-acridinecarboxamide The coupling of 9,10-dihydro-9-oxo-4-acridinecarboxylic acid (1 g) with Intermediate 38(a) (1.44 g) gave, after crystallisation from ethanol, the title compound (0.82 g), MP: 140°.

Analysis Found: C,71.7; H,6.3; N,7.4; $C_{34}H_{35}N_3O_5$ Requires: C,72.2; H,6.2; N,7.4%.

EXAMPLE 46

N-[4-[3-[[(3,4-Dimethoxyphenyl)methyl]methylamino]propoxy]phenyl]-9,10-dihydro-5-methoxy-9-oxo-4-acridinecarboxamide The coupling of 9,10-dihydro-5-methoxy-9-oxo-4-acridinecarboxylic acid (2 g) with Intermediate 38(c) (2.4 g) gave, after crystallisation from isopropanol, the title compound (1.2 g), MP: 180°.

Analysis Found: C,70.1; H,6.1; N,7.2; $C_{34}H_{35}N_3O_6$ requires: C,70.2; H,6.1; N,7.2%.

EXAMPLE 47

N-[4-[2-[[2-(4-Methoxyphenyl)ethyl]methyl-
amino]ethoxy]phenyl]-9,10-
dihydro-9-oxo-4-acridinecarboxamide The coupling of 9,10-dihydro-9-oxo-4-acridinecarboxylic acid (0.8 g) with Intermediate 36(e) (0.9 g) gave, after crystallisation from ethanol, the title compound (0.7 g), MP: 165°.

Analysis Found: C,73.6;H,6.0; N,8.0; $C_{32}H_{31}N_3O_4$ Requires: C,73.7; H,6.0; N,8.1%.

EXAMPLE 48

N-[4-[3-[[2-(4-Methoxyphenyl)ethyl]methyl-
amino]propoxy]phenyl]-9,10-
dihydro-9-oxo-4-acridinecarboxamide The coupling of 9,10-dihydro-9-oxo-4-acridinecarboxylic acid (0.8 g) with Intermediate 38(b) (0.94 g) gave, after crystallisation from ethanol, the title compound (0.9 g), MP: 160°.

Analysis Found: C,73.9; H,6.2; N,7.8; $C_{33}H_{33}N_3O_4$ Requires: C,74.0; H,6.2; N,7.8%.

EXAMPLE 49

N-[4-[2-[[(4-Methoxyphenyl)methyl]methyl
amino]ethoxy]phenyl]-9,10-
dihydro-9-oxo-4-acridinecarboxamide The coupling of 9,10-dihydro-9-oxo-4-acridinecarboxylic acid (0.6 g) with Intermediate 36(f) (0.72 g) gave, after crystallisation from methanol, the title compound (0.18 g), MP: 146°.

Analysis Found: C,73.5; H,5.8; N,8.1; $C_{31}H_{29}N_3O_4$ Requires: C,73.35; H,5.8; N,8.3%.

EXAMPLE 50

N-[4-[2-[[(4-Methylphenyl)methyl]methyl-
amino]ethoxy]phenyl]-9,10-
dihydro-9-oxo-4-acridinecarboxamide The coupling of 9,10-dihydro-9-oxo-4-acridinecarboxylic acid (0.7 g) with Intermediate 36(g) (0.78 g) gave, after crystallisation from isopropanol, the title compound (0.23 g), MP: 168°.

Analysis Found: C,75.3; H,6.0; N,8.1; $C_{31}H_{29}N_3O_3$ Requires: C,75.7; H,5.95; N,8.55%.

EXAMPLE 51

N-[4-[2-[[(3,4-Dimethoxyphenyl)methyl]methyl-
amino]ethoxy]phenyl]-9,10-
dihydro-9-oxo-4-acridinecarboxamide The coupling of 9,10-dihydro-9-oxo-4-acridinecarboxylic acid (1 g) with Intermediate 36(b) (1.25 g) gave, after crystallisation from ethanol, the title compound (1.39 g), MP: 140°.

Analysis Found: C,71.7; H,6.2; N,7.7; $C_{32}H_{31}N_3O_5$ Requires: C,71.5; H,5.8; N,7.8%.

EXAMPLE 52

N-[4-[2-[[[4-(Methylthio)phenyl]methyl]methyl-
amino]ethoxy]phenyl]-9,10-
dihydro-9-oxo-4-acridinecarboxamide The coupling of 9,10-dihydro-9-oxo-4-acridinecarboxylic acid (0.8 g) with Intermediate 36(h) (1 g) gave, after crystallisation from ethanol, the title compound (0.75 g), MP: 150°.

Analysis Found: C,71.1; H,5.6; N,7.9; S,5.8; $C_{31}H_{29}N_3O_3S$ Requires: C,71.1; H,5.6; N,8.0; S,6.1%.

EXAMPLE 53

N-[4-[2-[[(3,4-Dimethoxyphenyl)methyl]methyl-
amino]ethoxy]phenyl]-9,10-
dihydro-2-(methylthio)-9-oxo-4-
acridinecarboxamide The coupling of Intermediate 39 (0.7 g) with Intermediate 36(b) (0.81 g) gave, after crystallisation from ethanol, the title compound (0.45 g), MP: 170°.

Analysis Found: C,68.1; H,5.65; N,7.0; S,5.4; $C_{33}H_{33}N_3O_5S$ Requires: C,67.9; H,5.7; N,7.2; S,5.5%.

EXAMPLE 54

N-[4-[2-[[(3,4-Dimethoxyphenyl)methyl]methyl-
amino]ethoxy]phenyl]-9,10-
dihydro-7-(methylthio)-9-oxo-
4-acridinecarboxamide The coupling of 9,10-dihydro-7-(methylthio)-9-oxo-4-acridinecarboxylic acid (0.7 g) with Intermediate 36(b) (0.81 g) gave, after crystallisation from acetonitrile, the title compound (0.14 g), MP: 160°.

Analysis Found: C,67.8; H,5.8; N,7.1; S,5.4; $C_{33}H_{33}N_3O_5S$ Requires: C,67.9; H,5.7; N,7.2; S,5.5%.

EXAMPLE 55

N-[4-[2-[[2-(3,4-Dimethoxyphenyl)ethyl]methyl-
amino]ethoxy]phenyl]-9,10-
dihydro-2-(methylthio)-9-oxo-
4-acridinecarboxamide The coupling of Intermediate 39 (0.8 g) with Intermediate 36(a) (0.93 g) gave, after crystallisation from ethanol the title compound (0.46 g), MP: 150°.

Analysis Found: C,68.0; H,5.8; N,7.0; S,5.1; $C_{34}H_{35}N_3O_5S$ Requires: C,68.3; H,5.9; N,7.0; S,5.4%.

EXAMPLE 56

N-[4-[2-[[2-(3,4-Dimethoxyphenyl)ethyl]methyl-
amino]ethoxy)phenyl]-9,10-
dihydro-10-methyl-9-oxo-
4-acridinecarboxamide The coupling of 9,10-dihydro-10-methyl-9-oxo-4-acridinecarboxylic acid (0.72 g) with Intermediate 36(a) (0.9 g) gave, after crystallisation from isopropanol, the title compound (0.8 g), MP: 139°.

Analysis Found: C,72.25; H,6.2; N,7.4; $C_{34}H_{35}N_3O_5$ Requires: C,72.2; H,6.2; N,7.4%.

EXAMPLE 57

N-[4-[2-[[(3,4-Dimethoxyphenyl)methyl]methyl-
amino]ethoxy]phenyl]-9,10-
dihydro-5-methoxy-9-oxo-4-
acridinecarboxamide The coupling of 9,10-dihydro-5-methoxy-9-oxo-acridinecarboxylic acid (0.8 g) with Intermediate 36(b) (0.94 g) gave, after crystallisation from ethanol, the title compound (0.25 g), MP: 184°.

Analysis Found: C,69.9; H,6.0; N,7.4; $C_{33}H_{33}N_3O_6$ Requires: C,69.8; H,5.9; N,7.4%.

EXAMPLE 58

N-[4-[2-[[2-(3,4-Dimethoxyphenyl)ethyl]methyl-
amino]ethoxy]phenyl]-9,10-
dihydro-5-methoxy-9-oxo-4-
acridinecarboxamide The coupling of 9,10-dihydro-5-methoxy-9-oxo-4-acridinecarboxylic acid (0.8 g) with Intermediate 36(a) (0.98 g) gave, after crystallisation from ethanol the title compound (0.25 g), MP: 190°.

Analysis Found: C,70.0; H,6.1; N,7.3; $C_{34}H_{35}N_3O_6$ Requires: C,70.2; H,6.1; N,7.2%.

EXAMPLE 59

N-[4-[3-[[(3,4-Dimethoxyphenyl)methyl]methyl-
amino]propoxy]phenyl]-9,10-
dihydro-9-oxo-4-acridinecarboxamide The coupling of 9,10-dihydro-9-oxo-4-acridinecarboxylic acid (1 g) with Intermediate 38(c) (1.4 g) gave, after crystallisation from ethanol, the title compound (0.8 g), MP: 130°. IR includes signals at 1650 (CONH), 1620 (CO) and 3350 cm$^{-1}$ (NH).

EXAMPLE 60

N-[4-[3-[[(3,4-Dimethoxyphenyl)methyl]methyl-
amino]propoxy]phenyl]-5-
fluoro-9,10-dihydro-9-oxo-
4-acridinecarboxamide The coupling of 5-fluoro-9,10-dihydro-9-oxo-4-acridinecarboxylic acid (0.8 g) with Intermediate 38(c) (1 g) gave, after crystallisation from ethanol, the title compound (0.52 g), MP: 150°.

Analysis Found: C,69.6; H,5.7; F,3.25; N,7.3; $C_{33}H_{32}FN_3O_5$ Requires: C,69.6; H,5.7; F,3.3; N,7.4%.

EXAMPLE 61

N-[4-[2-[[2-(3,4-Dimethoxyphenyl)ethyl]methyl-
amino]ethyl]phenyl]-9,10-
dihydro-9-oxo-4-acridinecarboxamide The coupling of 9,10-dihydro-9-oxo-4-acridinecarboxylic acid (0.76 g) with Intermediate 33(e) (1 g) gave, after crystallisation from acetonitrile, the title compound (0.7 g), MP: 180°.

Analysis Found: C,73.5; H,6.1; N,7.9; $C_{33}H_{33}N_3O_4$ Requires: C,74.0; H,6.2; N,7.8%.

EXAMPLE 62

N-[4-4-[[[4-(Methylthio)phenyl]methyl]methyl-
amino]butyl]phenyl]-9,10-
dihydro-9-oxo-4-acridinecarboxamide The coupling of 9,10-dihydro-9-oxo-4-acridinecarboxylic acid (0.8 g) with Intermediate 33(j) (1 g) gave, after crystallisation from acetonitrile, the title compound (0.64 g), MP: 135°.

Analysis Found: C,73.7; H,6.2; N,7.9; S,5.7; $C_{33}H_{33}N_3O_2S$ Requires: C,74.0; H,6.2; N,7.8; S,6.0%.

EXAMPLE 63

N-[4-[4-[[(4-Fluorophenyl)methyl]methyl-
amino]butyl]phenyl]-9,10--
dihydro-9-oxo-4-acridinecarboxamide The coupling of 9,10-dihydro-9-oxo-4-acridinecarboxylic acid (0.7 g) with Intermediate 33(i) (0.86 g) gave, after crystallisation from acetonitrile, the title compound (0.43 g), MP: 151°.

Analysis Found: C,75.9; H,6.0; F,3.7; N,8.25; $C_{32}H_{30}FN_3O_2$ Requires: C,75.7; H,5.9; F,3.7; N,8.3%.

EXAMPLE 64

N-[4-[3-[[(4-Methoxyphenyl)methyl]methyl-
amino]propyl]phenyl]-9,10-
dihydro-9-oxo-4-acridinecarboxamide The coupling of 9,10-dihydro-9-oxo-4-acridinecarboxylic acid (0.72 g) with Intermediate 33(g) (0.85 g) gave, after crystallisation from isopropanol, the title compound (0.64 g), MP: 155°.

Analysis Found: C,76.2; H,6.1; N,7.9; $C_{32}H_{31}N_3O_3$ Requires: C,76.0; H,6.2; N,8.3%.

EXAMPLE 65

N-[4-[4-[[2-(4-Methoxyphenyl)ethyl]methyl-
amino]butyl]phenyl]-9,10-
dihydro-9-oxo-4-acridinecarboxamide The coupling of 9,10-dihydro-9-oxo-4-acridinecarboxylic acid (0.8 g) with Intermediate 33(h) (1 g) gave, after crystallisation from acetonitrile, the title compound (0.53 g), MP: 143°.

Analysis Found: C,76.4; H,6.6; N,7.8; $C_{34}H_{35}N_3O_3$ Requires: C,76.5; H,6.6; N,7.9%.

EXAMPLE 66

N-[4-[3-[[2-(3,4-Dimethoxyphenyl)ethyl]methyl-
amino]propyl]phenyl]-9,10-
dihydro-9-oxo-4-acridinecarboxamide The coupling of 9,10-dihydro-9-oxo-4-acridinecarboxylic acid (0.8 g) with Intermediate 33(d) (1 g) gave, after trituration with ether, the title compound (0.88 g), MP: 114°.

Analysis Found: C,74.2; H,6.35; N,7.55; $C_{34}H_{35}N3O_4$ Requires: C,74.3; H,6.4; N,7.6%.

EXAMPLE 67

N-[4-[4-[[2-(3,4-Dimethoxyphenyl)ethyl]methyl-amino]butyl]phenyl]-9,10-dihydro-9-oxo-4-acridinecarboxamide The coupling of 9,10-dihydro-9-oxo-4-acridinecarboxylic acid (0.72 g) with Intermediate 33(c) (1 g) gave, after crystallisation from acetonitrile, the title compound (0.12 g), MP: 120°.

Analysis Found: C,74.2; H,6.5; N,7.6; $C_{35}H_{37}N_3O_4$ Requires: C,74.6; H,6.6; N,7.45%.

EXAMPLE 68

N-[4-[2-[[2-(4-Methoxyphenyl)ethyl]methyl-amino]ethyl]phenyl]-9,10-dihydro-9-oxo-4-acridinecarboxamide The coupling of 9,10-dihydro-9-oxo-4-acridinecarboxylic acid (0.8 g) with Intermediate 33(k) (0.95 g) gave, after crystallisation from acetonitrile, the title compound (0.4 g), MP: 179°.

Analysis Found: C,76.0; H,6.1; N,8.1; $C_{32}H_{31}N_3O_3$ Requires: C,76.0; H,6.2; N,8.3%.

EXAMPLE 69

N-[4-[3-[[(3,4-Dimethoxyphenyl)methyl]methyl-amino]propyl]phenyl]-9,10-dihydro-9-oxo-4-acridinecarboxamide The coupling of 9,10-dihydro-9-oxo-4-acridinecarboxylic acid (0.8 g) with Intermediate 33(f) (1 g) gave, after crystallisation from acetonitrile, the title compound (1 g), MP: 112°.

Analysis Found: C,74.1; H,6.2; N,7.7; $C_{33}H_{33}N_3O_4$ Requires: C,74.0; H,6.2; N,7.8%.

EXAMPLE 70

N-[4-[5-[[(3,4-Dimethoxyphenyl)methyl]methyl-amino]pentyl]phenyl]-9,10-dihydro-9-oxo-4-acridinecarboxamide The coupling of 9,10-dihydro-9-oxo-4-acridinecarboxylic acid (0.8 g) with Intermediate 33(l) (1.15 g) gave, after trituration with ether, the title compound (0.41 g), MP: 110°.

Analysis Found: C,74.3; H,6.6; N,7.4; $C_{35}H_{37}N_3O_4$ Requires: C,74.6; H,6.6; N,7.45%.

EXAMPLE 71

N-[4-[4-[[2-(3,4-Dimethoxyphenyl)ethyl]methyl-amino]butyl]phenyl]-9,10-dihydro-7-methoxy-9-oxo-4-acridinecarboxamide The coupling of 9,10-dihydro-7-methoxy-9-oxo-4-acridinecarboxylic acid (1 g) with Intermediate 33(c) (1.3 g) gave, after crystallisation from ethanol, the title compound (0.85 g), MP: 155°.

Analysis Found: C,72.7; H,6.9; N,7.05; $C_{36}H_{39}N_3O_5$ Requires: C,72.8; H,6.6; N,7.1%.

EXAMPLE 72

N-[4-[4-[[(3,4-Dimethoxyphenyl)methyl]methyl-amino]butyl]phenyl]-9,10-dihydro-5-methoxy-9-oxo-4-acridinecarboxamide The coupling of 9,10-dihydro-5-methoxy-9-oxo-4-acridinecarboxylic acid (0.8 g) with Intermediate 33(a) (0.98 g) gave, after crystallisation from isopropanol, the title compound (0.12 g), MP: 157°.

Analysis Found: C,71.9; H,6.4; N,7.2; $C_{35}H_{37}N_3O_5$ Requires: C,72.5; H,6.4; N,7.25%.

EXAMPLE 73

N-[4-[3-[[(3,4-Dimethoxyphenyl)methyl]methyl-amino]propyl]phenyl]-5-fluoro-9,10-dihydro-9-oxo-4-acridinecarboxamide The coupling of 5-fluoro-9,10-dihydro-9-oxo-4-acridinecarboxylic acid (0.72 g) with Intermediate 33(f) (0.9 g) gave, after crystallisation from ethanol, the title compound (0.89 g), MP: 158°.

Analysis Found: C,71.9; H,6.1; F,3.25; N,7.7; $C_{33}H_{32}FN_3O_4$ Requires: C,71.65; H,5.8; F,3.4; N,7.6%.

EXAMPLE 74

N-[4-[2-[[(3,4-Dimethoxyphenyl)methyl]methyl-amino]ethyl]phenyl]-5-fluoro-9,10-dihydro-9-oxo-4-acridinecarboxamide The coupling of 5-fluoro-9,10-dihydro-9-oxo-4-acridinecarboxylic acid (1 g) with Intermediate 33(b) (1.2 g) gave, after crystallisation from ethanol, the title compound (0.78 g), MP: 175°.

Analysis Found: C,69.9; H,5.5; F,3.1; N,7.45; $C_{32}H_{30}FN_3O_4$ (0.5 $H_2O$) Requires: C,70.1; H,5.7; F,3.5; N,7.65%.

EXAMPLE 75

N-[4-[4-[[(3,4-Dimethoxyphenyl)methyl]methyl-amino]butyl]phenyl]-9,10-dihydro-5-nitro-9-oxo-4-acridinecarboxamide The coupling of 9,10-dihydro-5-nitro-9-oxo-4-acridinecarboxylic acid (0.6 g) with Intermediate 33(a) (0.7 g) gave, after crystallisation from acetonitrile, the title compound (0.35 g), MP: 174°.

Analysis Found: C,68.6; H,5.7; N,9.5; $C_{34}H_{34}N_4O_6$ Requires: C,68.7; H,5.8; N,9.4%.

EXAMPLE 76

N-[4-[2-[[(3,4-Dimethoxyphenyl)methyl]methyl-amino]ethyl]phenyl]-9,10-dihydro-5-nitro-9-oxo-4-acridinecarboxamide The coupling of 9,10-dihydro-5-nitro-9-oxo-4-acridinecarboxylic acid (0.6 g) with Intermediate 33(b) (0.63 g) gave, after crystallisation from isopropanol, the title compound (0.45 g), MP: 197°.

Analysis Found: C,67.4; H,5.3; N,9.7; $C_{32}H_{30}N_4O_6$ Requires: C,67.8; H,5.3; N,9.9%.

EXAMPLE 77

N-[4-[5-[[(3,4-Dimethoxyphenyl)methyl]methyl-amino]pentyl]phenyl]-5-fluoro-9,10-dihydro-9-oxo-4-acridinecarboxamide The coupling of 5-fluoro-9,10-dihydro-9-oxo-4-acridinecarboxylic acid (0.8 g) with Intermediate 33(l) (1 g) gave, after crystallisation from acetonitrile, the title compound (0.29 g), MP: 130°.

Analysis Found: C,71.9; H,6.2; F,3.2; N,7.1; $C_{35}H_{36}FN_3O_4$ Requires: C,72.3; H,6.2; F,3.3; N,7.2%.

EXAMPLE 78

N-[4-[4-[[2-(4-Methoxyphenyl)ethyl)methyl-amino]butyl]phenyl]-9,10-dihydro-5-methoxy-9-oxo-4-acridinecarboxamide The coupling of 9,10-dihydro-5-methoxy-9-oxo-4-acridinecarboxylic acid (0.8 g) with Intermediate 33(h) (0.93 g) gave, after trituration with ether, the title compound (0.31 g), MP: 182°.

Analysis Found: C,74.2; H,6.6; N,7.8; $C_{35}H_{37}N_3O_4$ Requires: C,74.6; H,6.6; N,7.5%.

EXAMPLE 79

N-[4-[2-[[2-(3,4-Dimethoxyphenyl)ethyl]methyl-amino]ethyl]phenyl]-9,10-dihydro-5-methoxy-9-oxo-4-acridinecarboxamide The coupling of 9,10-dihydro-5-methoxy-9-oxo-4-acridinecarboxylic acid (0.8 g) with Intermediate 33(e) (0.94 g) gave, after crystallisation from isopropanol, the title compound (0.17 g), MP: 179°.

Analysis Found: C,72.3; H,6.0; N,7.8; $C_{34}H_{35}N_3O_5$ Requires: C,72.2; H,6.2; N,7.4%.

EXAMPLE 80

N-[4-[4-[[2-(3,4-Dimethoxyphenyl)ethyl]methyl-amino]butyl]phenyl]-9,10-dihydro-5-methoxy-9-oxo-4-acridinecarboxamide The coupling of 9,10-dihydro-5-methoxy-9-oxo-4-acridinecarboxylic acid (0.8 g) with Intermediate 33(c) (1 g) gave, after crystallisation from isopropanol, the title compound (0.12 g), MP: 170°. IR gave signals at 1645 (CONH), 1620 (CO) and 3300 cm$^{-1}$ (NH).

EXAMPLE 81

N-[4-[3-[[(3,4-Dimethoxyphenyl)methyl]methyl-amino]propyl]phenyl]-9,10-dihydro-5-nitro-9-oxo-4-acridinecarboxamide The coupling of 9,10-dihydro-5-nitro-9-oxo-4-acridinecarboxylic acid (0.8 g) with Intermediate 33(f) (0.88 g) gave, after crystallisation from isopropanol, the title compound (0.29 g), MP: 192°.

Analysis Found: C,67.8; H,5.6; N,9.4; $C_{33}H_{32}N_4O_6$ Requires: C,68.3; H,5.6; N,9.65%.

EXAMPLE 82

N-[4-[3-[[(3,4-Dimethoxyphenyl)methyl]methyl-amino]propyl]phenyl]-9,10-dihydro-5-methoxy-9-oxo-4-acridinecarboxamide The coupling of 9,10-dihydro-5-methoxy-9-oxo-4-acridinecarboxylic acid (0.8 g) with Intermediate 33(f) (0.93 g) gave, after crystallisation from ethanol, the title compound (0.27 g), MP: 180°.

Analysis Found: C,72.0; H,6.1; N,7.6; $C_{34}H_{35}N_3O_5$ Requires: C,72.2; H,6.2; N,7.4%.

EXAMPLE 83

N-[4-[2-[(Phenylmethyl)ethyl-amino]ethoxy]phenyl]-9,10-dihydro-9-oxo-4-acridinecarboxamide The coupling of 9,10-dihydro-9-oxo-4-acridinecarboxylic acid (0.8 g) with Intermediate 36(i) (0.9 g) gave, after crystallisation from ethanol, the title compound (0.34 g), MP: 157°.

Analysis Found: C,75.3; H,5.9; N,8.4; $C_{31}H_{29}N_3O_3$ Requires: C,75.7; H,5.9; N,8.5%.

EXAMPLE 84

N-[4-[4-[[(3,4-Dimethoxyphenyl)methyl]methyl-amino]butyl]phenyl]-9,10-dihydro-10-methyl-9-oxo-4-acridinecarboxamide The coupling of 9,10-dihydro-10-methyl-9-oxo-4-acridinecarboxylic acid (0.8 g) with Intermediate 33(a) (1.04 g) gave, after crystallisation from isopropanol, the title compound (0.65 g), MP: 142°. IR gave signals at 1675 (CONH), 1610 (CO) and 3250 cm$^{-1}$ (NH).

EXAMPLE 85

N-[4-[2-[[(3,4-Dimethoxyphenyl)methyl]methyl-amino]ethyl]phenyl]-9,10-dihydro-10-methyl-9-oxo-4-acridinecarboxamide The coupling of 9,10-dihydro-10-methyl-9-oxo-4-acridinecarboxylic acid (0.87 g) with Intermediate 33(b) (1 g) gave, after crystallisation from isopropanol, the title compound (0.42 g), MP: 182°.

Analysis Found: C,73.5; H,6.1; N,7.8; $C_{33}H_{33}N_3O_4$ Requires: C,74.0; H,6.2; N,7.8%.

EXAMPLE 86

N-[4-[4-[[(3,4-Dimethoxyphenyl)methyl]methyl-amino]butyl]phenyl]-9,10-dihydro-7-methoxy-9-oxo-4-acridinecarboxamide The coupling of 9,10-dihydro-7-methoxy-9-oxo-4-acridinecarboxylic acid (0.8 g) with Intermediate 33(a) (0.97 g) gave, after crystallisation from isopropanol, the title compound (0.17 g), MP: 172°.

Analysis Found: C,71.5; H,6.4; N,6.9; $C_{35}H_{37}N_3O_5$, 0.5 $H_2O$ Requires: C,71.4; H,6.5; N,7.1%.

EXAMPLE 87

N-[4-[[2-[[(3,4-Dimethoxyphenyl)methyl]methyl-
amino]ethyl]thio]phenyl]-9,10-
dihydro-9-oxo-4-
acridinecarboxamide The coupling of 9,10-dihydro-9-oxo-4-acridinecarboxylic acid (0.7 g) with Intermediate 36(d) (1 g) gave, after crystallisation from isopropanol, the title compound (0.26 g), MP: 113°.

Analysis Found: C,69.3; H,5.5; N,7.4; S,5.8; $C_{32}H_{31}N_3O_4S$ Requires: C,69.4; H,5.6; N,7.6; S,5.8%.

EXAMPLE 88

N-[4-[[3-[[(3,4-Dimethoxyphenyl)methyl]methyl-
amino]propyl]thio]phenyl]-9,10-
dihydro-5-methyl-9-oxo-
4-acridinecarboxamide The coupling of 9,10-dihydro-5-methyl-9-oxo-4-acridinecarboxylic acid (0.8 g) with Intermediate 38(d) (1.09 g) gave, after crystallisation from ethanol, the title compound (50 mg), MP: 158°.

Analysis Found: C,69.4; H,5.9; N,6.9; S,5.6; $C_{34}H_{35}N_3O_4S$, 0.5 $H_2O$ Requires: C,69.1; H,6.1; N,7.1; S,5.4%.

EXAMPLE 89

N-[4-[[3-[[(3,4-Dimethoxyphenyl)methyl]methyl-
amino]propyl]thio]phenyl]-9,10-
dihydro-5-methoxy-9-oxo-
4-acridinecarboxamide The coupling of 9,10-dihydro-5-methoxy-9-oxo-4-acridinecarboxylic acid (1 g) with Intermediate 38(d) (1.28 g) gave, after crystallisation from acetonitrile, the title compound (0.37 g), MP: 184°–186°.

Analysis Found: C,68.1; H,5.9; N,6.8; S,5.2; $C_{34}H_{35}N_3O_5S$ Requires: C,68.3; H,5.9; N,7.0; S,5.4%.

EXAMPLE 90

N-[4-[[3-[[(3,4-Dimethoxyphenyl)methyl]methyl-
amino]propyl]thio]phenyl]-9,10-
dihydro-5-fluoro-9-oxo-
4-acridinecarboxamide The coupling of 9,10-dihydro-5-fluoro-9-oxo-acridinecarboxylic acid (0.9 g) with Intermediate 38(d) (1.1 g) gave, after crystallisation from isopropanol, the title compound (0.5 g), MP: 120°–130°.

Analysis Found: C,66.6; H,5.6; F,3.1; N,6.9; S,5.3; $C_{33}H_{32}FN_3O_4S$,0.5 $H_2O$ Requires: C,66.6; H,5.6; F,3.2; N,7.1; S,5.4%.

EXAMPLE 91

N-[4-[2-[[(3,4-Dimethoxyphenyl)methyl]methyl-
amino]ethyl]phenyl]-9,10-
dihydro-5-methylthio-9-oxo-
4-acridinecarboxamide The coupling of 9,10-dihydro-5-methylthio-9-oxo-4-acridinecarboxylic acid (0.7 g) with Intermediate 33(b) (0.74 g) gave, after crystallisation from ethanol, the title compound (0.3 g), MP: 190°.

Analysis Found: C,68.5; H,6.1; N,7.2; $C_{33}H_{33}N_3O_4S$, 0.5 $H_2O$ Requires: C,68.7; H,5.9; N,7.3%.

EXAMPLE 92

N-[4-[2-[[(3,4-Dimethoxyphenyl)methyl]methyl-
amino]ethyl]phenyl]-9,10-
dihydro-5-methyl-9-oxo-
4-acridinecarboxamide The coupling of 9,10-dihydro-5-methyl-9-oxo-4-acridinecarboxylic acid (1.27 g) with Intermediate 33(b) (1.5 g) gave, after crystallisation from isopropanol/diisopropylether, the title compound (0.3 g), MP: 119°.

Analysis Found: C,73.5; H,6.2; N,7.6; $C_{33}H_{33}N_3O_4$ Requires: C,74.0; H,6.2; N,7.8%.

EXAMPLE 93

N-[4-[3-[[(3,4-Dimethoxyphenyl)methyl]methyl-
amino]propoxy]phenyl]-9,10-
dihydro-5-methyl-9-oxo-
4-acridinecarboxamide The coupling of 9,10-dihydro-5-methyl-9-oxo-4-acridinecarboxylic acid (1 g) with Intermediate 38(c) (1.3 g) gave, after crystallisation from ispropanol, the title compound (0.9 g), MP: 160°.

Analysis Found: C,72.3; H,6.3; N,7.5; $C_{34}H_{35}N_3O_5$ requires: C,72.2; H,6.3; N,7.5%.

EXAMPLE 94

N-[4-[2-[[(3,4-Dimethoxyphenyl)methyl]methyl-
amino]ethylamino]phenyl]-9,10-
dihydro-5-methoxy-9-oxo-
4-acridinecarboxamide The coupling of 9,10-dihydro-5-methoxy-9-oxo-4-acridinecarboxylic acid (1.4 g) with Intermediate 43 (1.4 g) gave after crystallisation from isopropanol, the title compound (0.2 g), MP: 196°.

Analysis Found: C,69.8; H,6.3; N,10.0; $C_{33}H_{34}N_4O_5$ requires: C,69.9; H,6.1; N,9.9%.

EXAMPLE 95

N-[4-[2-[[(3,4-Dimethoxyphenyl)methyl]methyl-
amino]ethyl]phenyl]-9,10-
dihydro-5,8-dimethoxy-9-
oxo-4-acridinecarboxamide The coupling of 9,10-dihydro-5,8-dimethoxy-9-oxo-4-acridine carboxylic acid (0.8 g) with Intermediate 33(b) (0.67 g) gave, after crystallisation from ethanol, the title compound (0.15 g) MP: 196°.

EXAMPLE 96

N-[4-[2-[[(3,4-Dimethoxyphenyl)methyl]methyl-amino]ethyl]phenyl]-9,10-dihydro-5,7-dimethoxy-9-oxo-4-acridinecarboxamide The coupling of Intermediate 44 (1.4 g) with Intermediate 33(b) (1.2 g) gave, after crystallisation from ethanol, the title compound (0.25 g), MP>260°.

Analysis Found: C,70.09; H,6.35; N,7.01; $C_{34}H_{35}N_3O_6$ Requires C,70.20; H,6.06; N,7.22%.

Analysis Found: C,68.99; H,5.76; N,7.18; $C_{34}H_{35}N_3O_6$, 0.5 $H_2O$ Requires: C,69.13; H,6.14; N,7.11%.

EXAMPLE 97

N-[4-[2-[[(3,4-Dimethoxyphenyl)methyl]methyl-amino]ethyl]phenyl]-9,10-dihydro-6,7,8-trimethoxy-9-oxo-4-acridinecarboxamide The coupling of Intermediate 45 (0.6 g) with Intermediate 33(b) (0.6 g) gave, after crystallisation from isopropanol, the title compound (0.4 g), MP: 158°.

Analysis Found: C,68.69; H,6.32; N,6.40; $C_{35}H_{37}N_3O_7$ Requires: C,68.72; H,6.10; N,6.87%.

EXAMPLE 98

N-[4-[3-[[(3,4-Dimethoxy-phenyl)methyl]amino]propoxy]phenyl]-9,10-dihydro-9-oxo-4-acridinecarboxamide A mixture of Intermediate 40 (0.5 g) and 3,4-dimethoxy-benzenemethanamine (0.5 g) was heated for 1 h at 140°. Water was then added and the mixture was extracted with dichloromethane. The dried organic phase was concentrated to give a solid which was purified by column chromatography eluting with dichloromethane/methanol (9:1). The resulting solid was crystallised from benzene to give the title compound (50 mg), MP: 138°–139°.

Analysis Found: C,70.1; H,5.9; N,7.5; $C_{32}H_{31}N_3O_5$ (0.5 $H_2O$) Requires: C,70.3; H,5.9; N,7.7%.

EXAMPLE 99

Oxalate of N-[4-4-[[(3,4-Dimethoxyphenyl)methyl]methyl-amino]butyl]phenyl]-9,10-dihydro-9-oxo-4-acridinecarboxamide A solution of Example 41 (0.55 g) and oxalic acid dihydrate (0.126 g) in ethanol (10 ml) was boiled for 2 min. After cooling and scratching, crystallisation took place. The crystals were filtered off and dried to afford the title compound (0.55 g), MP: 155°–160°.

Analysis Found: C,66.3; H,5.9; N,6.3; $C_{36}H_{37}N_3O_8$ (0.5 $H_2O$) Requires: C,66.6; H,5.9; N,6.4%.

EXAMPLE 100

Maleate of N-[4-4-[[(3,4-dimethoxyphenyl)methyl]methyl-amino]butyl]phenyl]-9,10-dihydro-9-oxo-4-acridinecarboxamide A solution of Example 41 (0.55 g) and maleic acid (0.130 g) in ethanol (50 ml) was boiled for 2 min. After cooling and scratching, crystallisation took place. The crystals were filtered off and dried to afford the title compound (0.5 g), MP: 205°.

Analysis Found: C,68.2; H,5.9; N,6.2; $C_{38}H_{39}N_3O_8$ Requires: C,68.5; H,5.9; N,6.3%.

EXAMPLE 101

Hydrochloride of N-[4-4-[[(3,4-dimethoxyphenyl)methyl]methyl-amino]butyl]phenyl]-9,10-dihydro-9-oxo-4-acridinecarboxamide A hot solution of Example 41 (0.55 g) in ethanol (50 ml) was treated with a slight excess of an ethereal solution of hydrochloric acid. The solution was then concentrated to give a foam which was triturated with isopropanol to afford the title compound (0.4 g) as crystals, MP: 165°.

Analysis Found: C,67.6; H,6.3; N,7.0; $C_{34}H_{36}ClN_3O_4 \cdot H_2O$ Requires: C,67.5; H,6.4; N,7.0%.

EXAMPLE 102

L+ lactate of N-[4-4-[[(3,4-dimethoxyphenyl)methyl]methyl-amino]butyl]phenyl]-9,10-dihydro-9-oxo-4-acridinecarboxamide A solution of Example 41 (0.55 g) and L+ lactic acid (0.95 g) in isopropanol (30 ml) was boiled for 2 min. After cooling and scratching, crystallisation took place. The crystals were filtered off and dried to afford the title compound (0.45 g), MP: 120°.

Analysis Found: C,69.5; H,6.5; N,6.6; $C_{37}H_{41}N_3O_7$ Requires: C,69.4; H,6.6; N,6.5%.

EXAMPLE 103

Oxalate of N-[3-[3-[[(3,4-dimethoxyphenyl)methyl]methyl-amino]propyl]phenyl]-5-fluoro-9,10-dihydro-9-oxo-4-acridinecarboxamide A mixture of 5-fluoro-9,10-dihydro-9-oxo-4-acridinecarboxylic acid (1 g) and 1-hydroxybenzotriazole (0.63 g) in DMF (30 ml) was stirred at room temperature for 10 min. Intermediate 51 (1.23 g) in DMF (3.9 ml) was then added followed by dicyclohexylcarbodiimide (0.8 g) and the mixture was stirred at room temperature for 16 hours and then filtered. The filtrate was concentrated in vacuo, treated with dilute sodium hydroxide solution and extracted with methylene chloride. The combined, dried, organic extracts were evaporated to leave an oil which, after purified by column chromatography on silica gel eluting with methylene chloride/methanol (99:1), led to the title compound (1.1 g), m.p. 126°.

Analysis Found: C,63.9; H,5.4; F,2.8; N,6.2; $C_{33}H_{32}F_1N_3O_4 \cdot C_2H_2O_4$ ($H_2O$) Requires: C,63.5; H,5.5; F,2.9; N,6.3%

The following compounds were prepared in a similar manner to Example 103:

EXAMPLE 104

N-[3-[3-[[(3,4-Dimethoxyphenyl)methyl]methylamino]propoxy]phenyl]-9,10-dihydro-5-methoxy-9-oxo-4-acridinecarboxamide The coupling of 9,10-dihydro-5-methoxy-9-oxo-4-acridinecarboxylic acid (1.5 g) with Intermediate 48(b) (1.22 g) gave, after crystallisation from isopropanol, the title compound (0.47 g) as a solid, m.p. 124°.

Analysis Found: C,70.1; H,6.1; N,7.05; $C_{34}H_{35}N_3O_6$ Requires: C,70.2; H,6.1; N,7.2%

EXAMPLE 105

Oxalate of N-[3-[3-[[(3,4-dimethoxyphenyl)methyl]methylamino]propyl]phenyl]-9,10-dihydro-5-methoxy-9-oxo-4-acridinecarboxamide The coupling of 9,10-dihydro-5-methoxy-9-oxo-4-acridine carboxylic acid (1.26 g) with Intermediate 51 (1.23 g) gave the title compound (1.13 g) m.p 112°–114°.

Analysis Found: C,65.2; H,6.2; N,6.2; $C_{34}H_{35}N_3O_5 \cdot C_2H_2O_4$ (0.5 $H_2O$) Requires: C,65.0; H,5.8; N,6.3%

EXAMPLE 106

Fumarate of N-[3-[2-[[(3,4-dimethoxyphenyl)methyl]methylamino]ethyl]phenyl]-5-fluoro-9,10-dihydro-9-oxo-4-acridinecarboxamide The coupling of 5-fluoro-9,10-dihydro-9-oxo-4-acridinecarboxylic acid (0.34 g) with Intermediate 48(a) (0.4 g) gave the title compound (0.3 g), m.p. 155°.

EXAMPLE 107

Fumarate of N-[3-[2-[[(3,4-dimethoxyphenyl)methyl]methylamino]ethyl]phenyl]-9,10-dihydro-5-methoxy-9-oxo-4-acridinecarboxamide The coupling of 9,10-dihydro-5-methoxy-9-oxo-4-acridinecarboxylic acid (0.36 g) with Intermediate 48(a) (0.4 g) gave the title compound (0.13 g), m.p. 140°.

EXAMPLE 108

N-[4-[4-[[(3,4-Dimethoxyphenyl)methyl]methylamino]butyl]-2-methoxyphenyl]-9,10-dihydro-5-methoxy-9-oxo-4-acridinecarboxamide The coupling of 9,10-dihydro-5-methoxy-9-oxo-4-acridinecarboxylic acid (0.38 g) with Intermediate 55 (0.5 g) gave, after crystallisation from isopropanol, the title compound (0.36 g) as a solid, MP: 114°–115°.

Analysis Found: C,70.98; H,6.19; N,6.79; $C_{36}H_{39}N_3O_6$ Requires: C,70.92; H,6.45; N,6.89%.

EXAMPLE 109

9,10-Dihydro-5-methoxy-9-oxo-N-[4-[[2-(1,2,3,4-tetrahydro-6,7-dimethoxy-2-isoquinolinyl)ethyl]amino]phenyl]-4-acridine-carboxamide The coupling of 9,10-dihydro-5-methoxy-9-oxo-4-acridinecarboxylic acid (0.99 g) with Intermediate 59 (1.2 g) gave, after crystallisation from acetonitrile, the title compound (1.3 g), MP: 228°–234°.

Analysis Found: C,69.27; H,5.87; N,9.37; $C_{34}H_{34}N_4O_5$, 0.5 $H_2O$ Requires: C,69.48; H,6.00; N,9.50%.

EXAMPLE 110

N-[4-[2-(2,3-Dihydro-5,6-dimethoxy-1H-isoindol-2-yl)ethyl]phenyl]-9,10-dihydro-5-methoxy-9-oxo-4-acridinecarboxamide The coupling of 9,10-dihydro-5-methoxy-9-oxo-4-acridinecarboxylic acid (0.54 g) with Intermediate 60 (0.6 g) gave after crystallisation from ethanol, the title compound (0.3 g), MP: 215°–225°. NMR includes signals at d 2.85(4H,s,N—(CH$_2$)$_2$—Ph); 3.7(6H,s,2×OMe); 3.8(3H,s,OMe); 3.9(4H,s, 2×N—CH$_2$—Ph).

EXAMPLE 111

9,10-Dihydro-5,8-dimethoxy-N-[2-methoxy-4-[3-(1,2,3,4-tetrahydro-6,7-dimethoxy-2-isoquinolinyl)propyl]phenyl]-9-oxo-4-acridinecarboxamide The coupling of 9,10-dihydro-5,8-dimethoxy-9-oxo-4-acridinecarboxylic acid (0.7 g) with Intermediate 16(a) (0.83 g) gave, after crystallisation from ethanol, the title compound (0.1 g), MP: 140°.

Analysis Found: C,67.44; H,5.94; N,6.80; $C_{37}H_{39}N_3O_7$, $H_2O$ Requires: C,67.77; H,6.30; N,6.40%.

EXAMPLE 112

9,10-Dihydro-5-methoxy-N-[4-[2-(1,2,3,4-tetrahydro-6,7-dimethoxy-2-isoquinolinyl)-1-hydroxyethyl]phenyl]-9-oxo-4-acridinecarboxamide The coupling of 9,10-dihydro-5-methoxy-9-oxo-4-acridinecarboxylic acid (0.49 g) with Intermediate 63 (0.5 g) gave, after crystallisation from acetonitrile, the title compound (0.8 g), MP: 160°–165°.

Analysis Found: C,68.51; H,5.74; N,7.25; $C_{34}H_{33}N_3O_6$, $H_2O$ Requires: C,68.33; H,5.90; N,7.09%.

EXAMPLE 113

9,10-Dihydro-5-methoxy-9-oxo-N-[4-[[[2-(1,2,3,4-tetrahydro-6,7-dimethoxy-2-isoquinolinyl)ethyl]methylamino]methyl]phenyl]-4- acridinecarboxamide The coupling of 9,10-dihydro-5-methoxy-9-oxo-4-acridinecarboxylic acid (0.53 g) Intermediate 67 (0.7 g) gave, by precipitation from methylene chloride/diethyl ether, the title compound (0.5 g), MP: 202°.

Analysis Found: C,68.68; H,6.27; N,8.52; $C_{36}H_{38}N_4O_5$, 1.25 $H_2O$ Requires: C,68.71; H,6.48; N,8.90%.

EXAMPLE 114

N-[4-[[[2-[[(3,4-Dimethoxyphenyl)methyl]methylamino]ethyl]methylamino]methyl]phenyl]-9,10-dihydro-5-methoxy-9-oxo-4-acridinecarboxamide The coupling of 9,10-dihydro-5-methoxy-9-oxo-4-acridinecarboxylic acid (1.1 g) with Intermediate 70 (1.43 g) gave, after crystallisation from methanol, the title compound (0.75 g) as yellow crystals, MP: 170°.

Analysis Found: C,69.69; H,6.30; N,9.10; $C_{35}H_{38}N_4O_5$, 0.5 $H_2O$ Requires: C,69.63; H,6.51; N,9.28%.

EXAMPLE 115

5-Fluoro-9,10-dihydro-N-[2-methoxy-4-[3-(1,2,3,4-tetrahydro-6,7-dimethoxy-2-isoquinolinyl)phenyl]-9-oxo-4-acridinecarboxamide The coupling of 5-fluoro-9,10-dihydro-9-oxo-4-acridinecarboxylic acid (0.5 g) with Intermediate 16(a) (0.63 g) gave, after crystallisation from ethanol, the title compound (0.3 g), MP: 128°. NMR includes signals at d 3.6(3H,s, OMe); 3.8(6H,s,2×OMe); 9.15(1H,s,NHCO); 11.35(1H,s, NH acridone).

EXAMPLE 116

N-[4-[[3-[[(3,4-Dimethoxyphenyl)methyl]methylamino]propyl]thio]phenyl]-9,10-dihydro-5-(methylthio)-9-oxo-4-acridinecarboxamide The coupling of 9,10-dihydro-5-methylthio-9-oxo-4-acridinecarboxylic acid (0.3 g) with Intermediate 38(d) (0.36 g) gave, after crystallisation from methanol, the title compound (0.13 g), MP: 142°. NMR includes signals at d 2.2(3H,s,SMe); 2.45(3H,s,NMe); 3.7(6H,s,2×OMe).

EXAMPLE 117

N-[4-[3-[[(3,4-Dimethoxyphenyl)methyl]methylamino]propyl]-2-methoxyphenyl]-9,10-dihydro-5-methyl-9-oxo-4-acridinecarboxamide The coupling of 9,10-dihydro-5-methyl-9-oxo-4-acridinecarboxylic acid (0.75 g) and Intermediate 30 (1 g), after crystallisation from methanol, the title compound (0.1 g), MP: 111°. NMR includes signals at d 2.18(3H,s,NCH$_3$); 2.55(3H,s,CH$_3$ acridone); 3.42(2H,s,N—CH$_2$—Ph); 3.9(9H,3s,3×OMe).

EXAMPLE 118

N-[2-Ethoxy-4-[3-(1,2,3,4-tetrahydro-6,7-dimethoxy-2-isoquinolinyl)propyl]phenyl]-5-fluoro-9,10-dihydro-9-oxo-4-acridinecarboxamide The coupling of 5-fluoro-9,10-dihydro-9-oxo-4-acridinecarboxylic acid (1 g) with Intermediate 16(b) (0.86 g) gave, after crystallisation from acetonitrile, the title compound (0.4 g), MP: 200°. NMR includes signals at d 1,4(2H,t, C$\underline{H}_3$—CH$_2$); 3,7(6H,s,2×OMe).

EXAMPLE 119

N-[4-[4-[[(3,4-Dimethoxyphenyl)methyl]methylamino]-2-butenyl]phenyl]-9,10-dihydro-9-oxo-4-acridinecarboxamide The coupling of 9,10-dihydro-9-oxo-4-acridinecarboxylic acid (154 mg) with Intermediate 72 (210 mg) gave, after crystallisation from ethanol, the title compound (80 mg), MP: 140°.

Analysis Found: C,74.17; H,6.08; N,7.61; $C_{34}H_{33}N_3O_4$ Requires: C,74.55; H,6.07; N,7.67%.

EXAMPLE 120

N-[4-[3-[[(3,4-Dimethoxyphenyl)methyl]methylamino]-1-propenyl]phenyl]-9,10-dihydro-5-methoxy-9-oxo-4-acridinecarboxamide The coupling of 9,10-dihydro-5-methoxy-9-oxo-4-acridinecarboxylic acid (0.95 g) with Intermediate 74 (1.1 g) gave, after crystallisation from ethanol, the title compound (0.7 g), MP: 200°.

Analysis Found: C,72.46; H,6.04; N,7.61; $C_{34}H_{33}N_3O_5$ Requires: C,72.45; H,5.90; N,7.45%.

EXAMPLE 121

5-Methoxy-9-oxo-N-[4-[2-(1,2,3,4-tetrahydro-6-methoxy-2-isoquinolinyl)ethyl]phenyl]-9,10-dihydro-4-acridinecarboxamide The coupling of 9,10-dihydro-5-methoxy-9-oxo-4-acridinecarboxylic acid (0.5 g) with Intermediate 76 (0.48 g) gave, after crystallisation from pyridine/water, the title compound (0.4 g), MP: 260°.

Analysis Found: C,74.29; H,6.06; N,8.02; $C_{33}H_{31}N_3O_4$ requires: C,74.28; H,5.86; N,7.87%

EXAMPLE 122

5-Fluoro-9,10-dihydro-9-oxo-N-[3-[3-(1,2,3,4-tetrahydro-6,7-dimethoxy-2-isoquinolinyl)propyl]phenyl]-4-acridinecarboxamide The coupling of 5-fluoro-9,10-dihydro-9-oxo-4-acridinecarboxylic acid (1 g) with Intermediate 79 (1.3 g) gave, after crystallisation from isopropanol, the title compound (0.25 g), MP: 128°.

Analysis Found: C,68.84; H,5.67; F,3.01; N,6.88; $C_{34}H_{32}FN_3O_4$(1.5 $H_2O$) requires: C,68.90; H,5.95; F,3.20; N,7.09%

EXAMPLE 123

9,10-Dihydro-5-methoxy-9-oxo-N-[3-[3-(1,2,3,4-tetrahydro-6,7-dimethoxy-2-isoquinolinyl)propyl]phenyl]-4-acridinecarboxamide The coupling of 9,10-dihydro-5-methoxy-9-oxo-4-acridinecarboxylic acid (1.2 g) with Intermediate 79 (1.2 g) gave, after crystallisation from isopropanol, the title compound (0.5 g), MP: 138°–140°.

Analysis Found: C,70.55; H,6.25; N,7.06; $C_{35}H_{35}N_3O_5(H_2O)$ requires: C,70.56; H,6.26; N,7.05%

EXAMPLE 124

N-[4-[3-[[(3,4-Dimethoxyphenyl)methyl]methylamino]-2-hydroxypropoxy]phenyl]-9,10-dihydro-5-methoxy-9-oxo-4-acridinecarboxamide The coupling of 9,10-dihydro-5-methoxy-9-oxo-4-acridinecarboxylic acid (1 g) with Intermediate 81 (1.3 g) gave, after crystallisation from isopropanol, the title compound (0.7 g), MP: 175°.

Analysis Found: C,68.38; H,5.82; N,6.86; $C_{34}H_{35}N_3O_7$ requires: C,68.33; H,5.90; N,7.03%

EXAMPLE 125

9,10-Dihydro-5-methoxy-9-oxo-N-[4-[3-[[(3,4,5-trimethoxyphenyl)methyl]methylamino]propoxy]phenyl]-4-acridinecarboxamide The coupling of 9,10-dihydro-5-methoxy-9-oxo-4-acridinecarboxylic acid (1.5 g) with Intermediate 83 (1.3 g) gave, after crystallisation from isopropanol, the title compound (1.3 g), MP: 186°.

Analysis Found: C,68.82; H,6.08; N,6.83; $C_{35}H_{37}N_3O_7$ requires: C,68.72; H,6.10; N,6.87%

EXAMPLE 126

Fumarate of 5-fluoro-9,10-dihydro-N-[2-methoxy-5-[2-(1,2,3,4-tetrahydro-6,7-dimethoxy-2-isoquinolinyl)ethyl]phenyl]-9-oxo-4-acridinecarboxamide The coupling of 5-fluoro-9,10-dihydro-9-oxo-4-acridinecarboxylic acid (1 g) with Intermediate 86 (1.2 g) gave the title compound (0.5 g), MP: 166°–168°.

Analysis Found: C,63.78; H,5.15; N,6.10; $C_{38}H_{36}FN_3O_9(H_2O)$ requires: C,63.76; H,5.35; N,5.87%

EXAMPLE 127

9,10-Dihydro-9-oxo-N-[4-[3-(1,2,3,4-tetrahydro-2-isoquinolinyl)propoxy]phenyl]-4-acridinecarboxamide The coupling of 9,10-dihydro-9-oxo-4-acridinecarboxylic acid (0.8 g) with Intermediate 88 (0.9 g) gave, after crystallisation from ethanol, the title compound (0.3 g), MP: 182°.

Analysis Found: C,74.88; H,5.81; N,8.16; $C_{32}H_{29}N_3O_3(0.5\ H_2O)$ requires: C,74.98; H,5.90; N,8.20%

EXAMPLE 128

9,10-Dihydro-5-methoxy-9-oxo-N-[4-[2-(1,2,3,4-tetrahydro-7-methoxy-2-isoquinolinyl)ethyl]phenyl]-4-acridinecarboxamide The coupling of 9,10-dihydro-5-methoxy-9-oxo-4-acridinecarboxylic acid (0.7 g) with Intermediate 90 (0.7 g) gave, after crystallisation from isopropanol, the title compound (0.65 g), MP: 213°–216°.

Analysis Found: C,73.27; H,5.94; N,7.82; $C_{33}H_{31}N_3O_4(0.5\ H_2O)$ requires: C,73.04; H,5.94; N,7.74%

EXAMPLE 129

9,10-Dihydro-5-methoxy-9-oxo-N-[3-[2-(1,2,3,4-tetrahydro-6,7-dimethoxy-2-isoquinolinyl)ethyl]phenyl]-4-acridinecarboxamide The coupling of 9,10-dihydro-5-methoxy-9-oxo-4-acridinecarboxylic acid (0.5 g) with Intermediate 92 (0.57 g) gave, after crystallisation from isopropanol, the title compound (0.15 g), MP: 152°.

Analysis Found: C,71.33; H,5.77; N,7.16; $C_{34}H_{33}N_3O_5(0.5\ H_2O)$ requires: C,71.30; H,5.98; N,7.33%

EXAMPLE 130

5-Fluoro-9,10-dihydro-9-oxo-N-[3-[2-(1,2,3,4-tetrahydro-6,7-dimethoxy-2-isoquinolinyl)ethyl]phenyl]-4-acridinecarboxamide The coupling of 5-fluoro-9,10-dihydro-9-oxo-4-acridinecarboxylic acid (0.5 g) with Intermediate 92 (0.57 g) gave, after crystallisation from isopropanol, the title compound (0.35 g), MP: 178°.

Analysis Found: C,70.80; H,5.36; F,3.34; N,7.34; $C_{33}H_{30}FN_3O_4(0.5\ H_2O)$ requires: C,70.70; H,5.57; F,3.38; N,7.49%

EXAMPLE 131

Fumarate of N-[5-[2-[[(3,4-Dimethoxyphenyl)methyl]methylamino]ethyl]-2-methoxyphenyl]-5-fluoro-9,10-dihydro-9-oxo-4-acridinecarboxamide The coupling of 5-fluoro-9,10-dihydro-9-oxo-4-acridinecarboxylic acid (0.8 g) with Intermediate 95 (1 g) gave the title compound (0.5 g), MP: 140°–142°.

Analysis Found: C,62.4; H,5.1; N,5.8; $C_{37}H_{36}FN_3O_9(1.5\ H_2O)$ requires: C,62.35; H,5.5; N,5.9%

EXAMPLE 132

9,10- Dihydro-5-methoxy-9-oxo-N-[4-[2-(1,2,3,4-tetrahydro-5,6-dimethoxy-2-isoquinolinyl)ethyl]phenyl]-4-acridinecarboxamide The coupling of 9,10-dihydro-5-methoxy-9-oxo-4-acridinecarboxylic acid (0.19 g) with Intermediate 97 (0.22 g) gave, after crystallisation from pyridine/water, the title compound (0.32 g). MP: 235°–237°. NMR includes signals at d 2.6–3.0 (8H,m,2×N—(CH$_2$)$_2$—Ar), 3.6 (2H,s,N—CH$_2$—Ar), 3.75 (6H,bs,OCH$_3$), 4 (3H,s,OCH$_3$), 6.5–8.5 (12H,m, aromatics).

Analysis Found: C,72.38; H,5.80; N,7.41; $C_{34}H_{33}N_3O_5$ requires: C,72.45; H,5.90; N,7.45%.

EXAMPLE 133

9,10-Dihydro-5-methoxy-9-oxo-N-]4-[2-(1,2,3,4-tetrahydro-6,7,8-trimethoxy-2-isoquinolinyl)ethyl]phenyl]-4-acridinecarboxamide The coupling of 9,10-dihydro-5-methoxy-9-oxo-4-acridinecarboxylic acid (0.26 g) with Intermediate 99 (0.3 g) gave, after crystallisation from isopropanol, the title compound (0.3 g), MP: 222°–226°. NMR includes signals at d 2.4–2.9 (8H,m,2×N—$(CH_2)_2$—Ar), 3.45 (2H,s,N—$CH_2$—Ar), 3.7 (9H,bs,$OCH_3$), 3.9 (3H,s,$OCH_3$), 6.2–8.4 (11H,m,aromatics).

Analysis Found: C,69.46; H,6.14; N,6.84; $C_{35}H_{35}N_3O_6$ (0.5 $H_2O$) requires: C,69.75; H,6.02; N,6.97%.

EXAMPLE 134

5-Amino-N-[4-[4-[[(3,4-dimethoxyphenyl)methyl]methylamino]butyl]phenyl]-9,10-dihydro-9-oxo-4-acridinecarboxamide A suspension of Example 75 (0.15 g) in ethanol (40 ml) was hydrogenated at room temperature in presence of 10% palladium-on-carbon (70 mg). After the hydrogen absorption was completed, the mixture was diluted with methylene chloride (50 ml). The catalyst was filtered off and the solution concentrated in vacuo to give the title compound (85 mg) as a yellow solid, MP: 250°.

Analysis Found: C,72.38; H,6.69; N,9.06; $C_{34}H_{36}N_4O_4$ Requires: C,72.31; H,6.42; N,9.92%.

EXAMPLE 135

9,10-Dihydro-5-methoxy-9-oxo-N-[4-[2-(1,2,3,4-tetrahydro-6,7-dimethoxy-2-isoquinolinyl)ethyl]phenyl]-4-acridinecarboxamide Dicyclohexylcarbodiimide (22.76 g) in DMF (50 ml) was added dropwise to a stirred mixture of 9,10-dihydro-5-methoxy-9-oxo-4-acridinecarboxylic acid (28.9 g) and 1-hydroxybenzotriazole hydrate (15.66 g) in DMF (300 ml) maintained at 0°, followed by Intermediate 101 (33.5 g) in DMF (150 ml). After 4 hours at 0° and 2 days at room temperature, the mixture was filtered, the filtrate was concentrated in vacuo and the residue taken up in 1N sodium hydroxide and extracted with dichloromethane. The organic layer was then washed with water, dried and evaporated to give a solid residue. This was dissolved in 500 ml of boiling pyridine and the solution was clarified by filtration. The clear solution was diluted with 10 ml of water and the product crystallised on cooling to give the title compound (52.82 g). M.p.: 215°–225°.

NMR includes d 2.60–2.95 (m,8H,$CH_2$); 3.58 (s,2H,N—$\underline{CH_2}$—Ph); 3.72 (s,6H,OMe); 4.05 (s,3H,OMe acridone); 6.78 (2s,2H,Ar.isoquinoline), 7.20–7.88 (m,8H,Ar.), 8.48 (t,2H,$H_1$ and $H_8$ acridone), 10.60 (s, 1H,CONH), 12.32 (s, 1H,NH acridone).

Analysis found: C,72.07; H,5.96; N,7.35; $C_{34}H_{33}N_3O_5$ requires: C,72.45; H,5.90; N,7.45%.

EXAMPLE 136

Maleate salt of 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide Example 135 (100 mg) was dissolved in 50 ml of a mixture of dichloromethane and methanol (1:1) and maleic acid (22 mg) was added. The mixture was boiled until a clear solution was obtained and the solution was evaporated in vacuo. The residue was taken up in hot methanol and cooled to give the title compound as yellow needles (90 mg). M.P.: 171° to 187°.

In the same way the following salts of Example 135 were prepared:

| | |
|---|---|
| Fumarate: | m.p.: 170–203°. |
| Succinate: | m.p.: 135–143°. |
| L(+)Tartrate: | m.p.: 165–180°. |

EXAMPLE 137

Hydrochloride salt of 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide Example 135 (100 mg) was dissolved in a mixture of methanol and dichloromethane (4:1) and excess methanolic hydrogen chloride was added. The solvate was recovered which after addition of diethyl ether and filtration gave the title compound (ca. 100 mg). MP 225° (softens with progressive loss of solvent).

EXAMPLE 138

In Vitro Cytotoxicity of MDR Inhibitors in Chinese Hamster Ovary Cells

The multidrug resistant Chinese Hamster Ovary (CHO) cell line $CH^RC5$ was obtained from Dr V Ling, Princess Margaret Hospital, Toronto, Canada and maintained as anchorage-dependent monolayers in a-minimum essential medium supplemented with thymidine, adenosine, 10% fetal bovine serum, 2 mM L-glutamine (Flow), 100 units/ml penicillin and 100 mg/ml streptomycin in a humidified atmosphere of 95% air and 5% carbon dioxide. Cells were passaged into culture flasks twice a week after dissociation with EDTA.

$CH^RC5$ cells were seeded at a density of $10^4$ cells/well in microtitre plates. After 24 hours, the medium was removed and replaced by 0.1 ml of fresh medium containing successive two-fold dilutions of MDR inhibitors. Each MDR inhibitor was assayed in duplicate in two-fold dilution from 1250 to 20 nM. The last well of each column was utilised to verify the lack of toxicity at the top dose of the MDR inhibitor in the absence of doxorubicin. Other control conditions were assayed on each microtitre plate: cells alone (1 well), doxorubicin alone (7 wells), amiodarone (a range of two-fold dilutions starting at 5 mM; two wells each). 0.1 ml of a 10 mg/ml solution of doxorubicin was added. After 72 hours incubation cell viability was assessed by the reduction of 3-[4,5-dimethylthiazol-2-yl]-2,5-diphenyltetrazolium bromide (MTT; Sigma) to a dark blue formazan product. In particular, 20 ml of a 5 mg/ml solution of MTT prepared in phosphate buffered saline was added to each well. After 4 hours incubation at 37°, the medium was aspirated and replaced with 0.1 ml dimethylsulphoxide. After vigorous shaking, the quantity of formazan product formed was assessed by its optical density at 550 nm. The absorbance is directly related to the number of surviving cells in the wells.

Cytotoxicity calculations were performed on the average of the two wells for each condition. The concentration of each MDR inhibitor giving a 50% reduction of the optical density relative to cells treated with doxorubicin alone was determined to give an $EC_{50}$ value.

RESULTS

In the above test the compounds of the specific Examples hereinabove had $EC_{50}$ values in the range of 0.018 to 0.72 mM. Thus, for example, the compound of Example 1 had an $EC_{50}$ of 0.02 mM, at least 100 times more potent than prototype MDR inhibitors including amiodarone ($EC_{50}$ 3 mM) and verapamil (3 mM).

Administration of the compound of Example 1 to mice orally produced no visible toxic effects at single doses up to 300 mg/kg.

The following are examples of pharmaceutical compositions according to the invention. The term 'Active Ingredient' as used hereinafter means a compound of the invention and may be for example the compound of Example 1.

| Example A - Oral Tablet | Per Tablet (mg) |
| --- | --- |
| Active Ingredient | 50.0 |
| Microcrystalline Cellulose | 110.0 |
| Lactose | 67.5 |
| Sodium Starch Glycolate | 20.0 |
| Magnesium Stearate | 2.5 |
| Total | 250.0 |

The drug is sieved through a 250 mm sieve and then the five powders are intimately mixed in a blender and compressed on ⅜ inch standard concave punches in a tabletting machine.

| Example B - Oral Capsule | Per Capsule (mg) |
| --- | --- |
| Active Ingredient | 50.0 |
| Microcrystalline Cellulose | 66.5 |
| Lactose USP | 66.5 |
| Sodium Starch Glycolate | 15.0 |
| Magnesium Stearate | 2.0 |
| Total | 200.0 |

The drug is sieved through a 250 mm sieve and then the five powders are intimately mixed in a blender and filled into No. 2 hard gelatin capsule shells on a capsule filling machine.

| Example C - Injection for Intravenous Administration (10 mg in 10 mL) | % w/w |
| --- | --- |
| Active Ingredient | 0.1 |
| Cancer chemotherapy agent | as required |
| Water for Injection to | 100.0 |
| Dilute hydrochloric acid to | pH3.0 |

The active ingredient (and cancer chemotherapy agent where appropriate) is dissolved with mixing in the Water For Injection, adding acid slowly until the pH is 3.0. The solution is sparged with nitrogen and filtratively sterilized through a sterilized filter of 0.22 micron pore size. Under aseptic conditions this sterile solution is placed into sterile ampoules and the ampoules flame sealed.

| Example D - Oral Syrup | % w/v |
| --- | --- |
| Active Ingredient | 2.0 |
| Cancer chemotherapy agent | as required |
| Dilute hydrochloric acid to | pH3.0 |
| Sobitol solution | 60 v/v |
| Flavour | as required |
| Distilled water to | 100 |

The active ingredient (and cancer chemotherapy agent where appropriate) is dissolved in some of the water with stirring by adding gradually the hydrochloric acid until the pH is 3.0. The sorbitol solution, flavour and the rest of the water are added and the pH re-adjusted to 3.0. The syrup is clarified by filtration through suitable filter pads.

We claim:

1. A compound of formula (1a):

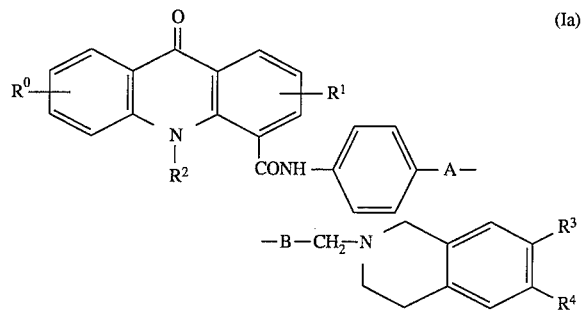

wherein $R^0$ represents a hydrogen or halogen atom, or a $C_{1-4}$ alkyl, $C_{1-4}$ alkoxy, $C_{1-4}$ alkylthio or nitro group;

$R^1$ represents a hydrogen or halogen atom, or a $C_{1-4}$ alkyl, $C_{1-4}$ alkoxy or $C_{1-4}$ alkylthio group;

$R^2$ represents a hydrogen atom or a $C_{1-4}$ alkyl group;

A represents an oxygen or a sulphur atom or a bond;

B represents an unsubstituted $C_{1-4}$ alkylene chain;

$R^4$ and $R^5$ each independently represents a $C_{1-4}$ alkoxy group; or physiologically acceptable salts or solvates thereof.

2. A compound according to claim 1 in which $R^0$ represents a hydrogen or fluorine atom or a $C_{1-4}$ alkoxy or $C_{1-4}$ alkyl group, $R^1$ and $R^2$ each represent a hydrogen atom and $R^4$ and $R^5$ each represents a $C_{1-4}$ alkoxy group.

3. A compound according to claim 2 in which the $R^0$ group is situated at the 5-position of the acridone molecule.

4. A compound according to claim 1 selected from the group consisting of 9,10-dihydro-5-methoxy-9-oxo-N-[4-[[3-(1,2,3,4-tetrahydro-6,7-dimethoxy-2-isoquinolinyl)propyl]thio]phenyl]-4-acridinecarboxamide;

5-fluoro-9,10-dihydro-9-oxo-N-[4-[[3-(1,2,3,4-tetrahydro-6,7-dimethoxy-2-isoquinolinyl)propyl]thio]phenyl]-4-acridinecarboxamide;

9,10-dihydro-5-methoxy-9-oxo-N-[4-[3-(1,2,3,4-tetrahydro-6,7-dimethoxy-2-isoquinolinyl)propoxy]phenyl]-4-acridinecarboxamide;

9,10-dihydro-5-methyl-9-oxo-N-[4-[[3-(1,2,3,4-tetrahydro-6,7-dimethoxy-2-isoquinolinyl)propyl]thio]phenyl]-4-acridinecarboxamide;

9,10-dihydro-5-methoxy-N-[2-methoxy-4-[3-(1,2,3,4-tetrahydro-6,7-dimethoxy-2-isoquinolinyl)propyl]phenyl]-9-oxo-4-acridinecarboxamide;

9,10-dihydro-N-[2-methoxy-4-[3-(1,2,3,4-tetrahydro-6,7-dimethoxy-2-isoquinolinyl)propyl]phenyl]-5-methyl-9-oxo-4-acridinecarboxamide;

and physiologically acceptable salts and solvates thereof.

5. A compound according to claim 1 selected from the group consisting of

N-[4-[4-[[(3,4-dimethoxyphenyl)methyl]methylamino]butyl]phenyl]-9,10-dihydro-9-oxo-4-acridinecarboxamide;

N-[4-[2-[[(3,4-dimethoxyphenyl)methyl]methylamino]ethyl]phenyl]-9,10-dihydro-9-oxo-4-acridinecarboxamide;

N-[4-[4-[[(3,4-dimethoxyphenyl)methyl]methylamino]butyl]phenyl]-5-fluoro-9,10-dihydro-9-oxo-4-acridinecarboxamide;

N-[4-[2-[[(3,4-dimethoxyphenyl)methyl]methylamino]ethyl]phenyl]-9,10-dihydro-5-methoxy-9-oxo-4-acridinecarboxamide;

N-[4-[3-[[(3,4-dimethoxyphenyl)methyl]methylamino]propyl]phenyl]-5-fluoro-9,10-dihydro-9-oxo-4-acridinecarboxamide;

N-[4-[2-[[(3,4-dimethoxyphenyl)methyl]methylamino]ethyl]phenyl]-5-fluoro-9,10-dihydro-9-oxo-4-acridinecarboxamide;

N-[4-[[3-[[(3,4-dimethoxyphenyl)methyl]methylamino]propyl]thio]phenyl]-9,10-dihydro-5-methoxy-9-oxo-4-acridinecarboxamide;

N-[4-[[3-[[(3,4-dimethoxyphenyl)methyl]methylamino]propyl]thio]phenyl]-9,10-dihydro-9-oxo-4-acridinecarboxamide;

N-[4-[4-[[(3,4-dimethoxyphenyl)methyl]methylamino]butyl]phenyl]-9,10-dihydro-5-methoxy-9-oxo-4-acridinecarboxamide;

N-[4-[3-[[2-(3,4-dimethoxyphenyl)ethyl]methylamino]propyl]phenyl]-9,10-dihydro-9-oxo-4-acridinecarboxamide;

N-[4-[2-[[2-(3,4-dimethoxyphenyl)ethyl]methylamino]ethoxy]phenyl]-9,10-dihydro-5-methoxy-9-oxo-4-acridinecarboxamide;

N-[4-[3-[[(3,4-dimethoxyphenyl)methyl]methylamino]propoxy]phenyl]-9,10-dihydro-9-oxo-4-acridinecarboxamide;

N-[4-[3-[[(3,4-dimethoxyphenyl)methyl]methylamino]propoxy]phenyl]-5-fluoro-9,10-dihydro-9-oxo-4-acridinecarboxamide;

N-[4-[2-[[2-(3,4-dimethoxyphenyl)ethyl]methylamino]ethyl]phenyl]-9,10-dihydro-9-oxo-4-acridinecarboxamide;

N-[4-[5-[[(3,4-dimethoxyphenyl)methyl]methylamino]pentyl]phenyl]-5-fluoro-9,10-dihydro-9-oxo-4-acridinecarboxamide;

N-[4-[3-[[(3,4-dimethoxyphenyl)methyl]methylamino]propyl]phenyl]-9,10-dihydro-9-oxo-4-acridinecarboxamide;

N-[4-[2-[[(3,4-dimethoxyphenyl)methyl]methylamino]ethylamino]phenyl]-9,10-dihydro-5-methoxy-9-oxo-4-acridinecarboxamide;

N-[4-[[3-[[(3,4-dimethoxyphenyl)methyl]methylamino]propyl]thio]phenyl]-9,10-dihydro-5-fluoro-9-oxo-4-acridinecarboxamide;

N-[4-[2-[[(3,4-dimethoxyphenyl)methyl]methylamino]ethyl]phenyl]-9,10-dihydro-5-methylthio-9-oxo-4-acridinecarboxamide;

N-[4-[2-[[(3,4-dimethoxyphenyl)methyl]methylamino]ethyl]phenyl]-9,10-dihydro-5-methyl-9-oxo-4-acridinecarboxamide;

N-[4-[3-[[(3,4-dimethoxyphenyl)methyl]methylamino]propoxy]phenyl]-9,10-dihydro-5-methyl-9-oxo-4-acridinecarboxamide;

N-[4-[2-[[2-(3,4-dimethoxyphenyl)ethyl]methylamino]ethyl]phenyl]-9,10-dihydro-9-oxo-4-acridinecarboxamide;

N-[4-[4-[[2-(3,4-dimethoxyphenyl)ethyl]methylamino]butyl]phenyl]-9,10-dihydro-9-oxo-4-acridinecarboxamide;

N-[4-[2-[[2-(4-methoxyphenyl)ethyl]methylamino]ethyl]phenyl]-9,10-dihydro-9-oxo-4-acridinecarboxamide;

N-[4-[2-[[2-(3,4-dimethoxyphenyl)ethyl]methylamino]ethoxy]phenyl]-9,10-dihydro-2-(methylthio)-9-oxo-4-acridinecarboxamide;

N-[4-[3-[[2-(3,4-dimethoxyphenyl)ethyl]methylamino]propoxyl]phenyl]-9,10-dihydro-9-oxo-4-acridinecarboxamide;

N-[4-[2-[[2-(4-methoxyphenyl)ethyl]methylamino]ethoxy]phenyl]-9,10-dihydro-9-oxo-4-acridinecarboxamide;

N-[4-[2-[[(3,4-dimethoxyphenyl)methyl]methylamino]ethoxy]phenyl]-9,10-dihydro-9-oxo-4-acridinecarboxamide;

N-[4-[3-[[(3,4-dimethoxyphenyl)methyl]methylamino]propoxy]phenyl]-9,10-dihydro-5-methoxy-9-oxo-4-acridinecarboxamide;

N-[4-[[2-[[(3,4-dimethoxyphenyl)methyl]methylamino]ethyl]thio]phenyl]-9,10-dihydro-9-oxo-4-acridinecarboxamide;

and physiologically acceptable salts and solvates thereof.

6. A pharmaceutical composition which comprises an effective amount of a compound according to claim 1 to improve or increase the efficacy of an antitumor drug, or increase or restore sensitivity of a tumor to an antitumor drug, or reverse or reduce resistance of a tumor to an antitumor drug, together with one or more physiologically acceptable carriers or excipients.

7. A pharmaceutical composition according to claim 6, wherein the antitumor drug is selected from Vinca alkaloids, anthracyclines, taxol and derivatives thereof, podophyllotoxins, mitoxantrone, actinomycin, colchicine, gramicidine D, amsacrine or any drug having cross resistance with above drugs characterized by the so-called MDR phenotype.

8. A compound which is 9,10-dihydro-5-methoxy-9-oxo-N-[4-[2-(1,2,3,4-tetrahydro-6,7-dimethoxy-2-isoquinolinyl)ethyl]phenyl]-4-acridinecarboxamide or a physiologically acceptable salt or solvate thereof.

9. A pharmaceutical composition comprising a compound according to claim 8, together with one or more physiologically acceptable carriers or excipients.

10. A pharmaceutical composition according to claim 9 in unit dosage form.

11. A pharmaceutical composition which comprises an effective amount of a compound according to claim 8 to improve or increase the efficacy of an antitumor drug, or increase or restore sensitivity of a tumor to an antitumor drug, or reverse or reduce resistance of a tumor to an antitumor drug, together with one or more physiologically acceptable carriers or excipients.

12. A pharmaceutical composition according to claim 11, wherein the antitumor drug is selected from Vinca alkaloids, anthracyclines, taxol and derivatives thereof, podophyllotoxins, mitoxantrone, actinomycin, colchicine, gramicidine D, amsacrine or any drug having cross resistance with above drugs characterized by the so-called MDR phenotype.

13. Hydrochloride salt of 9,10-dihydro-5-methoxy-9-oxo-N-[4-[2-(1,2,3,4-tetrahydro-6,7-dimethoxy-2-isoquinolinyl] phenyl]-4-acridine carboxamide.

14. A pharmaceutical composition comprising an effective amount of a compound according to claim 13 to improve or increase the efficacy of an antitumor drug, or increase or restore sensitivity of a tumor to an antitumor drug, or reverse or reduce resistance of a tumor to an antitumor drug, together with one or more physiologically acceptable carriers or excipients.

15. A pharmaceutical composition according to claim 14, wherein the antitumor drug is selected from Vinca alkaloids, anthracyclines, taxol and derivatives thereof, podophyllotoxins, mitoxantrone, actinomycin, colchicine, gramicidine D, amsacrine or any drug having cross resistance with above drugs characterized by the so-called MDR phenotype.

* * * * *